(12) United States Patent
Izpisua Belmonte et al.

(10) Patent No.: US 11,959,094 B2
(45) Date of Patent: Apr. 16, 2024

(54) METHODS AND COMPOSITIONS FOR GENOME EDITING IN NON-DIVIDING CELLS

(71) Applicant: Salk Institute for Biological Studies, La Jolla, CA (US)

(72) Inventors: Juan Carlos Izpisua Belmonte, La Jolla, CA (US); Keiichiro Suzuki, La Jolla, CA (US); Reyna Hernandez-Benitez, La Jolla, CA (US); Jun Wu, Farmers Branch, TX (US); Yuji Tsunekawa, Kobe (JP)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 18/311,000

(22) Filed: May 2, 2023

(65) Prior Publication Data
US 2023/0399663 A1  Dec. 14, 2023

Related U.S. Application Data

(62) Division of application No. 16/318,120, filed as application No. PCT/US2017/042151 on Jul. 14, 2017, now Pat. No. 11,674,158.

(60) Provisional application No. 62/363,164, filed on Jul. 15, 2016.

(51) Int. Cl.
| C12N 15/90 | (2006.01) |
| A61K 48/00 | (2006.01) |
| A61P 25/28 | (2006.01) |
| A61P 35/00 | (2006.01) |
| C12N 9/22 | (2006.01) |
| C12N 15/11 | (2006.01) |
| C12N 15/113 | (2010.01) |
| C12N 15/86 | (2006.01) |

(52) U.S. Cl.
CPC ............ *C12N 15/907* (2013.01); *A61K 48/00* (2013.01); *A61K 48/005* (2013.01); *A61K 48/0066* (2013.01); *A61P 25/28* (2018.01); *A61P 35/00* (2018.01); *C12N 9/22* (2013.01); *C12N 15/111* (2013.01); *C12N 15/113* (2013.01); *C12N 15/86* (2013.01); *C07K 2319/09* (2013.01); *C12N 2310/20* (2017.05); *C12N 2320/35* (2013.01); *C12N 2750/14143* (2013.01); *C12Y 301/01* (2013.01)

(58) Field of Classification Search
CPC .............. C12N 15/907; C12N 15/113; C12N 2310/20; A61K 48/0066; A61P 25/28
See application file for complete search history.

(56) References Cited

U.S. PATENT DOCUMENTS

| 4,186,183 A | 1/1980 | Alving et al. |
| 4,217,344 A | 8/1980 | Handjani et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 6,479,626 B1 | 11/2002 | Kim et al. |
| 6,534,261 B1 | 3/2003 | Cox, III et al. |
| 6,607,882 B1 | 8/2003 | Cox, III et al. |
| 6,746,838 B1 | 6/2004 | Choo et al. |
| 6,794,136 B1 | 9/2004 | Eisenberg et al. |
| 6,824,978 B1 | 11/2004 | Cox, III et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,585,849 B2 | 9/2009 | Liu et al. |
| 7,595,376 B2 | 9/2009 | Kim et al. |
| 8,440,431 B2 | 5/2013 | Voytas et al. |

(Continued)

FOREIGN PATENT DOCUMENTS

| WO | WO-9116024 A1 | 10/1991 |
| WO | WO-9117424 A1 | 11/1991 |

(Continued)

OTHER PUBLICATIONS

Ahmad et al. Antibody-mediated specific binding and cytotoxicity of liposome-entrapped doxorubicin to lung cancer cells in vitro. Cancer Res. 52:4817-4820 (1992).

(Continued)

*Primary Examiner* — Paul J Holland
(74) *Attorney, Agent, or Firm* — Klarquist Sparkman, LLP

(57) ABSTRACT

Disclosed herein are homology-independent targeted integration methods of integrating an exogenous DNA sequence into a genome of a non-dividing cell and compositions for such methods. Methods herein comprise contacting the non-dividing cell with a composition comprising a targeting construct comprising the exogenous DNA sequence and a targeting sequence, a complementary strand oligonucleotide homologous to the targeting sequence, and a nuclease, thereby altering the genome of the non-dividing cell.

20 Claims, 55 Drawing Sheets

Specification includes a Sequence Listing.

(56) References Cited

U.S. PATENT DOCUMENTS

| | | | |
|---|---|---|---|
| 8,440,432 | B2 | 5/2013 | Voytas et al. |
| 8,450,471 | B2 | 5/2013 | Voytas et al. |
| 8,586,363 | B2 | 11/2013 | Voytas et al. |
| 8,697,853 | B2 | 4/2014 | Voytas et al. |
| 2003/0232410 | A1 | 12/2003 | Liljedahl et al. |
| 2009/0203140 | A1 | 8/2009 | Amacher et al. |
| 2015/0275168 | A1 | 10/2015 | Oxburgh et al. |
| 2016/0208243 | A1 | 7/2016 | Zhang et al. |
| 2017/0205396 | A1 | 7/2017 | Izpisua-Belmonte et al. |
| 2017/0283777 | A1 | 10/2017 | Izpisua et al. |
| 2018/0273905 | A1 | 9/2018 | Kawamoto et al. |

FOREIGN PATENT DOCUMENTS

| | | |
|---|---|---|
| WO | WO-9324641 A2 | 12/1993 |
| WO | WO-9426877 A1 | 11/1994 |
| WO | WO-2013176772 A1 | 11/2013 |
| WO | WO-2015130935 A1 | 9/2015 |
| WO | WO-2018013932 A1 | 1/2018 |

OTHER PUBLICATIONS

Anderson. Human gene therapy. Science 256(5058):808-813 (1992).
Auer et al. Highly efficient CRISPR/Cas9-mediated knock-in in zebrafish by homology-independent DNA repair Genome Res 24:142-153 (2014).
Bachu et al. CRISPR-Cas targeted plasmid integration into mammalian cells via non-homologous end joining. Biotechnol Bioeng 112(10):2154-2162 (2015).
Behr et al. Gene transfer with synthetic cationic amphiphiles: prospects for gene therapy. Bioconjugate Chem. 5:382-389 (1994).
Beurdeley et al. Compact designer TALENs for efficient genome engineering. Nat Commun 4:1762 (2013), 8 pages.
Bitter et al. Expression and secretion vectors for yeast. Methods Enzymol 153:516-544 (1987).
Blaese et al. Vectors in cancer therapy: how will they deliver? Cancer Gene Ther. 2:291-297 (1995).
Buchscher et al. Human immunodeficiency virus vectors for inducible expression of foreign genes. J. Virol. 66:2731-2739 (1992).
Cristea et al. In vivo cleavage of transgene donors promotes nuclease-mediated targeted integration. Biotechnol Bioeng 110(3):871-880 (2013).
Crystal. Transfer of genes to humans: early lessons and obstacles to success. Science 270:404-410 (1995).
Cyranoski. Authors retract controversial NgAgo gene-editing study Researchers pull study after several failed attempts by others to replicate findings describing a proposed alternative to CRISPR. Nature News & Comment. From http://www.nature.com/news/authors-retract-controversial-ngago-gene-editing-study-1.22412 (3 pgs.) (Aug. 3, 2017).
Dillon. Regulating gene expression in gene therapy. Trends Biotechnol 11:167-175 (1993).
Funahashi et al. Zona reaction in porcine oocytes fertilized in vivo and in vitro as seen with scanning electron microscopy. Biol Reprod 63:1437-1442 (2000).
Gaj et al. Targeted gene knockout by direct delivery of zinc-finger nuclease proteins. Nat Methods 9(8):805-807 (2012).
Gao et al. Cationic liposome-mediated gene transfer. Gene Therapy 2:710-722 (1995).
Garrison et al. Haplotype-based variant detection from short-read sequencing. arXiv preprint arXiv:1207.3907 (9 pgs) (2012).
Hackl et al. Tracking the fate of glomerular epithelial cells in vivo using serial multiphoton imaging in novel mouse models with fluorescent lineage tags. Nat Med 19(12):1661-1666 (2013).
He et al. Knock-in of large reporter genes in human cells via CRISPR/Cas9-induced homology-dependent and independent DNA repair. Nucleic Acids Res 44(9):e85 (2016).
Hermonat et al. Use of adeno-associated virus as a mammalian DNA cloning vector: Transduction of neomycin resistance into mammalian tissue culture cells. PNAS USA 81:6466-6470 (1984).
Hochstrasser et al. Cutting it close: CRISPR-associated endoribonuclease structure and function. Trends Biochem Sci 40(1):58-66 (2015).
Holm et al. High bovine blastocyst development in a static in vitro production system using sofaa medium supplemented with sodium citrate and myo-inositol with or without serum-proteins. Theriogenology 52(4):683-700 (1999).
Hsu et al. DNA targeting specificity of RNA-guided Cas9 nucleases. Nat Biotechnol 31(9):827-832 (2013).
Imberti et al. Renal progenitors derived from human iPSCs engraft and restore function in a mouse model of acute kidney injury. Scientific Reports 5:8826 (2015).
Jinek et al. A programmable dual-RNA-guided DNA endonuclease in adaptive bacterial immunity. Science 337:816-821 (2012).
Jinek et al. RNA-programmed genome editing in human cells. elife 2 (2013): e00471.
Johann et al. GLVR1, a receptor for gibbon ape leukemia virus, is homologous to a phosphate permease of Neurospora crassa and is expressed at high levels in the brain and thymus. J Virol. 66(3):1635-1640 (1992).
Joung et al. TALENs: a widely applicable technology for targeted genome editing. Nat Rev Mol Cell Biol 14.1 (2013): 49-55.
Kay et al. A robust system for production of minicircle DNA vectors. Nature Biotechnol 28:1287-1289 (2010).
Kim et al. Precision genome engineering with programmable DNA-nicking enzymes. Genome Res 22(7):1327-1333 (2012).
Kobayashi et al. Generation of rat pancreas in mouse by interspecific blastocyst injection of pluripotent stem cells. Cell 142:787-799 (2010).
Kotin. Prospects for the use of adeno-associated virus as a vector for human gene therapy. Hum Gene Ther. 5(7):793-801 (1994).
Kremer et al. Adenovirus and adeno-associated virus mediated gene transfer. Br Med Bull. 51(1):31-44 (1995).
Kutner et al. Production, concentration and titration of pseudotyped HIV-1-based lentiviral vectors. Nature Protocols 4:495-505 (2009).
Lampe et al. Intravenous Injections in Neonatal Mice. J Vis Exp 93:e52037 (2014).
Li et al. BMP4 Signaling Acts via dual-specificity phosphatase 9 to control ERK activity in mouse embryonic stem cells. Cell Stem Cell 10:171-182 (2012).
Li et al. Fast and accurate short read alignment with burrows-wheeler transform. Bioinformatics 25(14):1754-1760 (2009).
Liao et al. Use of the CRISPR/Cas9 system as an intracellular defense against HIV-1 infection in human cells. Nature Communications 6:6413 (2015).
Liu et al. Recapitulation of premature ageing with iPSCs from Hutchinson-Gilford progeria syndrome. Nature 472:221-225 (2011).
Liu et al. Targeted gene correction of laminopathy-associated LMNA mutations in patient-specific iPSCs. Cell Stem Cell 8:688-694 (2011).
Madisen et al. A robust and high-throughput Cre reporting and characterization system for the whole mouse brain. Nat Neurosci 13:133-140 (2009).
Maresca et al. Obligate ligation-gated recombination (ObLiGaRe): custom-designed nuclease-mediated targeted integration through nonhomologous end joining. Genome Res 23:539-546 (2013).
Martinez et al. Successful non-surgical deep uterine transfer of porcine morulae after 24 hour culture in a chemically defined medium. PLoS One 9:e104696 (2014).
Matsunari et al. Blastocyst complementation generates exogenic pancreas in vivo in apancreatic cloned pigs. PNAS USA 110 (2013): 4557-4562.
Metsuyanim et al. Expression of Stem Cell Markers in the Human Fetal Kidney. PLoS One 4(8):e6709 (2009).
Miller et al. Construction and properties of retrovirus packaging cells based on gibbon ape leukemia virus. J Virol. 65(5):2220-2224 (1991).
Miller. Human gene therapy comes of age. Nature 357:455-460 (1992).
Mitani et al. Delivering therapeutic genes—matching approach and application Trends Biotechnol 11:162-166 (1993).
Mukai et al. Renal press-mediated transfection method for plasmid DNA and siRNA to the kidney. Biochem Biophys Res Commun 372:383-387 (2008).

(56) References Cited

OTHER PUBLICATIONS

Muzyczka. Adeno-associated virus (AAV) vectors: will they work? J. Clin. Invest. 94:1351 (1994).
Nabel et al. Direct gene transfer for immunotherapy and immunization Trends Biotechnol 11:211-217 (1993).
Nakade et al. Microhomology-mediated end-joining-dependent integration of donor DNA in cells and animals using TALENs and CRISPR/Cas9. Nat Commun 5:5560 (2014). 8 pages.
Orlando et al. Zinc-finger nuclease-driven targeted integration into mammalian genomes using donors with limited chromosomal homology. Nuc Acids Res 38(15):e152.
Panyam et al. Biodegradable nanoparticles for drug and gene delivery to cells and tissue. Adv Drug Deliv Rev. 64(Supp):61-71 (2012).
Parrish et al. Bovine in vitro fertilization with frozen-thawed semen. Theriogenology 25:591-600 (1986).
Parrish et al. Capacitation of bovine sperm by heparin. Biol Reprod 38:1171-1180 (1988).
PCT/US2017/042151 International Search Report and Written Opinion dated Oct. 27, 2017.
Petters et al. Culture of pig embryos. J Reprod Fertil Suppl 48:61-73 (1993).
Ramirez et al. Engineered zinc finger nickases induce homology-directed repair with reduced mutagenic effects. Nucl Acids Res 40(12):5560-5568 (2012).
Ranganathan et al., "Expansion of the CRISPR-Cas9 genome targeting space through the use of H 1 promoter-expressed guide RNAs," Nature Communications. DOI: 10.1038/ncomms5516. p. 1-8, 2014.
Rashid et al. Revisiting the flight of Icarus: making human organs from PSCs with large animal chimeras. Cell Stem Cell 15:406-409 (2014).
Remy et al. Gene transfer with a series of lipophilic DNA-binding molecules. Bioconjug Chem 5:647-654 (1994).
Ross et al. Polycomb gene expression and histone H3 lysine 27 trimethylation changes during bovine preimplantation development. Reprod 136:777-785 (2008).
Sakuma et al. MMEJ-assisted gene knock-in using TALENs and CRISPR-Cas9 with the PITCh systems. Nat Protocol 11(1):118-133 (2015).
Samulski et al. Helper-free stocks of recombinant adeno-associated viruses: normal integration does not require viral gene expression. J Virol. 63(9):3822-3828 (1989).
Sanjana et al. A transcription activator-like effector toolbox for genome engineering. Nature Protocols 7:171-192 (2012).
Sauvé et al. The relationship between full field electroretinogram and perimetry-like visual thresholds in RCS rats during photoreceptor degeneration and rescue by cell transplants. Vision Res 44:9-18 (2004).
Scharenberg et al. Genome engineering with TAL-effector nucleases and alternative modular nuclease technologies. Curr Gene Ther 13(4):291-303 (2013).
Segal. Bacteria herald a new era of gene editing. Life 2:e00563 (2013).

Singh et al., "Protein Engineering Approaches in the Post-Genomic Era," Curr Protein Pept Sci. 18:1-11, 2017.
Sommnerfelt et al. Localization of the receptor gene for type D simian retroviruses on human chromosome 19. J Virol 64(12):6214-6220 (1990).
Suzuki et al. In vivo genome editing via CRISPR/Cas9 mediated homology-independent targeted integration. Nature 540(7631):144-149 (2016).
Takahashi et al. Transferring genes into cultured mammalian embryos by electroporation. Dev Growth Differ 50:485-497 (2008).
Talaulikar et al. DNA amplification from formalin-fixed decalcified paraffin-embedded bone marrow trephine specimens: does the duration of storage matter? Pathology 40:702-706 (2008).
Tratschin et al. A human parvovirus, adeno-associated virus, as a eucaryotic vector: transient expression and encapsidation of the procaryotic gene for chloramphenicol acetyltransferase. Mol Cell Biol 4:2072-2081 (1984).
Tratschin et al. Adeno-associated virus vector for high-frequency integration, expression, and rescue of genes in mammalian cells. Mol Cell Biol 5(11):3251-3260 (1985).
Urnov et al. Genome editing with engineered zinc finger nucleases. Nature Reviews Genetics 11:636-646 (2010).
U.S. Appl. No. 15/406,606 Office Action dated Apr. 1, 2019.
Van Brunt. Molecular farming: Transgenic animals as bio-reactors. Biotechnology 6(10):1149-1154 (1988).
Vigne et al. Third-generation adenovectors for gene therapy. Restor Neurol Neurosci 8(1):35-36 (1995).
West et al. Gene expression in adeno-associated virus vectors: the effects of chimeric mRNA structure, helper virus, and adenovirus VA1 RNA. Virology 160(1):38-47 (1987).
Wilson et al. Formation of infectious hybrid virions with gibbon ape leukemia virus and human T-cell leukemia virus retroviral envelope glycoproteins and the gag and pol proteins of Moloney murine leukemia virus. J Virol 63(5):2374-2378 (1989).
Wu et al. An alternative pluripotent state confers interspecies chimaeric competency. Nature 521:316-321(2015).
Wu et al. Dynamic Pluripotent Stem Cell States and Their Applications. Cell Stem Cell 17:509-525 (2015).
Wu et al. The intracellular mobility of nuclear import receptors and NLS cargoes. Biophys. J. 96:3840-3849 (2009).
Xia et al. Directed differentiation of human pluripotent cells to ureteric bud kidney progenitor-like cells. Nature Cell Biology 15:1507-1515 (2013).
Yokoo et al. Xenobiotic kidney organogenesis from human mesenchymal stem cells using a growing rodent embryo. JASN 17:1026-1034 (2006).
Yoshioka et al. Production of piglets from in vitro-produced embryos following non-surgical transfer. Anim Reprod Sci 131(1-2):23-29 (2012).
Yu et al. Progress towards gene therapy for HIV infection. Gene Ther 1(1):13-26 (1994).
Yuri et al. Maintenance of Mouse Nephron Progenitor Cells in Aggregates with Gamma-Secretase Inhibitor. PLoS One 10(6):e0129242 (2015).
Zhang et al., "Propagated Perturbations from a Peripheral Mutation Show Interactions Supporting WW Domain Thermostability," Structure 26:1474-1485, 2018.

FIG. 4G
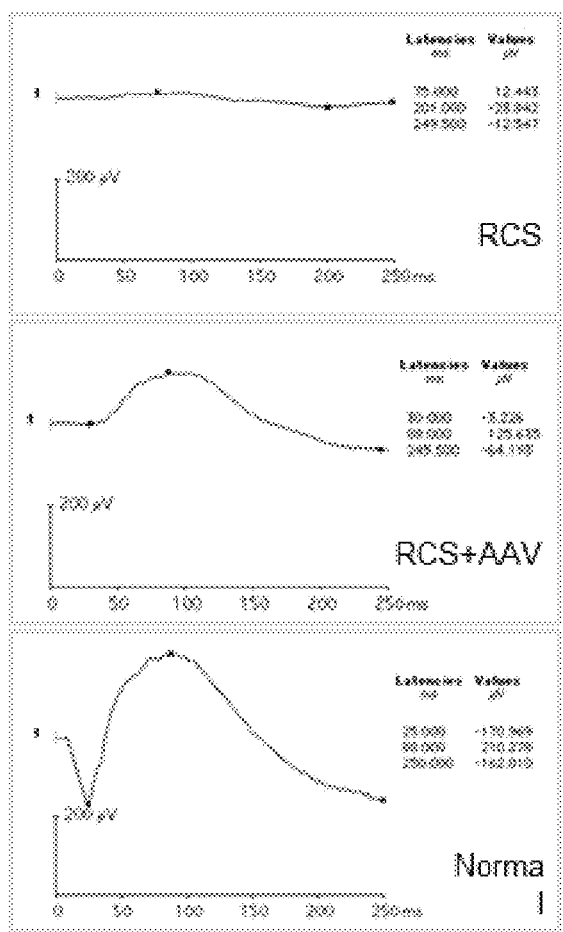
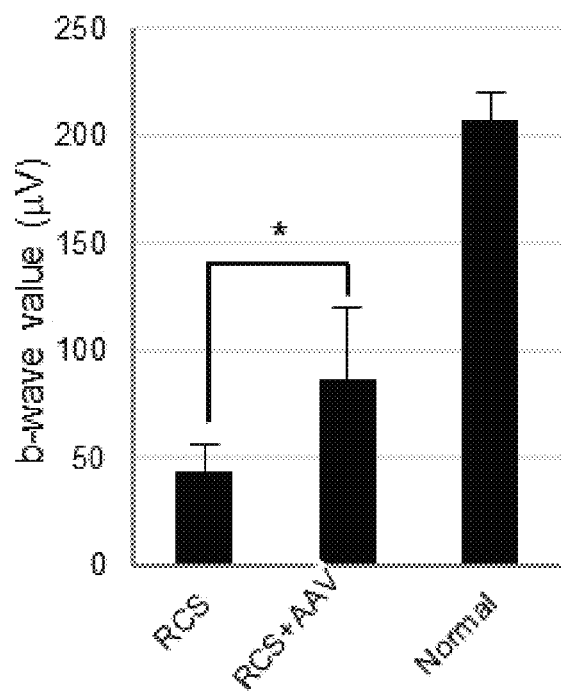

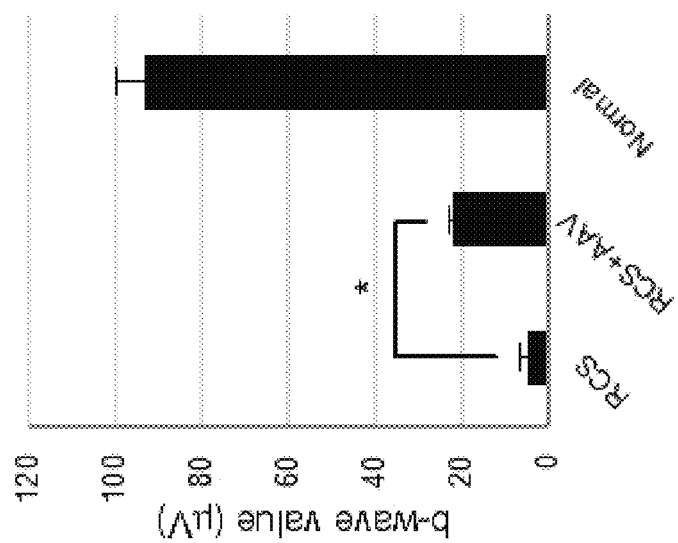
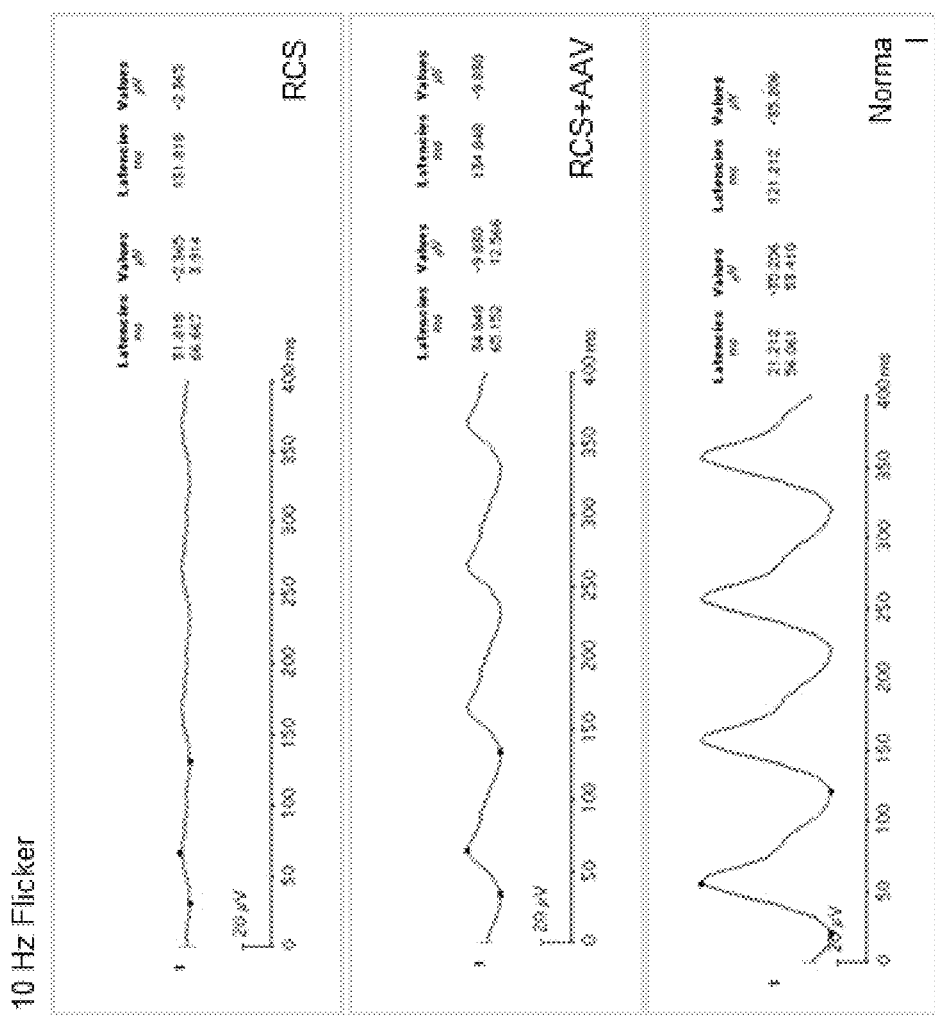
FIG. 4H

FIG. 5F
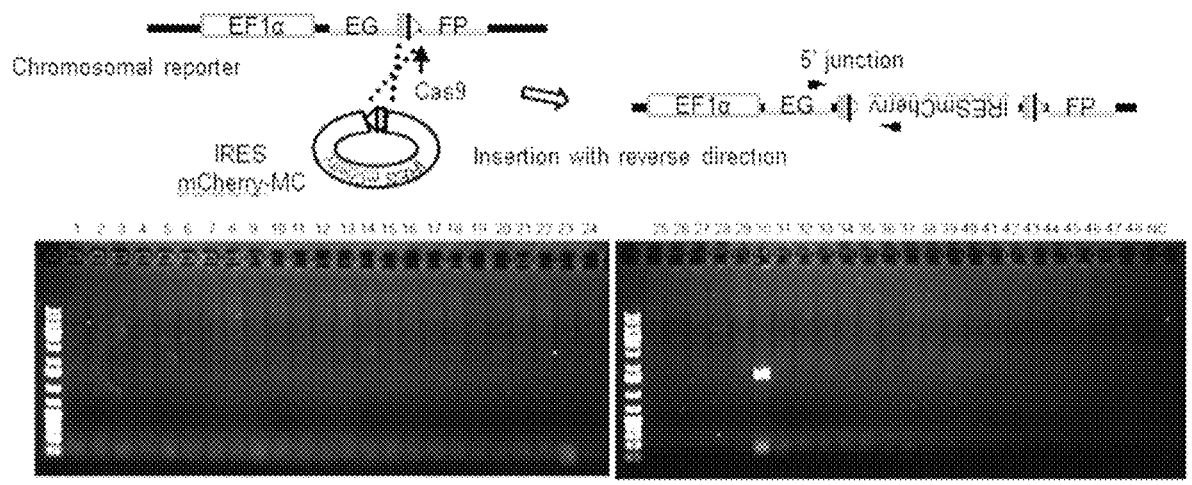

FIG. 13

| # | chromosome | position | sequence | PAM | total read depth | # of indel (%) |
|---|---|---|---|---|---|---|
| On | chr6 | | GAGGAACTTCTTAGGGCCCGCGG | CGG | 717,296 | 4.2618 |
| OTS1 | chr13 | 9534141 | CAGGAACTTCTTAGGTCCCGTGG | TGG | 825,966 | 0.0115 |
| OTS2 | chr14 | 85157555 | CGGAAACATCTTAGGGCCCGGGG | GGG | 455,049 | 0.0147 |
| OTS3 | chr2 | 74925639 | GGAGTACTTCTTAGGGCCCACAG | CAG | 407,292 | 0.0152 |
| OTS4 | chr15 | 69159526 | CAGGAACATATTAGGGCCCAGGG | GGG | 364,310 | 0.0159 |
| OTS5 | chr12 | 100704049 | CAGGAACATGTTAGGGTCCGAGG | AGG | 980,881 | 0.0114 |
| OTS6 | chrX | 91969928 | CAGGAACGTGTTCGGGCCCGCGG | CGG | 551,434 | 0.0000 |
| OTS7 | chrX | 92043584 | CAGGAACGTGTTCGGGCCCGCGG | CGG | 551,434 | 0.0000 |
| OTS8 | chr10 | 17440682 | CAGGAACTTCTTAGTGCCCTAAG | AAG | 524,379 | 0.0147 |
| OTS9 | chr18 | 25702486 | GTGGACCTTTCAGGGCCCGTGG | TGG | 575,965 | 0.0325 |
| OTS10 | chr18 | 9212447 | GAGGCCCCTCTTCGGGCCCGGAG | GAG | 484,996 | 0.0115 |
| OTS11 | chr14 | 46862821 | GTGGAGCATCTTAGGGCCAGTGG | TGG | 745,785 | 0.0126 |
| OTS12 | chr12 | 31652981 | GAGCAACAACTTAGGGCCTGCAG | CAG | 352,693 | 0.0139 |

FIG. 16J
Kidney (Day 118)
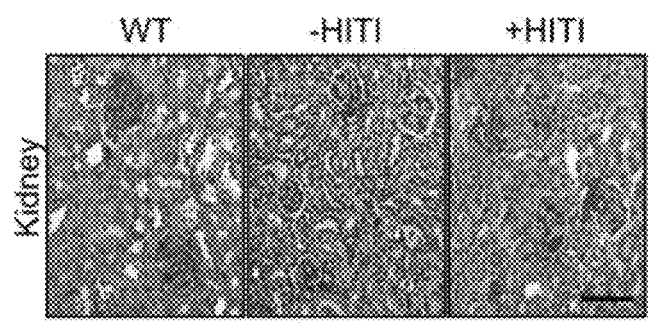
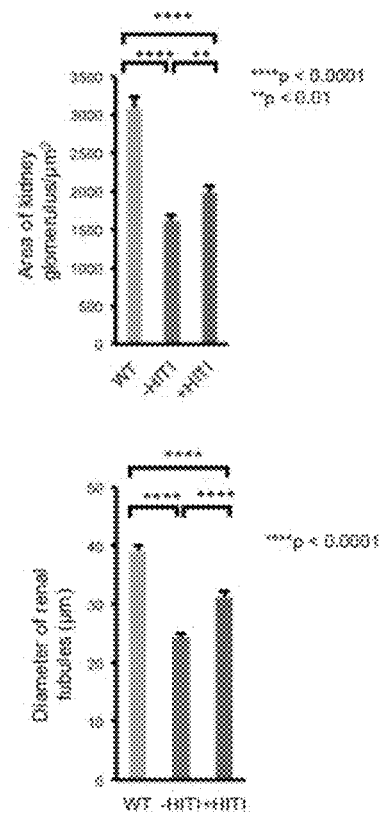
FIG. 16K
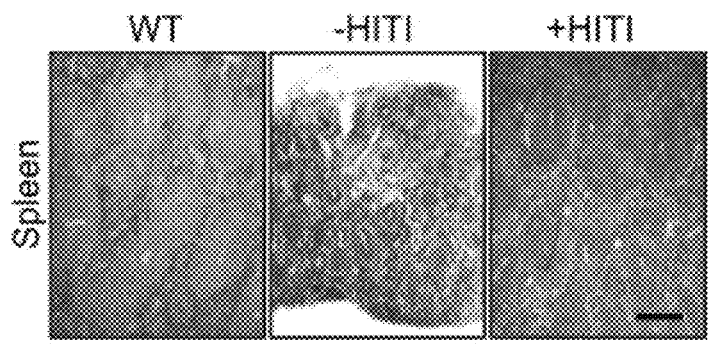
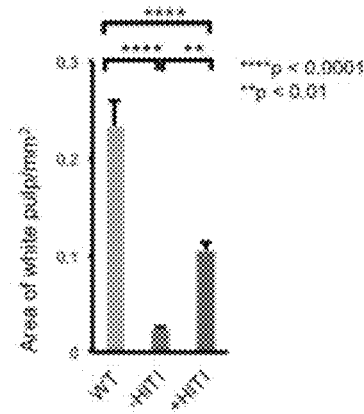

SEQUENCE LISTING

```
Sequence total quantity: 103
SEQ ID NO: 1            moltype = DNA  length = 56
FEATURE                 Location/Qualifiers
misc_feature            1..56
                        note = illustrative sequence containing an exemplary Cas9
                        cutting site
source                  1..56
                        mol_type = other DNA
                        organism = synthetic construct
SEQUENCE: 1
ggaatcggaa gcccaggggc ccaagtgaag ttgctcgcag ctggggtgtg gggcca          56

SEQ ID NO: 2            moltype = DNA  length = 58
FEATURE                 Location/Qualifiers
misc_feature            1..58
                        note = an aspect of an exemplary genome sequence
source                  1..58
                        mol_type = other DNA
                        organism = synthetic construct
SEQUENCE: 2
aaggacgacg gcaactacaa gacctaagct ctcgagatta ccctgttatc cctaagct       58

SEQ ID NO: 3            moltype = DNA  length = 58
FEATURE                 Location/Qualifiers
misc_feature            1..58
                        note = illustrative aspect of the IRESmCherry-1c plasmid,
                        the IRESmCherry-2c plasmid, and the IRESmCherry-MC plasmid
source                  1..58
                        mol_type = other DNA
                        organism = synthetic construct
SEQUENCE: 3
cccttgtcga ccagggtaat ctcgagagct taggtaaagc ggccgcgtcg acgggccc       58

SEQ ID NO: 4            moltype = DNA  length = 58
FEATURE                 Location/Qualifiers
misc_feature            1..58
                        note = exemplary 5' junction site sequence following
                        IRESmCherry knock-in
source                  1..58
                        mol_type = other DNA
                        organism = synthetic construct
SEQUENCE: 4
aaggacgacg gcaactacaa gacctaagct taggtaaagc ggccgcgtcg acgggccc       58

SEQ ID NO: 5            moltype = DNA  length = 124
FEATURE                 Location/Qualifiers
misc_feature            1..124
                        note = exemplary 5' junction site sequence following
```

```
                         IRESmCherry knock-in
variation                26..92
                         note = a, c, t, g, unknown or other
source                   1..124
                         mol_type = other DNA
                         organism = synthetic construct
SEQUENCE: 5
aaggacgacg gcaactacaa gacctnnnnn nnnnnnnnnn nnnnnnnnnn nnnnnnnnnn    60
nnnnnnnnnn nnnnnnnnnn nnnnnnnnnn nnaacttagg taaagcggcc gcgtcgacgg   120
gccc                                                                124

SEQ ID NO: 6             moltype = DNA   length = 58
FEATURE                  Location/Qualifiers
misc_feature             1..58
                         note = exemplary 3' junction site sequence following
                         IRESmCherry knock-in
source                   1..58
                         mol_type = other DNA
                         organism = synthetic construct
SEQUENCE: 6
cccttgtcga ccagggtaat ctcgagagct ctcgagatta ccctgttatc cctaagct     58

SEQ ID NO: 7             moltype = DNA   length = 59
FEATURE                  Location/Qualifiers
misc_feature             1..59
                         note = exemplary 3' junction site sequence following
                         IRESmCherry knock-in
source                   1..59
                         mol_type = other DNA
                         organism = synthetic construct
SEQUENCE: 7
cccttgtcga ccagggtaat ctcgagagtc tctcgagatt accctgttat cctaagct     59

SEQ ID NO: 8             moltype = DNA   length = 112
FEATURE                  Location/Qualifiers
misc_feature             1..112
                         note = exemplary 3' junction site sequence following
                         IRESmCherry knock-in
variation                25..83
                         note = a, c, t, g, unknown or other
source                   1..112
                         mol_type = other DNA
                         organism = synthetic construct
SEQUENCE: 8
cccttgtcga ccagggtaat ctccnnnnnn nnnnnnnnnn nnnnnnnnnn nnnnnnnnnn    60
nnnnnnnnnn nnnnnnnnnn nnntctcgag attaccctgt tatccctaag ct           112

SEQ ID NO: 9             moltype = DNA   length = 59
FEATURE                  Location/Qualifiers
misc_feature             1..59
                         note = exemplary 5' junction site sequence following
                         IRESmCherry knock-in
source                   1..59
                         mol_type = other DNA
                         organism = synthetic construct
SEQUENCE: 9
aaggacgacg gcaactacaa gacctaaggc ttaggtaaag cggccgcgtc gacgggccc    59

SEQ ID NO: 10            moltype = DNA   length = 59
FEATURE                  Location/Qualifiers
misc_feature             1..59
                         note = an exemplary 5' junction site sequence following
                         IRESmCherry knock-in
source                   1..59
                         mol_type = other DNA
                         organism = synthetic construct
SEQUENCE: 10
aaggacgacg gcaactacaa gacctaagcc ttaggtaaag cggccgcgtc gacgggccc    59

SEQ ID NO: 11            moltype = DNA   length = 58
FEATURE                  Location/Qualifiers
misc_feature             1..58
                         note = illustrative aspect of the IRESmCherry-2c plasmid
source                   1..58
                         mol_type = other DNA
                         organism = synthetic construct
SEQUENCE: 11
ttatggagat ccagggtaat ctcgagagct taggatatc catcacactg gcggccgc      58
```

| | | |
|---|---|---|
| SEQ ID NO: 12 | moltype = DNA length = 58 | |
| FEATURE | Location/Qualifiers | |
| misc_feature | 1..58 note = exemplary 3' junction site sequence following IRESmCherry knock-in | |
| source | 1..58 mol_type = other DNA organism = synthetic construct | |

SEQUENCE: 12
ttatggagat ccagggtaat ctcgagagct ctcgagatta ccctgttatc cctaagct       58

| | | |
|---|---|---|
| SEQ ID NO: 13 | moltype = DNA length = 57 | |
| FEATURE | Location/Qualifiers | |
| misc_feature | 1..57 note = exemplary 3' junction site sequence following IRESmCherry knock-in | |
| source | 1..57 mol_type = other DNA organism = synthetic construct | |

SEQUENCE: 13
ttatggagat ccagggtaat ctcgagagtc tcgagattac cctgttatcc ctaagct        57

| | | |
|---|---|---|
| SEQ ID NO: 14 | moltype = DNA length = 54 | |
| FEATURE | Location/Qualifiers | |
| misc_feature | 1..54 note = exemplary 3' junction site sequence following IRESmCherry knock-in | |
| source | 1..54 mol_type = other DNA organism = synthetic construct | |

SEQUENCE: 14
ttatggagat ccagggtaat ctcgagagcg agattaccct gttatcccta agct           54

| | | |
|---|---|---|
| SEQ ID NO: 15 | moltype = DNA length = 36 | |
| FEATURE | Location/Qualifiers | |
| misc_feature | 1..36 note = exemplary 3' junction site sequence following IRESmCherry knock-in | |
| source | 1..36 mol_type = other DNA organism = synthetic construct | |

SEQUENCE: 15
ttatggagat ccagggtaat ctcgagagcc taagct                               36

| | | |
|---|---|---|
| SEQ ID NO: 16 | moltype = DNA length = 38 | |
| FEATURE | Location/Qualifiers | |
| misc_feature | 1..38 note = exemplary 3' junction site sequence following IRESmCherry knock-in | |
| source | 1..38 mol_type = other DNA organism = synthetic construct | |

SEQUENCE: 16
ttatggagat ccagggatta ccctgttatc cctaagct                             38

| | | |
|---|---|---|
| SEQ ID NO: 17 | moltype = DNA length = 43 | |
| FEATURE | Location/Qualifiers | |
| misc_feature | 1..43 note = exemplary 5' junction site sequence following IRESmCherry knock-in | |
| source | 1..43 mol_type = other DNA organism = synthetic construct | |

SEQUENCE: 17
aaggacgacg gcaactacaa gacctaagtt atgtatgatg tgc                       43

| | | |
|---|---|---|
| SEQ ID NO: 18 | moltype = DNA length = 55 | |
| FEATURE | Location/Qualifiers | |
| misc_feature | note = aspect of an exemplary genome sequence | |
| source | 1..55 mol_type = other DNA organism = synthetic construct | |

SEQUENCE: 18
gacgacggca actacaagac ctaagctctc gagattaccc tgttatccct aagct          55

| | | |
|---|---|---|
| SEQ ID NO: 19 | moltype = DNA length = 55 | |
| FEATURE | Location/Qualifiers | |
| misc_feature | 1..55 | |

```
                        note = illustrative aspect of the IRESmCherry-MC plasmid
source                  1..55
                        mol_type = other DNA
                        organism = synthetic construct
SEQUENCE: 19
cgtcgacgcg gccgctttac ctaagctctc gagattaccc tggtcgacaa gggcg           55

SEQ ID NO: 20           moltype = DNA   length = 55
FEATURE                 Location/Qualifiers
misc_feature            1..55
                        note = example showing an expected directional sequence
                         following HITI
source                  1..55
                        mol_type = other DNA
                        organism = synthetic construct
SEQUENCE: 20
gacgacggca actacaagac ctaagctctc gagattaccc tggtcgacaa gggcg           55

SEQ ID NO: 21           moltype = DNA   length = 45
FEATURE                 Location/Qualifiers
misc_feature            1..45
                        note = exemplary sequence showing insertion in the reverse
                         direction
source                  1..45
                        mol_type = other DNA
                        organism = synthetic construct
SEQUENCE: 21
gacgacggca actacaagac ctaagtaccc tggtcgacaa gggcg                      45

SEQ ID NO: 22           moltype = DNA   length = 62
FEATURE                 Location/Qualifiers
misc_feature            1..62
                        note = aspect of the Tubb3 gene locus
source                  1..62
                        mol_type = other DNA
                        organism = synthetic construct
SEQUENCE: 22
cgaggaatcg gaagcccagg ggcccaagtg aagttgctcg cagctggggt gtggggccaa      60
gt                                                                    62

SEQ ID NO: 23           moltype = DNA   length = 62
FEATURE                 Location/Qualifiers
misc_feature            1..62
                        note = illustrative aspect of the Tubb3-2c plasmid
source                  1..62
                        mol_type = other DNA
                        organism = synthetic construct
SEQUENCE: 23
gcggccaagc tagctgcgag caacttcact tgggctggcc gctgcaatgg tgagcaaggg      60
cg                                                                    62

SEQ ID NO: 24           moltype = DNA   length = 62
FEATURE                 Location/Qualifiers
misc_feature            1..62
                        note = exemplary 5' junction site sequence following GFP
                         knock-in
source                  1..62
                        mol_type = other DNA
                        organism = synthetic construct
SEQUENCE: 24
cgaggaatcg gaagcccagg ggcccaagct tgggctggcc gctgcaatgg tgagcaaggg      60
cg                                                                    62

SEQ ID NO: 25           moltype = DNA   length = 61
FEATURE                 Location/Qualifiers
misc_feature            1..61
                        note = exemplary 5' junction site sequence following GFP
                         knock-in
source                  1..61
                        mol_type = other DNA
                        organism = synthetic construct
SEQUENCE: 25
cgaggaatcg gaagcccagg ggcccaactt gggctggccg ctgcaatggt gagcaagggc      60
g                                                                     61

SEQ ID NO: 26           moltype = DNA   length = 61
FEATURE                 Location/Qualifiers
misc_feature            1..61
                        note = illustrative aspect of the Tubb3-2c plasmid
```

```
source                  1..61
                        mol_type = other DNA
                        organism = synthetic construct
SEQUENCE: 26
caaactcatc aagctgcgag caacttcact tggggatccg tcgaccgatg cccttgagag    60
c                                                                    61

SEQ ID NO: 27           moltype = DNA   length = 61
FEATURE                 Location/Qualifiers
misc_feature            1..61
                        note = aspect of the Tubb3 gene locus
source                  1..61
                        mol_type = other DNA
                        organism = synthetic construct
SEQUENCE: 27
cgaggaatcg gaagcccagg ggcccaagtg aagttgctcg cagctggggt gtggggccaa    60
g                                                                    61

SEQ ID NO: 28           moltype = DNA   length = 61
FEATURE                 Location/Qualifiers
misc_feature            1..61
                        note = exemplary 3' junction site sequence following GFP
                          knock-in
source                  1..61
                        mol_type = other DNA
                        organism = synthetic construct
SEQUENCE: 28
caaactcatc aagctgcgag caacttcatg aagttgctcg cagctggggt gtggggccaa    60
g                                                                    61

SEQ ID NO: 29           moltype = DNA   length = 62
FEATURE                 Location/Qualifiers
misc_feature            1..62
                        note = illustrative aspect of the Tubb3-MC plasmid
source                  1..62
                        mol_type = other DNA
                        organism = synthetic construct
SEQUENCE: 29
gcgcgactat aagctgcgag caacttcact tgggtatgcc ggcggtagcg ctgtgagcaa    60
gg                                                                   62

SEQ ID NO: 30           moltype = DNA   length = 62
FEATURE                 Location/Qualifiers
misc_feature            1..62
                        note = exemplary 5' junction site sequence following GFP
                          knock-in
source                  1..62
                        mol_type = other DNA
                        organism = synthetic construct
SEQUENCE: 30
cgaggaatcg gaagcccagg ggcccaagct tgggtatgcc ggcggtagcg ctgtgagcaa    60
gg                                                                   62

SEQ ID NO: 31           moltype = DNA   length = 53
FEATURE                 Location/Qualifiers
misc_feature            1..53
                        note = exemplary 5' junction site sequence following GFP
                          knock-in
source                  1..53
                        mol_type = other DNA
                        organism = synthetic construct
SEQUENCE: 31
cgaggaatcg gaagcccagg ggcccaaggc cggcggtagc gctgtgagca agg            53

SEQ ID NO: 32           moltype = DNA   length = 62
FEATURE                 Location/Qualifiers
misc_feature            1..62
                        note = exemplary 3' junction site sequence following GFP
                          knock-in
source                  1..62
                        mol_type = other DNA
                        organism = synthetic construct
SEQUENCE: 32
gcgcgactat aagctgcgag caacttcatg aagttgctcg cagctggggt gtggggccaa    60
gt                                                                   62

SEQ ID NO: 33           moltype = DNA   length = 42
FEATURE                 Location/Qualifiers
misc_feature            1..42
```

```
                        note = exemplary 3' junction site sequence following GFP
                            knock-in
source                  1..42
                        mol_type = other DNA
                        organism = synthetic construct
SEQUENCE: 33
gcgcgacttg aagttgctcg cagctggggt gtggggccaa gt                            42

SEQ ID NO: 34           moltype = DNA  length = 35
FEATURE                 Location/Qualifiers
misc_feature            1..35
                        note = exemplary 3' junction site sequence following GFP
                            knock-in
source                  1..35
                        mol_type = other DNA
                        organism = synthetic construct
SEQUENCE: 34
gcgcgattgc tcgcagctgg ggtgtggggc caagt                                    35

SEQ ID NO: 35           moltype = DNA  length = 62
FEATURE                 Location/Qualifiers
misc_feature            1..62
                        note = aspect of the Tubb3 gene locus
source                  1..62
                        mol_type = other DNA
                        organism = synthetic construct
SEQUENCE: 35
ggaggagtcg gaggcccagg gccccaagtg aagctgctcg cagctggagt gagaggcagg         60
tg                                                                        62

SEQ ID NO: 36           moltype = DNA  length = 62
FEATURE                 Location/Qualifiers
misc_feature            1..62
                        note = an illustrative aspect of the hTUBB3-1c plasmid and
                            the hTUBB3-2c plasmid
source                  1..62
                        mol_type = other DNA
                        organism = synthetic construct
SEQUENCE: 36
tggccggtac cagctgcgag cagcttcact tgggtatgcc ggcggtagcg ctgtgagcaa         60
gg                                                                        62

SEQ ID NO: 37           moltype = DNA  length = 62
FEATURE                 Location/Qualifiers
misc_feature            1..62
                        note = exemplary 5' junction site sequence following GFP
                            knock-in
source                  1..62
                        mol_type = other DNA
                        organism = synthetic construct
SEQUENCE: 37
ggaggagtcg gaggcccagg gccccaagct tgggtatgcc ggcggtagcg ctgtgagcaa         60
gg                                                                        62

SEQ ID NO: 38           moltype = DNA  length = 34
FEATURE                 Location/Qualifiers
misc_feature            1..34
                        note = exemplary 5' junction site sequence following GFP
                            knock-in
source                  1..34
                        mol_type = other DNA
                        organism = synthetic construct
SEQUENCE: 38
ggaggagtcg ccggcggtag cgctgtgagc aagg                                     34

SEQ ID NO: 39           moltype = DNA  length = 59
FEATURE                 Location/Qualifiers
misc_feature            1..59
                        note = exemplary 5' junction site sequence following GFP
                            knock-in
source                  1..59
                        mol_type = other DNA
                        organism = synthetic construct
SEQUENCE: 39
ggaggagtcg gaggcccagg gccccttgg gtatgccggc ggtagcgctg tgagcaagg           59

SEQ ID NO: 40           moltype = DNA  length = 55
FEATURE                 Location/Qualifiers
misc_feature            1..55
```

```
                            note = exemplary 5' junction site sequence following GFP
                               knock-in
source                      1..55
                            mol_type = other DNA
                            organism = synthetic construct
SEQUENCE: 40
ggaggagtcg gaggcccagg gcccgggtat gccggcggta gcgctgtgag caagg          55

SEQ ID NO: 41               moltype = DNA   length = 54
FEATURE                     Location/Qualifiers
misc_feature                1..54
                            note = exemplary 5' junction site sequence following GFP
                               knock-in
source                      1..54
                            mol_type = other DNA
                            organism = synthetic construct
SEQUENCE: 41
ggaggagtcg gaggcccagg gccccaagcg ccggcggtag cgctgtgagc aagg           54

SEQ ID NO: 42               moltype = DNA   length = 41
FEATURE                     Location/Qualifiers
misc_feature                1..41
                            note = exemplary 5' junction site sequence following GFP
                               knock-in
source                      1..41
                            mol_type = other DNA
                            organism = synthetic construct
SEQUENCE: 42
ggaggagctt gggtatgccg gcggtagcgc tgtgagcaag g                         41

SEQ ID NO: 43               moltype = DNA   length = 32
FEATURE                     Location/Qualifiers
misc_feature                1..32
                            note = exemplary 5' junction site sequence following GFP
                               knock-in
source                      1..32
                            mol_type = other DNA
                            organism = synthetic construct
SEQUENCE: 43
ggaggagtcg ggcggtagcg ctgtgagcaa gg                                   32

SEQ ID NO: 44               moltype = DNA   length = 29
FEATURE                     Location/Qualifiers
misc_feature                1..29
                            note = exemplary 5' junction site sequence following GFP
                               knock-in
source                      1..29
                            mol_type = other DNA
                            organism = synthetic construct
SEQUENCE: 44
ggaggagtcg gaggcccagg tgagcaagg                                       29

SEQ ID NO: 45               moltype = DNA   length = 60
FEATURE                     Location/Qualifiers
misc_feature                1..60
                            note = exemplary 5' junction site sequence following GFP
                               knock-in
source                      1..60
                            mol_type = other DNA
                            organism = synthetic construct
SEQUENCE: 45
ggaggagtcg gaggcccagg gccccaagtg ggtatgccgg cggtagcgct gtgagcaagg     60

SEQ ID NO: 46               moltype = DNA   length = 45
FEATURE                     Location/Qualifiers
misc_feature                1..45
                            note = exemplary 5' junction site sequence following GFP
                               knock-in
source                      1..45
                            mol_type = other DNA
                            organism = synthetic construct
SEQUENCE: 46
ggaggagtcg gaggcccagg gccggcggta gcgctgtgag caagg                     45

SEQ ID NO: 47               moltype = DNA   length = 31
FEATURE                     Location/Qualifiers
misc_feature                1..31
                            note = exemplary 5' junction site sequence following GFP
                               knock-in
```

```
source                 1..31
                       mol_type = other DNA
                       organism = synthetic construct
SEQUENCE: 47
ggaggagtcg gaggcccagg gcgaggagct g                              31

SEQ ID NO: 48          moltype = DNA  length = 62
FEATURE                Location/Qualifiers
misc_feature           1..62
                       note = illustrative aspect of the AAV-mTubb3 vector
source                 1..62
                       mol_type = other DNA
                       organism = synthetic construct
SEQUENCE: 48
ggcgttttaaa cggctgcgag caacttcact tgggtatgcc ggcggtagcg ctgtgagcaa    60
gg                                                                   62

SEQ ID NO: 49          moltype = DNA  length = 61
FEATURE                Location/Qualifiers
misc_feature           1..61
                       note = exemplary 5' junction site sequence following GFP
                         knock-in
source                 1..61
                       mol_type = other DNA
                       organism = synthetic construct
SEQUENCE: 49
cgaggaatcg gaagcccagg ggcccaactt gggtatgccg gcggtagcgc tgtgagcaag    60
g                                                                   61

SEQ ID NO: 50          moltype = DNA  length = 61
FEATURE                Location/Qualifiers
misc_feature           1..61
                       note = exemplary 5' junction site sequence following GFP
                         knock-in
source                 1..61
                       mol_type = other DNA
                       organism = synthetic construct
SEQUENCE: 50
cgaggaatcg gaagcccagg ggcccaagtt gggtatgccg gcggtagcgc tgtgagcaag    60
g                                                                   61

SEQ ID NO: 51          moltype = DNA  length = 63
FEATURE                Location/Qualifiers
misc_feature           1..63
                       note = exemplary 5' junction site sequence following GFP
                         knock-in
source                 1..63
                       mol_type = other DNA
                       organism = synthetic construct
SEQUENCE: 51
cgaggaatcg gaagcccagg ggcccaaggc ttgggtatgc cggcggtagc gctgtgagca    60
agg                                                                 63

SEQ ID NO: 52          moltype = DNA  length = 63
FEATURE                Location/Qualifiers
misc_feature           1..63
                       note = exemplary 5' junction site sequence following GFP
                         knock-in
source                 1..63
                       mol_type = other DNA
                       organism = synthetic construct
SEQUENCE: 52
cgaggaatcg gaagcccagg ggcccaagac ttgggtatgc cggcggtagc gctgtgagca    60
agg                                                                 63

SEQ ID NO: 53          moltype = DNA  length = 63
FEATURE                Location/Qualifiers
misc_feature           1..63
                       note = exemplary 5' junction site sequence following GFP
                         knock-in
source                 1..63
                       mol_type = other DNA
                       organism = synthetic construct
SEQUENCE: 53
cgaggaatcg gaagcccagg ggcccaagtc ttgggtatgc cggcggtagc gctgtgagca    60
agg                                                                 63

SEQ ID NO: 54          moltype = DNA  length = 59
FEATURE                Location/Qualifiers
```

```
misc_feature              1..59
                          note = exemplary 5' junction site sequence following GFP
                            knock-in
source                    1..59
                          mol_type = other DNA
                          organism = synthetic construct
SEQUENCE: 54
cgaggaatcg gaagcccagg ggccccttgg gtatgccggc ggtagcgctg tgagcaagg         59

SEQ ID NO: 55             moltype = DNA  length = 57
FEATURE                   Location/Qualifiers
misc_feature              1..57
                          note = exemplary 5' junction site sequence following GFP
                            knock-in
source                    1..57
                          mol_type = other DNA
                          organism = synthetic construct
SEQUENCE: 55
cgaggaatcg gaagcccagg ggcccaaggt atgccggcgg tagcgctgtg agcaagg           57

SEQ ID NO: 56             moltype = DNA  length = 52
FEATURE                   Location/Qualifiers
misc_feature              1..52
                          note = exemplary 5' junction site sequence following GFP
                            knock-in
source                    1..52
                          mol_type = other DNA
                          organism = synthetic construct
SEQUENCE: 56
cgaggaatcg gaagcccagg ggcccaagcc ggcggtagcg ctgtgagcaa gg                52

SEQ ID NO: 57             moltype = DNA  length = 61
FEATURE                   Location/Qualifiers
misc_feature              1..61
                          note = illustrative aspect of the AAV-mTubb3 vector
source                    1..61
                          mol_type = other DNA
                          organism = synthetic construct
SEQUENCE: 57
gctgtacaag tggctgcgag caacttcact tgggacgcgt aagctttgca aagatggata       60
a                                                                        61

SEQ ID NO: 58             moltype = DNA  length = 61
FEATURE                   Location/Qualifiers
misc_feature              1..61
                          note = exemplary 3' junction site sequence following GFP
                            knock-in
source                    1..61
                          mol_type = other DNA
                          organism = synthetic construct
SEQUENCE: 58
gctgtacaag tggctgcgag caacttcatg aagttgctcg cagctggggt gtggggccaa       60
g                                                                        61

SEQ ID NO: 59             moltype = DNA  length = 44
FEATURE                   Location/Qualifiers
misc_feature              1..44
                          note = exemplary 3' junction site sequence following GFP
                            knock-in
source                    1..44
                          mol_type = other DNA
                          organism = synthetic construct
SEQUENCE: 59
gctgtacaag tggctgcgag caacttcagg ggtgtggggc caag                         44

SEQ ID NO: 60             moltype = DNA  length = 44
FEATURE                   Location/Qualifiers
misc_feature              1..44
                          note = exemplary 3' junction site sequence following GFP
                            knock-in
source                    1..44
                          mol_type = other DNA
                          organism = synthetic construct
SEQUENCE: 60
gcgcgatcac atgaagttgc tcgcagctgg ggtgtggggc caag                         44

SEQ ID NO: 61             moltype = DNA  length = 108
FEATURE                   Location/Qualifiers
misc_feature              1..108
```

```
                              note = exemplary 3' junction site sequence following GFP
                                knock-in
variation                     24..75
                              note = a, c, t, g, unknown or other
source                        1..108
                              mol_type = other DNA
                              organism = synthetic construct
SEQUENCE: 61
gctgtacaag tggctgcgag caannnnnnn nnnnnnnnnn nnnnnnnnnn nnnnnnnnnn    60
nnnnnnnnnn nnnnntgaag ttgctcgcag ctggggtgtg gggccaag                108

SEQ ID NO: 62                 moltype = DNA  length = 62
FEATURE                       Location/Qualifiers
misc_feature                  1..62
                              note = aspect of the CAG promoter locus
source                        1..62
                              mol_type = other DNA
                              organism = synthetic construct
SEQUENCE: 62
ttggcaaaga attgatttga taccgcgggc cctaagaagt tcctattctc tagaaagtat    60
ag                                                                  62

SEQ ID NO: 63                 moltype = DNA  length = 62
FEATURE                       Location/Qualifiers
misc_feature                  1..62
                              note = illustrative aspect of the AAV-Ai14-GFP vector
source                        1..62
                              mol_type = other DNA
                              organism = synthetic construct
SEQUENCE: 63
gcgcgactat agaggaactt cttagggccc gcgggccacc atggtgagca agggcgagga    60
gc                                                                  62

SEQ ID NO: 64                 moltype = DNA  length = 62
FEATURE                       Location/Qualifiers
misc_feature                  1..62
                              note = exemplary 5' junction site sequence following
                                GFP-NLS knock-in
source                        1..62
                              mol_type = other DNA
                              organism = synthetic construct
SEQUENCE: 64
ttggcaaaga attgatttga taccgcggcc gcgggccacc atggtgagca agggcgagga    60
gc                                                                  62

SEQ ID NO: 65                 moltype = DNA  length = 56
FEATURE                       Location/Qualifiers
misc_feature                  1..56
                              note = exemplary 5' junction site sequence following
                                GFP-NLS knock-in
source                        1..56
                              mol_type = other DNA
                              organism = synthetic construct
SEQUENCE: 65
ttggcaaaga attgatttga taccgcgggc caccatggtg agcaagggcg aggagc        56

SEQ ID NO: 66                 moltype = DNA  length = 63
FEATURE                       Location/Qualifiers
misc_feature                  1..63
                              note = exemplary 5' junction site sequence following
                                GFP-NLS knock-in
source                        1..63
                              mol_type = other DNA
                              organism = synthetic construct
SEQUENCE: 66
ttggcaaaga attgatttga taccgcggac cgcgggccac catggtgagc aagggcgagg    60
agc                                                                 63

SEQ ID NO: 67                 moltype = DNA  length = 63
FEATURE                       Location/Qualifiers
misc_feature                  1..63
                              note = exemplary 5' junction site sequence following
                                GFP-NLS knock-in
source                        1..63
                              mol_type = other DNA
                              organism = synthetic construct
SEQUENCE: 67
ttggcaaaga attgatttga taccgcggcc cgcgggccac catggtgagc aagggcgagg    60
agc                                                                 63
```

```
SEQ ID NO: 68           moltype = DNA  length = 60
FEATURE                 Location/Qualifiers
misc_feature            1..60
                        note = exemplary 5' junction site sequence following
                         GFP-NLS knock-in
source                  1..60
                        mol_type = other DNA
                        organism = synthetic construct
SEQUENCE: 68
ttggcaaaga attgatttga taccgcgggc gggccaccat ggtgagcaag ggcgaggagc    60

SEQ ID NO: 69           moltype = DNA  length = 46
FEATURE                 Location/Qualifiers
misc_feature            1..46
                        note = exemplary 5' junction site sequence following
                         GFP-NLS knock-in
source                  1..46
                        mol_type = other DNA
                        organism = synthetic construct
SEQUENCE: 69
ttggcaaaga attgatttga taccatggtg agcaagggcg aggagc                  46

SEQ ID NO: 70           moltype = DNA  length = 42
FEATURE                 Location/Qualifiers
misc_feature            1..42
                        note = exemplary 5' junction site sequence following
                         GFP-NLS knock-in
source                  1..42
                        mol_type = other DNA
                        organism = synthetic construct
SEQUENCE: 70
ttggcaaaga attgatttga taccgcggca agggcgagga gc                      42

SEQ ID NO: 71           moltype = DNA  length = 41
FEATURE                 Location/Qualifiers
misc_feature            1..41
                        note = exemplary 5' junction site sequence following
                         GFP-NLS knock-in
source                  1..41
                        mol_type = other DNA
                        organism = synthetic construct
SEQUENCE: 71
ttggcaaaga attgatttga taccgcggaa gggcgaggag c                       41

SEQ ID NO: 72           moltype = DNA  length = 63
FEATURE                 Location/Qualifiers
misc_feature            1..63
                        note = exemplary 5' junction site sequence following
                         GFP-NLS knock-in
source                  1..63
                        mol_type = other DNA
                        organism = synthetic construct
SEQUENCE: 72
ttggcaaaga attgatttga taccgcgggc cgcgggccac catggtgagc aagggcgagg   60
agc                                                                 63

SEQ ID NO: 73           moltype = DNA  length = 62
FEATURE                 Location/Qualifiers
misc_feature            1..62
                        note = illustrative aspect of the AAV-Ai14-GFP vector
source                  1..62
                        mol_type = other DNA
                        organism = synthetic construct
SEQUENCE: 73
gggcgctctt cgaggaactt cttagggccc gcggacgcgt aagctttgca aagatggata   60
aa                                                                  62

SEQ ID NO: 74           moltype = DNA  length = 62
FEATURE                 Location/Qualifiers
misc_feature            1..62
                        note = exemplary 3' junction site sequence following
                         GFP-NLS knock-in
source                  1..62
                        mol_type = other DNA
                        organism = synthetic construct
SEQUENCE: 74
gggcgctctt cgaggaactt cttagggcgc cctaagaagt cctattctc tagaaagtat   60
ag                                                                  62
```

```
SEQ ID NO: 75          moltype = DNA   length = 63
FEATURE                Location/Qualifiers
misc_feature           1..63
                       note = exemplary 3' junction site sequence following
                         GFP-NLS knock-in
source                 1..63
                       mol_type = other DNA
                       organism = synthetic construct
SEQUENCE: 75
gggcgctctt cgaggaactt cttagggcgg ccctaagaag ttcctattct ctagaaagta  60
tag                                                                63

SEQ ID NO: 76          moltype = DNA   length = 60
FEATURE                Location/Qualifiers
misc_feature           1..60
                       note = exemplary 3' junction site sequence following
                         GFP-NLS knock-in
source                 1..60
                       mol_type = other DNA
                       organism = synthetic construct
SEQUENCE: 76
gggcgctctt cgaggaactt cttagggccc taagaagttc ctattctcta gaaagtatag  60

SEQ ID NO: 77          moltype = DNA   length = 59
FEATURE                Location/Qualifiers
misc_feature           1..59
                       note = exemplary 3' junction site sequence following
                         GFP-NLS knock-in
source                 1..59
                       mol_type = other DNA
                       organism = synthetic construct
SEQUENCE: 77
gggcgctctt cgaggaactt cttaggccct aagaagttcc tattctctag aaagtatag   59

SEQ ID NO: 78          moltype = DNA   length = 50
FEATURE                Location/Qualifiers
misc_feature           1..50
                       note = exemplary 3' junction site sequence following
                         GFP-NLS knock-in
source                 1..50
                       mol_type = other DNA
                       organism = synthetic construct
SEQUENCE: 78
gggcgctctt cgaggaaccc taagaagttc ctattctcta gaaagtatag              50

SEQ ID NO: 79          moltype = DNA   length = 31
FEATURE                Location/Qualifiers
misc_feature           1..31
                       note = exemplary 3' junction site sequence following
                         GFP-NLS knock-in
source                 1..31
                       mol_type = other DNA
                       organism = synthetic construct
SEQUENCE: 79
gggcgctctt cgaggaactt cttaggaact t                                  31

SEQ ID NO: 80          moltype = DNA   length = 48
FEATURE                Location/Qualifiers
misc_feature           1..48
                       note = exemplary 3' junction site sequence following
                         GFP-NLS knock-in
source                 1..48
                       mol_type = other DNA
                       organism = synthetic construct
SEQUENCE: 80
gggcgctctt cgatgcccta agaagttcct attctctaga aagtatag                48

SEQ ID NO: 81          moltype = DNA   length = 64
FEATURE                Location/Qualifiers
misc_feature           1..64
                       note = exemplary 3' junction site sequence following
                         GFP-NLS knock-in
source                 1..64
                       mol_type = other DNA
                       organism = synthetic construct
SEQUENCE: 81
gggcgctctt cgaggaactt cttagggcgc gccctaagaa gttcctattc tctagaaagt  60
atag                                                               64
```

-continued

```
SEQ ID NO: 82          moltype = DNA   length = 23
FEATURE                Location/Qualifiers
misc_feature           1..23
                       note = exemplary on-target sequence
source                 1..23
                       mol_type = other DNA
                       organism = synthetic construct
SEQUENCE: 82
gaggaacttc ttagggcccg cgg                                              23

SEQ ID NO: 83          moltype = DNA   length = 23
FEATURE                Location/Qualifiers
misc_feature           1..23
                       note = exemplary off-target sequence OTS1
source                 1..23
                       mol_type = other DNA
                       organism = synthetic construct
SEQUENCE: 83
caggaacttc ttaggtcccg tgg                                              23

SEQ ID NO: 84          moltype = DNA   length = 23
FEATURE                Location/Qualifiers
misc_feature           1..23
                       note = exemplary off-target sequence OTS2
source                 1..23
                       mol_type = other DNA
                       organism = synthetic construct
SEQUENCE: 84
cggaaacatc ttagggcccg ggg                                              23

SEQ ID NO: 85          moltype = DNA   length = 23
FEATURE                Location/Qualifiers
misc_feature           1..23
                       note = exemplary off-target sequence OTS3
source                 1..23
                       mol_type = other DNA
                       organism = synthetic construct
SEQUENCE: 85
ggagtacttc ttagggccca cag                                              23

SEQ ID NO: 86          moltype = DNA   length = 23
FEATURE                Location/Qualifiers
misc_feature           1..23
                       note = exemplary off-target sequence OTS4
source                 1..23
                       mol_type = other DNA
                       organism = synthetic construct
SEQUENCE: 86
caggaacata ttagggccca ggg                                              23

SEQ ID NO: 87          moltype = DNA   length = 23
FEATURE                Location/Qualifiers
misc_feature           1..23
                       note = exemplary off-target sequence OTS5
source                 1..23
                       mol_type = other DNA
                       organism = synthetic construct
SEQUENCE: 87
caggaacatg ttagggtccg agg                                              23

SEQ ID NO: 88          moltype = DNA   length = 23
FEATURE                Location/Qualifiers
misc_feature           1..23
                       note = exemplary off-target sequences OTS6 and OTS7
source                 1..23
                       mol_type = other DNA
                       organism = synthetic construct
SEQUENCE: 88
caggaacgtg ttcgggcccg cgg                                              23

SEQ ID NO: 89          moltype = DNA   length = 23
FEATURE                Location/Qualifiers
misc_feature           1..23
                       note = exemplary off-target sequence OTS8
source                 1..23
                       mol_type = other DNA
                       organism = synthetic construct
SEQUENCE: 89
```

```
caggaacttc ttagtgccct aag                                             23

SEQ ID NO: 90           moltype = DNA   length = 23
FEATURE                 Location/Qualifiers
misc_feature            1..23
                        note = exemplary off-target sequence OTS9
source                  1..23
                        mol_type = other DNA
                        organism = synthetic construct
SEQUENCE: 90
gtggaccttt tcagggcccg tgg                                             23

SEQ ID NO: 91           moltype = DNA   length = 23
FEATURE                 Location/Qualifiers
misc_feature            1..23
                        note = exemplary off-target sequence OTS10
source                  1..23
                        mol_type = other DNA
                        organism = synthetic construct
SEQUENCE: 91
gaggcccctc ttcgggcccg gag                                             23

SEQ ID NO: 92           moltype = DNA   length = 23
FEATURE                 Location/Qualifiers
misc_feature            1..23
                        note = exemplary off-target sequence OTS11
source                  1..23
                        mol_type = other DNA
                        organism = synthetic construct
SEQUENCE: 92
gtggagcatc ttagggccag tgg                                             23

SEQ ID NO: 93           moltype = DNA   length = 23
FEATURE                 Location/Qualifiers
misc_feature            1..23
                        note = exemplary off-target sequence OTS12
source                  1..23
                        mol_type = other DNA
                        organism = synthetic construct
SEQUENCE: 93
gagcaacaac ttagggcctg cag                                             23

SEQ ID NO: 94           moltype = DNA   length = 62
FEATURE                 Location/Qualifiers
misc_feature            1..62
                        note = aspect of the Mertk locus
source                  1..62
                        mol_type = other DNA
                        organism = synthetic construct
SEQUENCE: 94
tttgtgcctg tgcgtgtgtg cgccagcccc gttgcagtgg tcctcgctag ctgtcagtgg     60
gc                                                                    62

SEQ ID NO: 95           moltype = DNA   length = 62
FEATURE                 Location/Qualifiers
misc_feature            1..62
                        note = illustrative aspect of the AAV-rMertk vect
source                  1..62
                        mol_type = other DNA
                        organism = synthetic construct
SEQUENCE: 95
acgcccagct agaggaccac tgcaacgggg ctggccataa gacacatttc tccagtgaca     60
tg                                                                    62

SEQ ID NO: 96           moltype = DNA   length = 62
FEATURE                 Location/Qualifiers
misc_feature            1..62
                        note = exemplary 3' connection site sequence following
                         AAV-rMertk treatment
source                  1..62
                        mol_type = other DNA
                        organism = synthetic construct
SEQUENCE: 96
tttgtgcctg tgcgtgtgtg cgccagccgg ctggccataa gacacatttc tccagtgaca     60
tg                                                                    62

SEQ ID NO: 97           moltype = DNA   length = 40
FEATURE                 Location/Qualifiers
misc_feature            1..40
```

```
                        note = exemplary 3' connection site sequence following
                            AAV-rMertk treatment
source                  1..40
                        mol_type = other DNA
                        organism = synthetic construct
SEQUENCE: 97
tttgtgcctg tgcgtgtgtg cgccagccaa ttctggatga                                40

SEQ ID NO: 98           moltype = DNA   length = 24
FEATURE                 Location/Qualifiers
misc_feature            1..24
                        note = exemplary 3' connection site sequence following
                            AAV-rMertk treatment
source                  1..24
                        mol_type = other DNA
                        organism = synthetic construct
SEQUENCE: 98
aggggtgtt tctccagtga catg                                                  24

SEQ ID NO: 99           moltype = DNA   length = 364
FEATURE                 Location/Qualifiers
misc_feature            1..364
                        note = exemplary 3' junction site sequence following
                            IRESmCherry knock-in
variation               27..332
                        note = a, c, t, g, unknown or other
source                  1..364
                        mol_type = other DNA
                        organism = synthetic construct
SEQUENCE: 99
cccttgtcga ccagggtaat ctcgagnnnn nnnnnnnnnn nnnnnnnnnn nnnnnnnnnn          60
nnnnnnnnnn nnnnnnnnnn nnnnnnnnnn nnnnnnnnnn nnnnnnnnnn nnnnnnnnnn         120
nnnnnnnnnn nnnnnnnnnn nnnnnnnnnn nnnnnnnnnn nnnnnnnnnn nnnnnnnnnn         180
nnnnnnnnnn nnnnnnnnnn nnnnnnnnnn nnnnnnnnnn nnnnnnnnnn nnnnnnnnnn         240
nnnnnnnnnn nnnnnnnnnn nnnnnnnnnn nnnnnnnnnn nnnnnnnnnn nnnnnnnnnn         300
nnnnnnnnnn nnnnnnnnnn nnnnnnnnnn nnagctctcg agattaccct gttatcccta         360
agct                                                                      364

SEQ ID NO: 100          moltype = DNA   length = 637
FEATURE                 Location/Qualifiers
misc_feature            1..637
                        note = exemplary 3' junction site sequence following
                            IRESmCherry knock-in
variation               27..605
                        note = a, c, t, g, unknown or other
source                  1..637
                        mol_type = other DNA
                        organism = synthetic construct
SEQUENCE: 100
cccttgtcga ccagggtaat ctcgagnnnn nnnnnnnnnn nnnnnnnnnn nnnnnnnnnn          60
nnnnnnnnnn nnnnnnnnnn nnnnnnnnnn nnnnnnnnnn nnnnnnnnnn nnnnnnnnnn         120
nnnnnnnnnn nnnnnnnnnn nnnnnnnnnn nnnnnnnnnn nnnnnnnnnn nnnnnnnnnn         180
nnnnnnnnnn nnnnnnnnnn nnnnnnnnnn nnnnnnnnnn nnnnnnnnnn nnnnnnnnnn         240
nnnnnnnnnn nnnnnnnnnn nnnnnnnnnn nnnnnnnnnn nnnnnnnnnn nnnnnnnnnn         300
nnnnnnnnnn nnnnnnnnnn nnnnnnnnnn nnnnnnnnnn nnnnnnnnnn nnnnnnnnnn         360
nnnnnnnnnn nnnnnnnnnn nnnnnnnnnn nnnnnnnnnn nnnnnnnnnn nnnnnnnnnn         420
nnnnnnnnnn nnnnnnnnnn nnnnnnnnnn nnnnnnnnnn nnnnnnnnnn nnnnnnnnnn         480
nnnnnnnnnn nnnnnnnnnn nnnnnnnnnn nnnnnnnnnn nnnnnnnnnn nnnnnnnnnn         540
nnnnnnnnnn nnnnnnnnnn nnnnnnnnnn nnnnnnnnnn nnnnnnnnnn nnnnnnnnnn         600
nnnnnagctc tcgagattac cctgttatcc ctaagct                                  637

SEQ ID NO: 101          moltype = DNA   length = 127
FEATURE                 Location/Qualifiers
misc_feature            1..127
                        note = exemplary 3' junction site sequence following GFP
                            knock-in
variation               27..92
                        note = a, c, t, g, unknown or other
source                  1..127
                        mol_type = other DNA
                        organism = synthetic construct
SEQUENCE: 101
caaactcatc aagctgcgag caacttnnnn nnnnnnnnnn nnnnnnnnnn nnnnnnnnnn          60
nnnnnnnnnn nnnnnnnnnn nnnnnnnnnn nncatgaagt tgctcgcagc tggggtgtgg         120
ggccaag                                                                   127

SEQ ID NO: 102          moltype = DNA   length = 114
FEATURE                 Location/Qualifiers
misc_feature            1..114
```

```
                        note = exemplary 3' junction site sequence following GFP
                        knock-in
variation               27..79
                        note = a, c, t, g, unknown or other
source                  1..114
                        mol_type = other DNA
                        organism = synthetic construct
SEQUENCE: 102
gctgtacaag tggctgcgag caacttnnnn nnnnnnnnnn nnnnnnnnnn nnnnnnnnnn    60
nnnnnnnnnn nnnnnnnnnc atgaagttgc tcgcagctgg ggtgtggggc caag         114

SEQ ID NO: 103          moltype = DNA   length = 139
FEATURE                 Location/Qualifiers
misc_feature            1..139
                        note = exemplary 3' junction site sequence following GFP
                        knock-in
variation               27..104
                        note = a, c, t, g, unknown or other
source                  1..139
                        mol_type = other DNA
                        organism = synthetic construct
SEQUENCE: 103
gctgtacaag tggctgcgag caacttnnnn nnnnnnnnnn nnnnnnnnnn nnnnnnnnnn    60
nnnnnnnnnn nnnnnnnnnn nnnnnnnnnn nnnnnnnnnn nnnncatgaa gttgctcgca   120
gctggggtgt ggggccaag                                                139
```

METHODS AND COMPOSITIONS FOR GENOME EDITING IN NON-DIVIDING CELLS

RELATED APPLICATIONS

This application is a divisional claiming priority to co-pending U.S. application Ser. No. 16/318,120, filed Jan. 15, 2019, which is a U.S. National Stage Entry of PCT/US 2017/042151, filed Jul. 14, 2017, which claims the benefit to U.S. Provisional Application No. 62/363,164, filed on Jul. 15, 2016, the contents of all of which are incorporated herein by reference in their entireties.

STATEMENT AS TO FEDERALLY SPONSORED RESEARCH

This invention was made with government support under NIH Grant R01HL123755 awarded by the National Institutes of Health. The government has certain rights in the invention.

INCORPORATION OF SEQUENCE LISTING

The Sequence Listing is submitted as an XML file in the form of the file named "7158-96588-09_ST26.xml" (~143,039 bytes), which was created on Jun. 5, 2023 which is incorporated by reference herein.

BACKGROUND OF THE INVENTION

One of the major therapeutic approaches to combat detrimental cellular phenotypes caused by loss of function mutations relies on intracellular delivery of a wild-type gene copy. In this regard viral-mediated gene-replacement therapy, a rapidly evolving field, has provided some solutions limited by incomplete control over transgene copy numbers and expression levels, as well as the risk of adverse phenotypic effects such as insertional mutagenesis and activation of proto-oncogenes. Site-specific transgene integration exploiting the homology-directed repair (HDR) pathway offers one solution to these problems. However the utility of HDR is limited by its low efficiency in most primary cells. Moreover, HDR occurs only in the S/G2 phases of the cell cycle making it inaccessible to non-dividing cells, which are prevalent in post-natal animal tissues.

SUMMARY OF THE INVENTION

In some aspects, there are provided, methods of integrating an exogenous DNA sequence into a genome of a non-dividing cell. In some embodiments, the method comprises contacting the non-dividing cell with a targeting construct comprising the exogenous DNA sequence and a targeting sequence, a complementary strand oligonucleotide homologous to the targeting sequence, and a nuclease, wherein the exogenous DNA sequence comprises at least one nucleotide difference compared to the genome and the targeting sequence is recognized by the nuclease. In some embodiments, the exogenous DNA sequence comprises a reporter gene. In some embodiments, the reporter gene is selected from at least one of a green fluorescent protein (GFP), a red fluorescent protein (RFP), a luciferase, a β-galactosidase, and a β-glucuronidase. In some embodiments, the exogenous DNA sequence comprises a gene transcription regulatory element. In some embodiments, the gene transcription regulatory element comprises a promoter sequence or an enhancer sequence. In some embodiments, the exogenous DNA sequence corrects a mutation in the genome of the non-dividing cell. In some embodiments, the exogenous DNA sequence causes a mutation in the genome of the non-dividing cell. In some embodiments, the mutation is selected from a missense mutation, a nonsense mutation, a silent mutation, an insertion, and a deletion. In some embodiments, the nuclease is selected from a CRISPR nuclease, a TALEN, a meganuclease, a DNA guided nuclease, and a Zinc Finger Nuclease. In some embodiments, the CRISPR nuclease is selected from Cas9, Cpf1, Cas12b (C2c1), Cas13a (C2c2), Cas13b (C2c6), and C2c3. In some embodiments, the DNA guided nuclease is selected from an argonaute nuclease and a NgAgo nuclease. In some embodiments, the targeting sequence is no longer present once the exogenous DNA has been integrated into the genome in the correct orientation. In some embodiments, the non-dividing cell comprises a terminally differentiated cell. In some embodiments, the targeting construct, the complementary strand oligonucleotide, and a polynucleotide encoding the nuclease are contained in a non-viral or viral vector. In some embodiments, the viral vector is selected from a lentivirus, a retrovirus, an adenovirus, and an adeno-associated virus. In some embodiments, the targeting sequence is sequence specifically cleaved by the nuclease. In some embodiments, the targeting construct comprises two targeting sequences that flank the exogenous DNA sequence. In some embodiments, the targeting construct comprises a minicircle.

In additional aspects, there are provided methods of altering a DNA sequence in a genome of a non-dividing cell. In some embodiments, the method comprises contacting the non-dividing cell with a targeting construct comprising an exogenous DNA sequence and a targeting sequence, a complementary strand oligonucleotide homologous to the targeting sequence, and a nuclease, wherein the exogenous DNA sequence comprises at least one nucleotide difference compared to the genomic DNA sequence and the targeting sequence is recognized by the nuclease. In some embodiments, the exogenous DNA sequence comprises a reporter gene. In some embodiments, the reporter gene is selected from at least one of a green fluorescent protein (GFP), a red fluorescent protein (RFP), a luciferase, a β-galactosidase, and a β-glucuronidase. In some embodiments, the exogenous DNA sequence comprises a gene transcription regulatory element. In some embodiments, the gene transcription regulatory element comprises a promoter sequence or an enhancer sequence. In some embodiments, the exogenous DNA sequence corrects a mutation in the genome of the non-dividing cell. In some embodiments, the exogenous DNA sequence causes a mutation in the genome of the non-dividing cell. In some embodiments, the mutation is selected from a missense mutation, a nonsense mutation, a silent mutation, an insertion, and a deletion. In some embodiments, the nuclease is selected from a CRISPR nuclease, a TALEN, a DNA guided nuclease, a meganuclease, and a Zinc Finger Nuclease. In some embodiments, the CRISPR nuclease is selected from Cas9, Cpf1, Cas12b (C2c1), Cas13a (C2c2), Cas13b (C2c6), and C2c3. In some embodiments, the DNA guided nuclease is selected from an argonaute nuclease and a NgAgo nuclease. In some embodiments, the targeting sequence is no longer present once the genomic DNA sequence has been altered. In some embodiments, the non-dividing cell comprises a terminally differentiated cell. In some embodiments, the targeting construct, the complementary strand oligonucleotide, and a polynucleotide encoding the nuclease are contained in a non-viral or viral vector. In some embodiments, the viral vector is selected from a lentivirus, a retrovirus, an adenovirus, and an adeno-associated virus. In some embodiments, the targeting sequence is specifically cleaved by the nuclease. In some embodiments, the targeting construct comprises two targeting sequences that flank the exogenous DNA sequence. In some embodiments, the targeting construct comprises a minicircle.

In additional aspects, there are provided methods of altering a DNA sequence. In some embodiments, the method comprises contacting the DNA sequence to a targeting construct comprising an exogenous DNA sequence and two copies of a targeting sequence, a complementary strand oligonucleotide homologous to the targeting sequence, and a nuclease, wherein the exogenous DNA sequence comprises at least one nucleotide difference compared to the DNA sequence and the targeting sequence is recognized by the nuclease. In some embodiments, the exogenous DNA sequence comprises a reporter gene. In some embodiments, the reporter gene is selected from at least one of a green fluorescent protein (GFP), a red fluorescent protein (RFP), a luciferase, a β-galactosidase, and a β-glucuronidase. In some embodiments, the exogenous DNA sequence comprises a gene transcription regulatory element. In some embodiments, the gene transcription regulatory element comprises a promoter sequence or an enhancer sequence. In some embodiments, the exogenous DNA sequence corrects a mutation. In some embodiments, the exogenous DNA sequence causes a mutation. In some embodiments, the mutation is selected from a missense mutation, a nonsense mutation, a silent mutation, an insertion, and a deletion. In some embodiments, the nuclease is selected from a CRISPR nuclease, a TALEN, a DNA guided nuclease, a meganuclease, and a Zinc Finger Nuclease. In some embodiments, the CRISPR nuclease is selected from Cas9, Cpf1, Cas12b (C2c1), Cas13a (C2c2), Cas13b (C2c6), and C2c3. In some embodiments, the DNA guided nuclease is selected from an argonaute nuclease and a NgAgo nuclease. In some embodiments, the DNA sequence is at least a portion of a genome of a cell. In some embodiments, the cell is a dividing cell. In some embodiments, the cell is a non-dividing cell. In some embodiments, the non-dividing cell is a terminally differentiated cell. In some embodiments, the targeting sequence is no longer present once the DNA sequence has been altered with the targeting sequence in the correct orientation. In some embodiments, the targeting construct, the complementary strand oligonucleotide, and a polynucleotide encoding the nuclease are contained in a non-viral or viral vector. In some embodiments, the viral vector is selected from a lentivirus, a retrovirus, an adenovirus, and an adeno-associated virus. In some embodiments, the targeting sequence is specifically cleaved by the nuclease.

In further aspects, there are provided methods of treating a genetic disease in a subject in need thereof. In some embodiments, the genetic disease results from a mutated gene having at least one changed nucleotide compared to a wild-type gene. In some embodiments, the method comprises contacting at least one cell of the subject with a composition comprising a targeting construct comprising a DNA sequence homologous to the wild-type gene or fragment thereof and a targeting sequence, a complementary strand oligonucleotide homologous to the targeting sequence, and a nuclease. In some embodiments, the targeting sequence is recognized by the nuclease such that the mutated gene or mutated fragment thereof is replaced with the wild-type gene, or fragment thereof. In some embodiments, the mutated gene comprises a mutation selected from a missense mutation, a nonsense mutation, a silent mutation, an insertion, and a deletion. In some embodiments, the nuclease is selected from a CRISPR nuclease, a TALEN, a DNA guided nuclease, a meganuclease, and a Zinc Finger Nuclease. In some embodiments, the CRISPR nuclease is selected from Cas9, Cpf1, Cas12b (C2c1), Cas13a (C2c2), Cas13b (C2c6), and C2c3. In some embodiments, the DNA guided nuclease is selected from an argonaute nuclease and a NgAgo nuclease. In some embodiments, the targeting construct, the complementary strand oligonucleotide, and a polynucleotide encoding the nuclease are contained in a non-viral or viral vector. In some embodiments, the viral vector is selected from a lentivirus, a retrovirus, an adenovirus, and an adeno-associated virus. In some embodiments, the targeting sequence is specifically cleaved by the nuclease. In some embodiments, the targeting sequence is no longer present once the mutated gene or fragment thereof is replaced with the wildtype gene or fragment thereof in the correct orientation. In some embodiments, the genetic disease is selected from Achondroplasia, Alpha-1 Antitrypsin Deficiency, Alzheimer's disease, Antiphospholipid Syndrome, Autism, Autosomal Dominant Polycystic Kidney Disease, Breast cancer, Cancer, Charcot-Marie-Tooth, Colon cancer, Cri du chat, Crohn's Disease, Cystic fibrosis, Dercum Disease, Down Syndrome, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Leber's congenital amaurosis, Marfan syndrome, Myotonic Dystrophy, Neurofibromatosis, Noonan Syndrome, Osteogenesis Imperfecta, Parkinson's disease, Phenylketonuria, Poland Anomaly, Porphyria, Progeria, Prostate Cancer, Retinitis Pigmentosa, Severe Combined Immunodeficiency (SCID), Sickle cell disease, Skin Cancer, Spinal Muscular Atrophy, Stargardt disease, Tay-Sachs, Thalassemia, Trimethylaminuria, Turner Syndrome, Velocardiofacial Syndrome, WAGR Syndrome, and Wilson Disease.

In additional aspects, there are provided, compositions comprising a targeting construct comprising a DNA sequence homologous to a wild-type gene or fragment thereof and a targeting sequence, a complementary strand oligonucleotide homologous to the targeting sequence, and a nuclease. In some embodiments, the targeting sequence is recognized by the nuclease, for use in treating a genetic disease. In some embodiments, the genetic disease is caused by a mutation selected from a missense mutation, a nonsense mutation, a silent mutation, an insertion, and a deletion. In some embodiments, the nuclease is selected from a CRISPR nuclease, a TALEN, a DNA guided nuclease, a meganuclease, and a Zinc Finger Nuclease. In some embodiments, the CRISPR nuclease is selected from Cas9, Cpf1, Cas12b (C2c1), Cas13a (C2c2), Cas13b (C2c6), and C2c3. In some embodiments, the DNA guided nuclease is selected from an argonaute nuclease and a NgAgo nuclease. In some embodiments, the targeting construct, the complementary strand oligonucleotide, and a polynucleotide encoding the nuclease are contained in a non-viral or viral vector. In some embodiments, the viral vector is selected from a lentivirus, a retrovirus, an adenovirus, and an adeno-associated virus. In some embodiments, the targeting sequence is specifically cleaved by the nuclease. In some embodiments, the targeting sequence is no longer present once the mutated gene or fragment thereof is replaced with the wildtype gene or fragment thereof in the correct orientation. In some embodiments, the genetic disease is selected from Achondroplasia, Alpha-1 Antitrypsin Deficiency, Alzheimer's disease, Antiphospholipid Syndrome, Autism, Autosomal Dominant Polycystic Kidney Disease, Breast cancer, Cancer, Charcot-Marie-Tooth, Colon cancer, Cri du chat, Crohn's Disease, Cystic fibrosis, Dercum Disease, Down Syndrome, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Leber's congenital amaurosis, Marfan syndrome, Myotonic Dystrophy, Neurofibromatosis, Noonan Syndrome, Osteogenesis Imperfecta, Parkinson's disease, Phenylketonuria, Poland Anomaly, *Porphyria*, Progeria, Prostate Cancer, Retinitis Pigmentosa, Severe Combined Immunodeficiency (SCID), Sickle cell disease, Skin Cancer, Spinal Muscular Atrophy, Stargardt disease, Tay-Sachs, Thalassemia, Trimethylaminuria, Turner Syndrome, Velocardiofacial Syndrome, WAGR Syndrome, and Wilson Disease.

In additional aspects, there are provided, compositions comprising a targeting construct comprising an exogenous DNA sequence and at least two targeting sequences, a complementary strand oligonucleotide homologous to the targeting sequence, and a nuclease. In some embodiments, the exogenous DNA sequence comprises a reporter gene. In some embodiments, the reporter gene is selected from at least one of a green fluorescent protein (GFP), a red fluorescent protein (RFP), a luciferase, a β-galactosidase, and a β-glucuronidase. In some embodiments, the exogenous DNA sequence comprises a gene transcription regulatory element. In some embodiments, the gene transcription regulatory element comprises a promoter sequence or an enhancer sequence. In some embodiments, the targeting sequence is recognized by the nuclease. In some embodiments, the composition comprises a non-dividing cell. In some embodiments, the targeting construct, the complementary strand oligonucleotide, and a polynucleotide encoding the nuclease are contained in a non-viral or viral vector. In some embodiments, the viral vector is selected from a lentivirus, a retrovirus, an adenovirus, and an adeno-associated virus. In some embodiments, the composition comprises a pharmaceutically acceptable buffer or excipient.

In additional aspects, there are provided compositions comprising an exogenous DNA sequence and a first half and a second half of a targeting sequence inserted into a genome of a non-dividing cell. In some embodiments, the first half and the second half of the targeting sequence have been cleaved by a nuclease and the first half and second half of the targeting sequence are inserted into the genome upstream and downstream of the exogenous DNA sequence. In some embodiments, the exogenous DNA sequence comprises a reporter gene. In some embodiments, the reporter gene is selected from at least one of a green fluorescent protein (GFP), a red fluorescent protein (RFP), a luciferase, a β-galactosidase, and a β-glucuronidase. In some embodiments, the exogenous DNA sequence comprises a gene transcription regulatory element. In some embodiments, the gene transcription regulatory element comprises a promoter sequence or an enhancer sequence. In some embodiments, the exogenous DNA sequence is integrated into the genome of the non-dividing cell by a virus and a nuclease. In some embodiments, the virus is selected from a lentivirus, a retrovirus, an adenovirus, and an adeno-associated virus. In some embodiments, the nuclease is selected from a CRISPR nuclease, a TALEN, a DNA guided nuclease, a meganuclease, and a Zinc Finger Nuclease. In some embodiments, the CRISPR nuclease is selected from Cas9, Cpf1, Cas12b (C2c1), Cas13a (C2c2), Cas13b (C2c6), and C2c3. In some embodiments, the DNA guided nuclease is selected from an argonaute nuclease and a NgAgo nuclease. In some embodiments, the composition comprises a pharmaceutically acceptable buffer or excipient.

In additional aspects, there are provided, kits comprising a targeting construct comprising an exogenous DNA sequence and at least one targeting sequence, a complementary strand oligonucleotide homologous to the targeting sequence, a nuclease, and instructions for making genetic alterations to non-dividing cells. In some embodiments, the exogenous DNA sequence comprises a reporter gene. In some embodiments, the reporter gene is selected from at least one of a green fluorescent protein (GFP), a red fluorescent protein (RFP), a luciferase, a (3-galactosidase, and a β-glucuronidase. In some embodiments, the exogenous DNA sequence comprises a gene transcription regulatory element. In some embodiments, the gene transcription regulatory element comprises a promoter sequence or an enhancer sequence. In some embodiments, the targeting sequence is recognized by the nuclease. In some embodiments, the targeting construct comprises at least two targeting sequences. In some embodiments, the targeting construct comprises a minicircle. In some embodiments, the targeting construct, the complementary strand oligonucleotide, and a polynucleotide encoding the nuclease are contained in a non-viral or viral vector. In some embodiments, the nuclease is selected from a CRISPR nuclease, a TALEN, a DNA guided nuclease, a meganuclease, and a Zinc Finger Nuclease. In some embodiments, the CRISPR nuclease is selected from Cas9, Cpf1, Cas12b (C2c1), Cas13a (C2c2), Cas13b (C2c6), and C2c3. In some embodiments, the DNA guided nuclease is selected from an argonaute nuclease and a NgAgo nuclease. In some embodiments, the viral vector is selected from a lentivirus, a retrovirus, an adenovirus, and an adeno-associated virus.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows a schematic of targeted gene modification by homology-directed repair (HDR) or HITI in HEK293 GFP-correction line. Pentagon, Cas9/gRNA target sequence. Black line within pentagon, Cas9 cleavage site. Promoterless IRESmCherry plasmids with zero, one, or two CRISPR-Cas9 target sites (IRESmCherry-0c, IRESmCherry-1c and IRESmCherry-2c, respectively) were used to measure HITI efficiency. HDR-donor (tGFP) was used to measure HDR efficiency. FIG. 1B shows representative images of the targeted gene modification in HEK293 cells by HDR and HITI. Scale bar, 100 µm. FIG. 1C shows targeted gene modification efficiency by HDR and HITI. n=3. FIG. 1D shows time course studies for the percentages of mCherry+ cells with different HITI targeting vectors. FIG. 1E shows the CpG methylation status of mCherry gene at early (day 10) and late passages (day 79) with different HITI targeting vectors. Two half-arrows indicate primers for bisulfite sequencing. FIG. 1F shows a schematic of experimental design for in vitro targeted GFP knock-in by HITI in primary neurons. Donor DNA containing GFP, Cas9 expression plasmid and gRNA-mCherry expression plasmid were co-transfected into mouse primary neurons derived from E14.5 embryo. EdU treated from day 3 to day 8 post-transfection. FIG. 1G shows representative images of GFP+ neurons transfected with BPNLS-Cas9, gRNA-mCherry, and Tubb3-MC plasmids. Scale bar, 100 µm. FIG. 1H shows the percentage of knock-in GFP+ cells per transfected mCherry+ cells in either EdU+ or EdU- neurons. n=3. FIG. 1I shows the percentage of knock-in GFP+ cells per transfected mCherry+ cell with HDR donor (Tubb3-HDR), 1 cut donor (Tubb3-1c), 2 cut donor (Tubb3-2c), and minicircle donor (Tubb3-MC). **P<0.01. n=3, Student's t-test. FIG. 1J Left panel shows schematic of different inserted DNA sequences with HITI donors. Pentagon, Cas9-target sequence. Black line within pentagon, Cas9 cleavage site (SEQ ID NO: 1). Underlined sequence, PAM sequence, pA, polyA. Right panel shows intracellular distribution of Tubb3-GFP. FIG. 1K Left panel shows schematic of Tubb3-2c and Tubb3-MC donor integration at the 3'end of Tubb3 coding region. Half-arrows indicate PCR primer pairs for detecting integrated sequences. Right panel shows the PCR result. FIG. 1L shows the percentage of knock-in GFP+ cells per transfected mCherry+ cell with empty vector, Cas9(+NLS), and Cas9(+BPNLS).

FIG. 2A shows a schematic of experimental design for targeted GFP knock-in by HITI in fetal brain via in utero electroporation. BPNLS-Cas9 expression plasmid (CAG-Cas9), gRNA and mCherry expression plasmid (gRNA-mCherry), and minicircle donor (Tubb3-MC) were electroporated into the brain of E15.5 mouse embryos and analyzed at postnatal P21. FIG. 2B shows representative images of GFP knock-in at Tubb3 locus in fetal brain by in utero electroporation. Scale bar, 100 µm. mCherry labels successfully transfected cells. FIG. 2C shows knock-in efficiency measured by the percentage of GFP+ cells among all mCherry+ cells. n=3. FIG. 2D shows schematic of experimental design for in vivo targeted GFP knock-in by HITI in neonatal mouse brain. Inducible BPNLS-Cas9 expression plasmid (CAG-floxSTOP-Cas9), tamoxifen (TAM) inducible CreERT2 expression plasmid (ERT2-CreERT2), gRNA-mCherry, and Tubb3-MC were first electroporated into the brain of E15.5 mouse embryos. To induce Cas9 expression postnatally, tamoxifen was injected at P10 and P11 then analyzed at P21. FIG. 2E shows representative images of GFP knock-in at Tubb3 locus in neonatal brain by inducible Cas9 expression with HDR donor (Tubb3-HDR) or minicircle donor (Tubb3-MC). Scale bar, 100 µm. FIG. 2F shows knock-in efficiencies of HDR and HITI donors with or without tamoxifen treatment as measured by the percentage of GFP+ cells among all mCherry+ cells. n=3. **P<0.01, Student's t-test. FIG. 2G shows a schematic of experimental design for in vivo targeted GFP-NLS or luciferase gene knock-in by HITI. CAG-Cas9, gRNA-mCherry and minicircle donor (Ai14-GFPNLS-MC or Ai14-luc-MC) were locally delivered to mouse kidney or muscle via pressure-mediated transfection and/or electroporation at 8 weeks and analyzed two weeks later. FIG. 2H shows in vivo imaging of luciferase signals at day 2, day 8, and day 14 post-intramuscular injection of luciferase gene knock-in constructs. Right leg (–Cas9) was delivered with empty plasmid, gRNA-mCherry, and Ai14-luc-MC. Left leg (+Cas9) was delivered with CAG-Cas9, gRNA-mCherry, and Ai14-luc-MC. Arrows indicate luciferase signals in the muscle. FIG. 2I shows immunofluorescence analysis of GFP expression after intramuscular electroporation of GFP-NLS knock-in constructs into quadriceps (upper panel) and panniculus carnosus (lower panel). Left panel (–Cas9) was delivered with empty plasmid, gRNA-mCherry, and Ai14-GFPNLS-MC. Right panel (+Cas9) was delivered with CAG-Cas9, gRNA-mCherry, and Ai14-GFPNLS-MC. Scale bar, 100 µm. Arrows indicate GFP signals. FIG. 2J shows in vivo imaging of luciferase signals at day 7 and day 14 after pressure-mediated kidney transfection of luciferase gene knock-in constructs. Left mouse (–Cas9) was delivered with empty plasmid, gRNA-mCherry, and Ai14-luc-MC. Right mouse (+Cas9) was delivered with CAG-Cas9, gRNA-mCherry, and Ai14-luc-MC. Arrows indicate luciferase signals in the right kidney. FIG. 2K shows ex vivo luciferase imaging of stomach and esophagus (St+E), heart (H), liver (Li), spleen (Sp), lungs (Lu), right (R) and left (L) kidney (K), pancreas (Pa), small intestine (SI), cecum (Ce), and colon (Co). Arrow showed luciferase signal in right kidney. FIG. 2L shows immunofluorescence analysis of GFP expression after electroporation of GFP-NLS knock-in constructs into kidney. Upper panel (–Cas9) was delivered with empty plasmid, gRNA-mCherry, and Ai14-GFPNLS-MC. Lower panel (+Cas9) was delivered with CAG-Cas9, gRNA-mCherry, and Ai14-GFPNLS-MC. Scale bar, 100 µm.

FIG. 3A shows a schematic of AAV vectors for knock-in GFP at 3' of Tubb3 gene. Half-arrows indicate PCR primer pairs to validate correct gene knock-in. FIG. 3B shows representative images of GFP knock-in at Tubb3 locus in pan-neurons after AAV infections. Upper panel shows AAV-mTubb3 only. Lower panel, AAV-Cas9 and AAV-mTubb3. Scale bar, 100 µm. FIG. 3C shows intracellular distribution of GFP signal after AAV-Cas9 and AAV-mTubb3 infection. FIG. 3D shows validation of correct gene knock-in by PCR. FIG. 3E shows a schematic of experimental design for in vivo targeted GFP knock-in by HITI via local AAV injections in adult brain. FIG. 3F shows representative immunofluorescence images of GFP+ neuron in the AAV-injected brain sections. Scale bar, 100 µm. FIG. 3G shows a schematic of AAV vectors for knock-in GFP-NLS at downstream of CAG promoter in Rosa26 locus of Ai14 mouse. Arrows indicate PCR primer pairs to validate correct gene knock-in. FIG. 3H shows a schematic of experimental design for in vivo targeted GFP-NLS gene knock-in by HITI via intramuscular (IM) injection. AAV-Cas9 and AAV-Ai14-GFP were locally delivered to quadriceps at 8 weeks and analyzed at 12 weeks. FIG. 3I shows immunofluorescence analysis of GFP expression after IM delivery of AAVs. Upper panel (–Cas9) was delivered with AAV-Ai14-GFP. Lower panel (+Cas9) was delivered with AAV-Cas9 and AAV-Ai14-GFP. Dystrophin was used as a marker for muscle cytoskeletal protein. Scale bar, 100 µm. FIG. 3J shows validation of correct gene knock-in in muscle by PCR. FIG. 3K shows a schematic of experimental design for in vivo targeted GFP-NLS knock-in by HITI via intravenous (IV) AAV injections. AAV-Cas9 and AAV-Ai14-GFP were systemically delivered via intravenously at P1 and analyzed after 2 weeks. FIG. 3L shows immunofluorescence analysis of GFP expression after IV injection of AAVs. Upper panel (–Cas9) was delivered with AAV-Ai14-GFP. Lower panel (+Cas9) was delivered with AAV-Cas9 and AAV-Ai14-GFP. α-smooth muscle actin (αSMA) and albumin were used as markers for heart and liver, respectively. Scale bar, 200 µm. FIG. 3M shows validation of correct gene knock-in in heart and liver by PCR.

FIGS. 4A-4H show targeted in vivo gene correction of rat model of RP via HITI. FIG. 4A shows a schematic representation of the Mertk gene in both wild type and RCS rats.

Pentagon, Cas9/gRNA target sequence. Black line within pentagon, Cas9 cleavage site. FIG. 4B shows a schematic of Mertk gene correction AAV vectors. Exon 2 including surrounding intron is sandwiched by Cas9/gRNA target sequence and integrates within intron 1 of Mertk by HITI. Half-arrows indicate PCR primer pairs to validate correct knock-in. FIG. 4C shows a schematic of experimental design for Mertk gene correction in RCS rats. AAV-Cas9 and AAV-rMertk were locally delivered to RCS rats by subretinal injection at 3 weeks and analyzed at 7-8 weeks. FIG. 4D shows validation of correct gene knock-in in AAV-injected eye by PCR. FIG. 4E shows retinal morphology showing photoreceptor rescue in AAV-injected eyes. Increased preservation of photoreceptor outer nuclear layer (ONL) was observed compared to untreated RCS eyes which had only a very thin ONL (red bracket). Scale bars, 100 μm. FIG. 4F upper panels show a positive GFP signal after AAV injection. Lower panels show increased expression of rhodopsin in photoreceptors demonstrating a positive effect of transgenic rMertk in RPE of treated RCS eyes. Scale bars, 50 μm. Arrows indicate GFP or Rhodopsin signals. FIG. 4G shows improved rod and cone mix response (left, wave forms; right, quantification bars), demonstrating improved b-wave value in AAV-Cas9 and AAV-rMertk injected eyes. FIG. 4H shows improved 10 Hz flicker cone response in AAV-Cas9 and AAV-rMertk injected eyes. Number of animals for all bar graphs: RCS rats n=8, normal rats n=8, and for RCS+AAV group n=3. *P<0.05, Student's t-test.

FIGS. 5A-5F show optimization of donor vectors for HITI. FIG. 5A shows a schematic of HITI with different donor vectors. Cas9/gRNA introduced DNA double strand breaks (DSBs) at 3 bp upstream of PAM sequence and resulted in two blunt ends. The Cas9/gRNA target chromosome sequence is added in reverse direction to different donor plasmids (1cut, 2cut and minicircle donor). Target genomic locus as well as the donor plasmids were cleaved by Cas9/gRNA in cells and the linearized donor DNA were integrated at target sites via classical NHEJ DSB repair pathway. If the donor DNA is integrated in correct orientation, the junction sequence will be protected from further cleavage by Cas9/gRNA. If the donor DNA is integrated in reverse orientation, Cas9/gRNA will keep cutting the integrated donor DNA out from the integration site due to intact Cas9/gRNA target sites. Pentagon, Cas9/gRNA target sequence. Black line within pentagon, Cas9 cleavage site. GOI, gene of interest. FIG. 5B shows the effect of NHEJ inhibitor (NU7026; 30 μM) on targeted gene modification efficiency by HDR and HITI. n=3. N. S., no significance. **P<0.01, Student's t-test. FIG. 5C shows sequences of the 5' and 3' junction sites after IRESmCherry knock-in by HITI in HEK293 GFP-correction line with IRESmCherry-1c donor. At both the 5' and 3' junction sites 'genome' is SEQ ID NO: 2; 'IRESmCherry-1c' is SEQ ID NO: 3. 5' junction site sequences following IRESmCherry knock-in are SEQ ID NO: 4 and SEQ ID NO: 5 in descending order. 3' junction site sequences following IRESmCherry knock-in are SEQ ID NO: 6, SEQ ID NO: 7, SEQ ID NO: 8 and SEQ ID NO: 99 in descending order. Pentagon, Cas9-target sequence. Black line within pentagon, Cas9 cleavage site. Underlined sequence: PAM sequence. FIG. 5D shows sequences of the 5' and 3' junction sites after IRESmCherry knock-in by HITI in HEK293 GFP-correction line with IRESmCherry-2c donor. At the 5' junction site 'genome' is SEQ ID NO: 2 and 'IRESmCherry-2c' is SEQ ID NO: 3. At the 3' junction site 'IRESmCherry-2c' is SEQ ID NO: 11 and 'genome' is SEQ ID NO: 2. 5' junction site sequences following IRESmCherry knock-in are SEQ ID NO: 9 and SEQ ID NO: 10 in descending order. 3' junction site sequences following IRESmCherry knock-in are SEQ ID NO: 12, SEQ ID NO: 13, SEQ ID NO: 14, SEQ ID NO: 15, SEQ ID NO: 16, and SEQ ID NO: 12 in descending order. FIG. 5E shows sequences of the 5' and 3' junction sites after IRESmCherry knock-in by HITI in HEK293 GFP-correction line with IRESmCherry-MC donor. At both the 5' and 3' junction sites 'genome' is SEQ ID NO: 2; 'IRESmCherry-MC' is SEQ ID NO: 3. 5' junction site sequences following IRESmCherry knock-in are SEQ ID NO: 4, SEQ ID NO: 10, and SEQ ID NO: 17 in descending order. 3' junction site sequences following IRESmCherry knock-in are SEQ ID NO: 6 and SEQ ID NO: 100 in descending order. FIG. 5F shows analysis of insertion direction for HITI with IRESmCherry-MC donor. 'Genome' is SEQ ID NO: 18; 'IRESmCherry-MC' is SEQ ID NO: 19. PCR detection of reverse integrated IRESmCherry-MC from single colonies from mCherry- cells. Only one 1 (#30) out of 48 clones was integrated in reverse direction with a 10 bp deletion at junction site revealed by PCR and sequencing analysis. 'Expected connection site' is SEQ ID NO: 20; 'clone #30' is SEQ ID NO: 21.

FIG. 6A shows a schematic representation of a series of dCas9 constructs with different nuclear localization signals. FIG. 6B shows representative immunofluorescence images of the transfected HEK293 cells stained with Flag antibody as an indicator for dCas9 localization. Nuclear showed with DAPI. Scale bar, 50 μm. FIG. 6C shows the nuclear/cytoplasm ratio of dCas9 with different NLS signals. **P<0.01, Student's t-test. FIG. 6D shows an agarose gel image characterization of Cas9 nuclease activity in human ESCs. FIG. 6E shows quantification characterization of Cas9 nuclease activity in human ESCs. Results in FIG. 6D and FIG. 6E are from a surveyor nuclease assay performed with the gRNA targeting KCNQ1 gene and Cas9 with different NLSs, i.e. Cas9 −NLS (Cas9/no NLS), Cas9 +NLS (1NLS-Cas9-1NLS) and Cas9+BPNLS (1BPNLS-Cas9-1BPNLS). The two lower bands are cleaved DNA products by Surveyor nuclease. NHEJ (%) shows the percentage of Cas9/gRNA-mediated gene modification. *P<0.05, Student's t-test.

FIG. 8A At the 5' junction site 'Tubb3 gene locus' is SEQ ID NO: 22 and 'Tubb3-2c' is SEQ ID NO: 23. At the 3' junction site 'Tubb3 gene locus' is SEQ ID NO: 27 and 'Tubb3-2c' is SEQ ID NO: 26. 5' junction site sequences following GFP knock-in are SEQ ID NO: 24 and SEQ ID NO: 25 in descending order. 3' junction site sequences following GFP knock-in are SEQ ID NO: 28 and SEQ ID NO: 101 in descending order. FIG. 8B At both the 5' and 3' junction sites 'Tubb3 gene locus' is SEQ ID NO: 22; 'Tubb3-MC' is SEQ ID NO: 29. 5' junction site sequences following GFP knock-in are SEQ ID NO: 30 and SEQ ID NO: 31 in descending order. 3' junction site sequences following GFP knock-in are SEQ ID NO: 32, SEQ ID NO: 33, and SEQ ID NO: 34 in descending order.

FIG. 9A shows representative immunofluorescence images of hESC-derived human pan neurons transfected with BPNLS-Cas9, gRNA, and different donor DNA (hTUBB3-1c or hTUBB3-2c). Scale bar, 100 μn. FIG. 9B shows PCR analysis of integrated GFP gene at TUBB3 locus in human pan neurons. FIG. 9C and FIG. 9D show sequences of the 5' junction sites after GFP knock-in by HITI in human pan neurons with TUBB3-1c donor (FIG. 9C) and TUBB3-2c donor (FIG. 9D). FIG. 9C the unlabeled sequence is SEQ ID NO: 35; hTUBB3-1c' is SEQ ID NO: 36. 5' junction site sequences following GFP knock-in are SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44 in descending order. FIG. 9D 'Tubb3 gene locus' is SEQ ID NO: 35; hTUBB3-2c' is SEQ ID NO: 36. 5' junction site sequences following GFP knock-in are SEQ ID NO: 37, SEQ ID NO: 45, SEQ ID NO: 46, and SEQ ID NO: 47 in descending order.

FIG. 10A shows representative immunofluorescence images of neurons infected with AAV-Cas9 and AAV-mTubb3. Scale bar, 50 μm. FIG. 10B shows sequences of the 5' and 3' junction sites after GFP knock-in by HITI. At the 5' junction site Tubb3 gene locus' is SEQ ID NO: 22 and 'AAV-mTubb3' is SEQ ID NO: 48. At the 3' junction site 'Tubb3 gene locus' is SEQ ID NO: 27 and 'AAV-mTubb3' is SEQ ID NO: 57. 5' junction site sequences following GFP knock-in are SEQ ID NO: 30, SEQ ID NO: 49, SEQ ID NO: 50, SEQ ID NO: 51, SEQ ID NO: 52, SEQ ID NO: 53, SEQ ID NO: 54, SEQ ID NO: 55, and SEQ ID NO: 56 in descending order. 3' junction site sequences following GFP knock-in are SEQ ID NO: 58, SEQ ID NO: 59, SEQ ID NO: 60, SEQ ID NO: 102, SEQ ID NO: 61, and SEQ ID NO: 103 in descending order.

FIG. 11A shows a schematic of AAVs for knock-in luciferase at downstream of CAG promoter in Rosa26 locus of Ai14 mouse. AAV-Cas9 and AAV-Ai14-luc were systemically delivered via tail vein injection in 8 week old Ai14 mice and analyzed at 12 weeks. FIG. 11B shows in vivo imaging of luciferase signals at day 14 and day 28 post-tail vein injection of luciferase gene knock-in constructs. Arrows indicate luciferase signals. FIG. 11C shows ex vivo luciferase imaging analysis of testis (Te), stomach and esophagus (St+E), heart (H), liver (Li), spleen (Sp), lungs (Lu), right (R) and left (L) kidney (K), pancreas (Pa), Brain (Br), pituitary (Pi), right (R) and left (L) eye, (Ey), Tongue (To), small intestine (SI), cecum (Ce) and colon (Co). The arrow indicates luciferase signal in the liver of AAV-Cas9 and AAV-Ai14-luc injected mouse. FIG. 11D shows representative immunofluorescence image of GFP expression in liver after tail vein injection of HITI GFP-NLS gene knock-in AAVs. Scale bar, 200 μm.

FIG. 12A shows representative immunofluorescence images of GFP expression in brain, muscle, kidney, adrenal gland, spleen, lung, and choroid plexus of eye after IV injection of GFP-NLS knock-in AAVs. Upper panel (-Cas9) was delivered with only AAV-Ai14-GFP. Lower panel (+Cas9) was delivered with AAV-Cas9 and AAV-Ai14-GFP. Scale bar, 100 μm. FIG. 12B shows sequences of the 5' and 3' junction sites of heart and liver cells after GFP-NLS knock-in by HITI via IV AAV injections. At the 5' junction site 'CAG promoter locus' is SEQ ID NO: 62; 'AAV-Ai14-GFP' is SEQ ID NO: 63. At the 3' junction site 'CAG promoter locus' is SEQ ID NO: 62; 'AAV-Ai14-GFP' is SEQ ID NO: 73. 5' junction site sequences following GFP-NLS knock-in in the liver are SEQ ID NO: 64, SEQ ID NO: 65, SEQ ID NO: 66, SEQ ID NO: 67, SEQ ID NO: 68, SEQ ID NO: 69, SEQ ID NO: 70, and SEQ ID NO: 71 in descending order. 5' junction site sequences following GFP-NLS knock-in in the heart are SEQ ID NO: 64, SEQ ID NO: 72, and SEQ ID NO: 65 in descending order. 3' junction site sequences following GFP-NLS knock-in in the liver are SEQ ID NO: 74, SEQ ID NO: 75, SEQ ID NO: 76, SEQ ID NO: 77, SEQ ID NO: 78, and SEQ ID NO: 79 in descending order. 3' junction site sequences following GFP-NLS knock-in in the heart are SEQ ID NO: 74, SEQ ID NO: 75, SEQ ID NO: 80, and SEQ ID NO: 81 in descending order.

FIG. 13 shows next generation sequencing analysis of CRISPR-Cas9 mediated indel frequency at On- and Off-target sites in AAV-injected liver tissue. List of On- and Off-target sites that were used to determine the indel frequency of HITI mediated genome modifications. The nucleotides grey color in the "sequence" column are the individual mismatches within predicted Off-target sites. 'On' is SEQ ID NO: 82; 'OTS1' is SEQ ID NO: 83; 'OTS2' is SEQ ID NO: 84; 'OTS3' is SEQ ID NO: 85; 'OTS4' is SEQ ID NO: 86; 'OTS5' is SEQ ID NO: 87; 'OTS6' is SEQ ID NO: 88; 'OTS7' is SEQ ID NO: 88; 'OTS8' is SEQ ID NO: 89; 'OTS9' is SEQ ID NO: 90; 'OTS10' is SEQ ID NO: 91; 'OTS11' is SEQ ID NO: 92; 'OTS12' is SEQ ID NO: 93.

FIG. 14A shows sequence of 3' connection sites between AAV-rMertk derived exon 2 and integrations site in the eye of the AAV-Cas9 and AAV-rMertk injected RCS rats. 'Mertk locus' is SEQ ID NO: 94; 'AAV-rMertk' is SEQ ID NO: 95. Resulting 3' connection site sequences from the AAV-Cas9 and AAV-rMertk injected rats are SEQ ID NO: 96, SEQ ID NO: 97, SEQ ID NO: 96, and SEQ ID NO: 98 in descending order. FIG. 14B shows fundus photographs showed extensive RPE atrophy in an untreated RCS eye (left); reduced RPE atrophy after AAV-Cas9 and AAV-rMertk injection (middle), and a wild type control (right). Arrows demonstrated visible large choroidal vessels due to RPE atrophy.

FIG. 15A shows a schematic of in vivo targeted GFP-NLS knock-in by HITI via intravenous (IV) AAV injections to Ai14 mice. FIG. 15B shows quantitative GFP knock-in efficiency per cell in the liver, heart, and quadriceps muscle after IV injection of HITI-AAVs serotyped with 9. ** $P<0.01$. FIG. 15C shows representative immunofluorescence images of GFP expression in the liver, heart, and quadriceps muscle after IV injection of HITI-AAVs serotyped with 9.

FIGS. 16A-16K show the results of treatment of Lmna$^{G609G/G609G}$ (LIKI) mice using HITI. FIG. 16A shows a schematic for treatment of Hutchinson-Gilford progeria syndrome (HGPS). FIG. 16B shows a scheme of LMNA gene correction AAV vectors with serotype 9. FIG. 16C shows validation of correct gene knock-in by PCR at day 118. FIG. 16D shows gene knock-in efficiency by qPCR at day 35 and 118. FIG. 16E shows cumulative plot of body weight against age for treated and untreated mice. FIG. 16F shows a survival plot for treated versus untreated mice. FIG. 16G shows representative photographs of 4-month-old Lmna+/+(WT), Lmna$_{G609G/G609G}$ (−HITI), and HITI treated Lmna$^{G609G/G609G}$ mice (+HITI). FIG. 16H shows a photograph of spleens from Lmna$^{G609G/G609G}$ mice upon HITI treatment and untreated mice versus wild type mice. FIG. 16I shows histology (H&E) of aortic arch of LAKI HITI-treated mice and nuclear density quantification. Scale bar, 500 um. *p<0.05, *p<0.001, p<0.0001 according to Post Hoc one-way ANOVA with Ryan's method. FIG. 16J shows histology (PAS) of kidney of LAKI HITI-treated mice and quantification of area of glomerulus and diameter of retinal tubules in kidney. Scale bar, 200 um. p<0.01, **p<0.0001 according to Post Hoc one-way ANOVA with Ryan's method. FIG. 16K shows histology (H&E) of spleen of LAKI HITI-treated mice and quantification of the area of white pulps in the spleen. Scale bar, 5 mm p<0.01, ****p<0.0001 according to Post Hoc one-way ANOVA with Ryan's method.

SEQUENCE LISTING

Figure 1A:
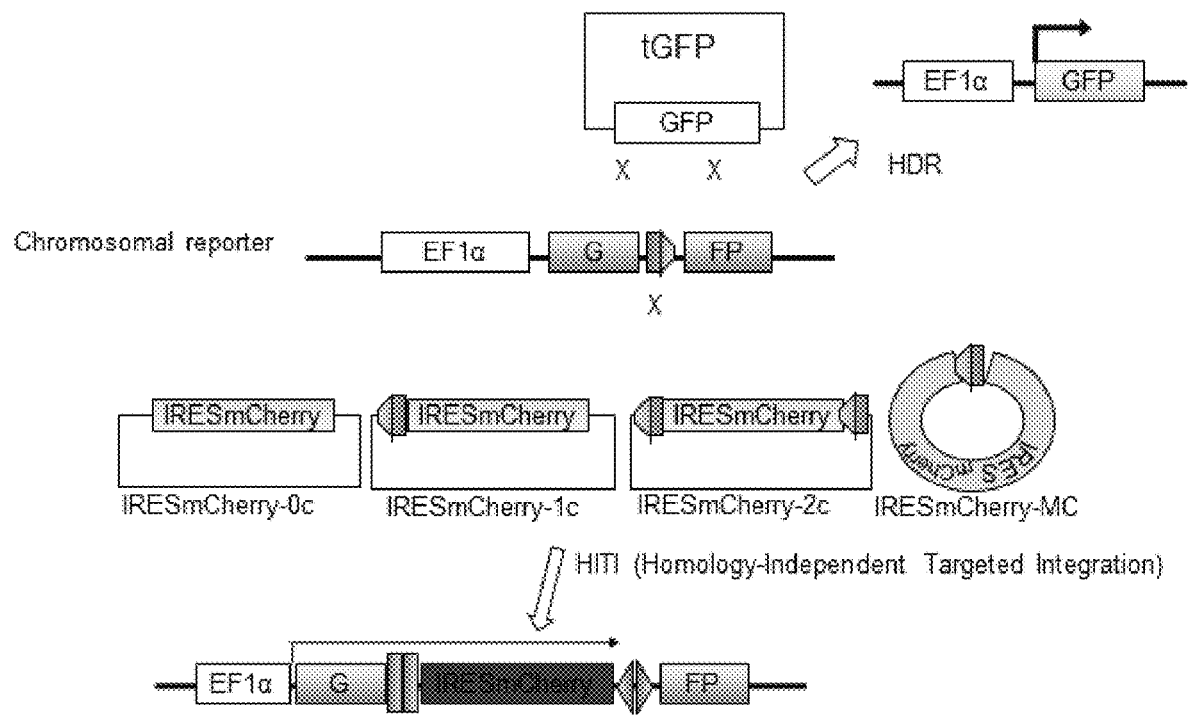
FIGS. 1A-1L show development of homology-independent targeted integration (HITI) method for dividing and non-dividing cells in vitro.

The nucleic and amino acid sequences listed in the accompanying sequence listing are shown using standard letter abbreviations for nucleotide bases, and single letter code for amino acids, as defined in 37 C.F.R. 1.822. Only one strand of each nucleic acid sequence is shown, but the complementary strand is understood as included by any reference to the displayed strand.

SEQ ID NO: 1 is an illustrative sequence containing an exemplary Cas9 cutting site.
SEQ ID NO: 2 is an aspect of an exemplary genome sequence.
SEQ ID NO: 3 is an illustrative aspect of the IRESmCherry-1c plasmid, the IRESmCherry-2c plasmid, and the IRESmCherry-MC plasmid.
SEQ ID NO: 4 is an exemplary 5' junction site sequence following IRESmCherry knock-in.
SEQ ID NO: 5 is an exemplary 5' junction site sequence following IRESmCherry knock-in.
SEQ ID NO: 6 is an exemplary 3' junction site sequence following IRESmCherry knock-in.
SEQ ID NO: 7 is an exemplary 3' junction site sequence following IRESmCherry knock-in.
SEQ ID NO: 8 is an exemplary 3' junction site sequence following IRESmCherry knock-in.
SEQ ID NO: 9 is an exemplary 5' junction site sequence following IRESmCherry knock-in.
SEQ ID NO: 10 is an exemplary 5' junction site sequence following IRESmCherry knock-in.
SEQ ID NO: 11 is an illustrative aspect of the IRESmCherry-2c plasmid.
SEQ ID NO: 12 is an exemplary 3' junction site sequence following IRESmCherry knock-in.
SEQ ID NO: 13 is an exemplary 3' junction site sequence following IRESmCherry knock-in.
SEQ ID NO: 14 is an exemplary 3' junction site sequence following IRESmCherry knock-in.
SEQ ID NO: 15 is an exemplary 3' junction site sequence following IRESmCherry knock-in.
SEQ ID NO: 16 is an exemplary 3' junction site sequence following IRESmCherry knock-in.
SEQ ID NO: 17 is an exemplary 5' junction site sequence following IRESmCherry knock-in.
SEQ ID NO: 18 is an aspect of an exemplary genome sequence.
SEQ ID NO: 19 is an illustrative aspect of the IRESmCherry-MC plasmid.
SEQ ID NO: 20 is an example showing an expected directional sequence following HITI.
SEQ ID NO: 21 is an exemplary sequence showing insertion in the reverse direction.
SEQ ID NO: 22 is an aspect of the Tubb3 gene locus.
SEQ ID NO: 23 is an illustrative aspect of the Tubb3-2c plasmid.
SEQ ID NO: 24 is an exemplary 5' junction site sequence following GFP knock-in.
SEQ ID NO: 25 is an exemplary 5' junction site sequence following GFP knock-in.
SEQ ID NO: 26 is an illustrative aspect of the Tubb3-2c plasmid.
SEQ ID NO: 27 is an aspect of the Tubb3 gene locus.
SEQ ID NO: 28 is an exemplary 3' junction site sequence following GFP knock-in.
SEQ ID NO: 29 is an illustrative aspect of the Tubb3-MC plasmid.
SEQ ID NO: 30 is an exemplary 5' junction site sequence following GFP knock-in.
SEQ ID NO: 31 is an exemplary 5' junction site sequence following GFP knock-in.
SEQ ID NO: 32 is an exemplary 3' junction site sequence following GFP knock-in.
SEQ ID NO: 33 is an exemplary 3' junction site sequence following GFP knock-in.
SEQ ID NO: 34 is an exemplary 3' junction site sequence following GFP knock-in.
SEQ ID NO: 35 is an aspect of the Tubb3 gene locus.
SEQ ID NO: 36 is an illustrative aspect of the hTUBB3-1c plasmid and the hTUBB3-2c plasmid.
SEQ ID NO: 37 is an exemplary 5' junction site sequence following GFP knock-in.
SEQ ID NO: 38 is an exemplary 5' junction site sequence following GFP knock-in.
SEQ ID NO: 39 is an exemplary 5' junction site sequence following GFP knock-in.
SEQ ID NO: 40 is an exemplary 5' junction site sequence following GFP knock-in.
SEQ ID NO: 41 is an exemplary 5' junction site sequence following GFP knock-in.
SEQ ID NO: 42 is an exemplary 5' junction site sequence following GFP knock-in.
SEQ ID NO: 43 is an exemplary 5' junction site sequence following GFP knock-in.
SEQ ID NO: 44 is an exemplary 5' junction site sequence following GFP knock-in.
SEQ ID NO: 45 is an exemplary 5' junction site sequence following GFP knock-in.
SEQ ID NO: 46 is an exemplary 5' junction site sequence following GFP knock-in.
SEQ ID NO: 47 is an exemplary 5' junction site sequence following GFP knock-in.
SEQ ID NO: 48 is an illustrative aspect of the AAV-mTubb3 vector.
SEQ ID NO: 49 is an exemplary 5' junction site sequence following GFP knock-in.
SEQ ID NO: 50 is an exemplary 5' junction site sequence following GFP knock-in.
SEQ ID NO: 51 is an exemplary 5' junction site sequence following GFP knock-in.
SEQ ID NO: 52 is an exemplary 5' junction site sequence following GFP knock-in.
SEQ ID NO: 53 is an exemplary 5' junction site sequence following GFP knock-in.
SEQ ID NO: 54 is an exemplary 5' junction site sequence following GFP knock-in.
SEQ ID NO: 55 is an exemplary 5' junction site sequence following GFP knock-in.
SEQ ID NO: 56 is an exemplary 5' junction site sequence following GFP knock-in.

SEQ ID NO: 57 is an illustrative aspect of the AAV-mTubb3 vector.
SEQ ID NO: 58 is an exemplary 3' junction site sequence following GFP knock-in.
SEQ ID NO: 59 is an exemplary 3' junction site sequence following GFP knock-in.
SEQ ID NO: 60 is an exemplary 3' junction site sequence following GFP knock-in.
SEQ ID NO: 61 is an exemplary 3' junction site sequence following GFP knock-in.
SEQ ID NO: 62 is an aspect of the CAG promoter locus.
SEQ ID NO: 63 is an illustrative aspect of the AAV-Ai14-GFP vector.
SEQ ID NO: 64 is an exemplary 5' junction site sequence following GFP-NLS knock-in.
SEQ ID NO: 65 is an exemplary 5' junction site sequence following GFP-NLS knock-in.
SEQ ID NO: 66 is an exemplary 5' junction site sequence following GFP-NLS knock-in.
SEQ ID NO: 67 is an exemplary 5' junction site sequence following GFP-NLS knock-in.
SEQ ID NO: 68 is an exemplary 5' junction site sequence following GFP-NLS knock-in.
SEQ ID NO: 69 is an exemplary 5' junction site sequence following GFP-NLS knock-in.
SEQ ID NO: 70 is an exemplary 5' junction site sequence following GFP-NLS knock-in.
SEQ ID NO: 71 is an exemplary 5' junction site sequence following GFP-NLS knock-in.
SEQ ID NO: 72 is an exemplary 5' junction site sequence following GFP-NLS knock-in.
SEQ ID NO: 73 is an illustrative aspect of the AAV-Ai14-GFP vector.
SEQ ID NO: 74 is an exemplary 3' junction site sequence following GFP-NLS knock-in.
SEQ ID NO: 75 is an exemplary 3' junction site sequence following GFP-NLS knock-in.
SEQ ID NO: 76 is an exemplary 3' junction site sequence following GFP-NLS knock-in.
SEQ ID NO: 77 is an exemplary 3' junction site sequence following GFP-NLS knock-in.
SEQ ID NO: 78 is an exemplary 3' junction site sequence following GFP-NLS knock-in.
SEQ ID NO: 79 is an exemplary 3' junction site sequence following GFP-NLS knock-in.
SEQ ID NO: 80 is an exemplary 3' junction site sequence following GFP-NLS knock-in.
SEQ ID NO: 81 is an exemplary 3' junction site sequence following GFP-NLS knock-in.
SEQ ID NO: 82 is an exemplary on-target sequence.
SEQ ID NO: 83 is exemplary off-target sequence OTS1.
SEQ ID NO: 84 is an exemplary off-target sequence OTS2.
SEQ ID NO: 85 is an exemplary off-target sequence OTS3.
SEQ ID NO: 86 is an exemplary off-target sequence OTS4.
SEQ ID NO: 87 is an exemplary off-target sequence OTS5.
SEQ ID NO: 88 is an exemplary off-target sequences OTS6 and OTS7.
SEQ ID NO: 89 is an exemplary off-target sequence OTS8.
SEQ ID NO: 90 is an exemplary off-target sequence OTS9.
SEQ ID NO: 91 is exemplary off-target sequence OTS10.
SEQ ID NO: 92 is an exemplary off-target sequence OTS11.
SEQ ID NO: 93 is an exemplary off-target sequence OTS12.
SEQ ID NO: 94 is an aspect of the Mertk locus.
SEQ ID NO: 95 is an illustrative aspect of the AAV-rMertk vector.
SEQ ID NO: 96 is an exemplary 3' connection site sequence following AAV-rMertk treatment.
SEQ ID NO: 97 is an exemplary 3' connection site sequence following AAV-rMertk treatment.
SEQ ID NO: 98 is an exemplary 3' connection site sequence following AAV-rMertk treatment.
SEQ ID NO: 99 is an exemplary 3' junction site sequence following IRESmCherry knock-in.
SEQ ID NO: 100 is an exemplary 3' junction site sequence following IRESmCherry knock-in.
SEQ ID NO: 101 is an exemplary 3' junction site sequence following GFP knock-in.
SEQ ID NO: 102 is an exemplary 3' junction site sequence following GFP knock-in.
SEQ ID NO: 103 is an exemplary 3' junction site sequence following GFP knock-in.

DETAILED DESCRIPTION OF THE INVENTION

Targeted genome editing with engineered nucleases is revolutionizing basic biomedical research and holds tremendous potential for gene therapy. However, and despite rapid advances, the sought after goal of in vivo targeted transgene integration is still unsettled due to a lack of efficient tools. While genome editing in dividing cells has been described previously (see for example, He et al., Nucleic Acids Research, 44(9), 2016, Maresca et al., Genome Research 23:539-546, 2013, Auer et al., Genome Research 24: 142-153, 2014, Bachu et al. Biotechnology and Bioengineering 112(10) 2154-2162, 2015), these techniques have not been useful in genome editing methods in adult cells and tissues. In the case of non-dividing cells, the major constituents of adult tissues, transgene integration is presently inaccessible for targeted knock-in with current technologies. This poses a barrier for uncovering fundamental biological principles and developing therapeutic strategies for a broader range of devastating genetic disorders. Disclosed herein are robust homology-independent targeted integration (HITI) methods and compositions that allow for efficient targeted knock-in in both dividing and non-dividing cells in vitro, and more importantly, for in vivo on-target transgene insertion in post-mitotic cells of neonatal and adult mice. Moreover, preclinical data is provided herein, using a rat model of blindness retinitis pigmentosa and a mouse model of premature aging disease Hutchinson-Gilford progeria syndrome, demonstrating the therapeutic efficacy and functional rescue of HITI in vivo. The HITI methods presented herein open new avenues for both basic research studies as well as for targeted gene therapies.

In summary, demonstrated herein is a robust and efficient Homology-Independent Targeted Integration method (HITI). HITI not only facilitates targeted knock-in in cultured cells but also allows for efficient targeted integration of a reporter gene in vivo in non-dividing cells. More importantly, HITI has been successfully applied to rescue a loss-of-function mutation in a rat model of a common cause of blindness, retinitis pigmentosa, by targeted insertion of a functional exon of the Mertk gene. Furthermore, HITI has been successfully applied to rescue a gain-of-function mutation in a mouse model of a premature aging, Hutchinson-Gilford progeria syndrome, by targeted insertion of a partial gene containing a functional copy of the downstream exons and 3'UTR sequence into the intron of LMNA to replace the defective copy harboring the casual point mutation. The observation that HITI allows for in vivo targeted transgene knock-in of the adult central nervous system has not been previously demonstrated and may help to advance basic as well as translational neuroscience research. In some embodiments, research tools comprise targeted insertion of optogenetic activators, such as channel rhodopsin, to the downstream of any predetermined gene locus to allow for precise cell-type specific control over neuronal activities. In some embodiments, HITI will also allow for generation of knock-in reporters for cell tracing in live animals. In some embodiments, this will allow for creation of animal models where transgenic tools are limited, for example animal models in non-human primates. In addition, HITI, in some embodiments, will allow for genetic enhancement through targeted knocking-in synthetic DNA sequences that confer target cells with novel functions for disease treatment or prevention, for example in chimeric antigen receptor (CAR) T-cell therapy for leukemia. In some embodiments, HITI methods are used in conjunction with efficient and optimized tissue specific in vivo delivery strategies (either viral or non-viral), for in vivo targeted gene-replacement therapy.

Compositions

Provided herein are compositions for making changes to genomic DNA in a target cell or host cell. In some embodiments, such compositions are useful in treating a disease, such as a genetic disease. In some embodiments, provided herein are compositions comprising a targeting construct comprising an exogenous DNA sequence and at least two targeting sequences, a complementary strand oligonucleotide homologous to the targeting sequence, and a nuclease, wherein the targeting sequence is recognized by the nuclease. In some embodiments, there is also provided a composition comprising an exogenous DNA sequence and a first half and a second half of a targeting sequence inserted into a genome of a non-dividing cell, wherein the first half and the second half of the targeting sequence have been cleaved by a nuclease and the first half and second half of the targeting sequence are inserted into the genome upstream and downstream of the exogenous DNA sequence.

Exogenous DNA Sequences

Compositions provided herein comprise targeting constructs comprising exogenous DNA sequences. Exogenous DNA sequences comprise a fragment of DNA to be incorporated into genomic DNA of a target genome. In some embodiments, the exogenous DNA comprises at least a portion of a gene. In some embodiments, the exogenous DNA comprises an exon of a gene. In some embodiments, the exogenous DNA comprises an intron of a gene. In some embodiments, the exogenous DNA comprises an enhancer element or a promoter element of a gene. In some embodiments, the exogenous DNA comprises a discontinuous sequence of a gene comprising a 5' portion of the gene fused to the 3' portion of the gene. In some embodiments, the exogenous DNA comprises a wild type gene sequence. In some embodiments, the exogenous DNA comprises a mutated gene sequence. In some embodiments, the exogenous DNA comprises a wild type gene sequence. In some embodiments, the exogenous DNA sequence comprises a reporter gene. In some embodiments, the reporter gene is selected from at least one of a green fluorescent protein (GFP), a red fluorescent protein (RFP), a luciferase, a β-galactosidase, and a β-glucuronidase. In some embodiments, the exogenous DNA sequence comprises a gene transcription regulatory element. In some embodiments, the gene transcription regulatory element comprises a promoter sequence or an enhancer sequence. In some embodiments, the exogenous DNA sequence comprises one or more exons or fragments thereof. In some embodiments, the exogenous DNA sequence comprises one or more introns or fragments thereof. In some embodiments, the exogenous DNA sequence comprises at least a portion of a 3' untranslated region or a 5' untranslated region. In some embodiments, the exogenous DNA sequence comprises an artificial DNA sequence. In some embodiments, the exogenous DNA sequence comprises a nuclear localization sequence. In some embodiments, the exogenous DNA sequence comprises a nuclear export sequence.

Cleaved ends produced by nuclease cleavage are mainly repaired by non-homologous end joining (NHEJ) or homology-directed repair (HDR). In non-dividing cells, cleaved ends produced by nuclease cleavage are repaired by NHEJ. NHEJ is performed on the two cleaved ends, which in some embodiments results in a non-perfect repair, such as base pairs being deleted or inserted. NHEJ, in some embodiments, is performed to incorporate a homologous or non-homologous exogenous DNA sequence within the cleavage site. NHEJ with a non-homologous exogenous DNA sequence, in some embodiments, results in deletion or insertion of base pairs on one or both ends of the insertion site. HDR is used to seamlessly insert an exogenous DNA sequence into the cleavage site when the exogenous DNA sequence comprises regions of homology on both the 5' and 3' ends, corresponding to each side of the insertion site.

An exogenous DNA sequence, in some embodiments, comprises a segment of nucleic acid to be integrated at a target genomic locus. The exogenous DNA sequence, in some embodiments, comprises one or more polynucleotides of interest. The exogenous DNA sequence in some embodiments comprises one or more expression cassettes. Such an expression cassette, in some embodiments, comprises an exogenous DNA sequence of interest, a polynucleotide encoding a selection marker and/or a reporter gene, and regulatory components that influence expression.

The exogenous DNA sequence, in some embodiments, comprises a genomic nucleic acid. The genomic nucleic acid is derived from an animal, a mouse, a human, a non-human, a rodent, a non-human, a rat, a hamster, a rabbit, a pig, a bovine, a deer, a sheep, a goat, a chicken, a cat, a dog, a ferret, a primate (e.g., marmoset, rhesus monkey), domesticated mammal or an agricultural mammal, an avian, a bacterium, an archaean, a virus, or any other organism of interest or a combination thereof.

Exogenous DNA sequences of any suitable size are integrated into a target genome. In some embodiments, the exogenous DNA sequence integrated into a genome is less than 3, about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 16, 17, 18, 19, 20, 25, 30, 35, 40, 45, 50, 100, 150, 200, 250, 300, 350, 400, 450, 500 or more than 500 kilobases (kb) in length. In some embodiments, the exogenous DNA sequence integrated into a genome is at least about 2, 2.5, 3, 3.5, 4, 4.5, 5, 5.5, 6, 6.5, 7, 7.5, 8, 8.5, 9, 9.5, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length. In some embodiments, the exogenous DNA sequence integrated into a genome is up to about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 30, 35, 40, 45, 50, 100, 150, 200, 250, 300, 350, 400, 450, 500 or more than 500 (kb) in length.

Targeting Sequences

Compositions provided herein comprise targeting constructs comprising at least one targeting sequence. In some embodiments, the targeting construct comprises at least two targeting sequences. Targeting sequences herein are nucleic acid sequences recognized and cleaved by a nuclease disclosed herein in a sequence specific manner. In some embodiments, the targeting sequence is about 9 to about 12 nucleotides in length, from about 12 to about 18 nucleotides in length, from about 18 to about 21 nucleotides in length, from about 21 to about 40 nucleotides in length, from about 40 to about 80 nucleotides in length, or any combination of subranges (e.g., 9-18, 9-21, 9-40, and 9-80 nucleotides). In some embodiments, the targeting sequence comprises a nuclease binding site. In some embodiments the targeting sequence comprises a nick/cleavage site. In some embodiments, the targeting sequence comprises a protospacer adjacent motif (PAM) sequence.

In some embodiments, the target nucleic acid sequence (e.g., protospacer) is 20 nucleotides. In some embodiments, the target nucleic acid is less than 20 nucleotides. In some embodiments, the target nucleic acid is at least 5, 10, 15, 16, 17, 18, 19, 20, 21, 22, 23, 24, 25, or more nucleotides. The target nucleic acid, in some embodiments, is at most 5, 10, 15, 16, 17, 18, 19, 20, 21, 22, 23, 24, 25, 30 or more nucleotides. In some embodiments, the target nucleic acid sequence is 16, 17, 18, 19, 20, 21, 22, or 23 bases immediately 5' of the first nucleotide of the PAM. In some embodiments, the target nucleic acid sequence is 16, 17, 18, 19, 20, 21, 22, or 23 bases immediately 3' of the last nucleotide of the PAM. In some embodiments, the target nucleic acid sequence is 20 bases immediately 5' of the first nucleotide of the PAM. In some embodiments, the target nucleic acid sequence is 20 bases immediately 3' of the last nucleotide of the PAM. In some embodiments, the target nucleic acid sequence is 5' or 3' of the PAM.

A targeting sequence, in some embodiments includes nucleic acid sequences present in a target nucleic acid to which a nucleic acid-targeting segment of a complementary strand nucleic acid binds. For example, targeting sequences, in some embodiments, include sequences to which a complementary strand nucleic acid is designed to have base pairing. A targeting sequence in some embodiments comprises any polynucleotide, which is located, for example, in the nucleus or cytoplasm of a cell or within an organelle of a cell, such as a mitochondrion or chloroplast. Targeting sequences include cleavage sites for nucleases. A targeting sequence, in some embodiments, is adjacent to cleavage sites for nucleases.

The nuclease cleaves the nucleic acid, in some embodiments, at a site within or outside of the nucleic acid sequence present in the target nucleic acid to which the nucleic acid-targeting sequence of the complementary strand binds. The cleavage site, in some embodiments, includes the position of a nucleic acid at which a nuclease produces a single-strand break or a double-strand break. For example, formation of a nuclease complex comprising a complementary strand nucleic acid hybridized to a protease recognition sequence and complexed with a protease results in cleavage of one or both strands in or near (e.g., within 1, 2, 3, 4, 5, 6, 7, 8, 9, 10, 19, 23, 50, or more base pairs from) the nucleic acid sequence present in a target nucleic acid to which a spacer region of a complementary strand nucleic acid binds. The cleavage site, in some embodiments, is on only one strand or on both strands of a nucleic acid. In some embodiments, cleavage sites are at the same position on both strands of the nucleic acid (producing blunt ends) or are at different sites on each strand (producing staggered ends). Staggered ends, in some embodiments, are 5' or 3' overhang sticky-ends. Staggered ends, in some embodiments, are produced by sticky-end producing nucleases (e.g., Cpf1). In some embodiments, staggered ends are produced, for example, by using two nucleases, each of which produces a single-strand break at a different cleavage site on each strand, thereby producing a double-strand break. For example, a first nickase creates a single-strand break on the first strand of double-stranded DNA (dsDNA), and a second nickase creates a single-strand break on the second strand of dsDNA such that overhanging sequences are created. In some cases, the nuclease recognition sequence of the nickase on the first strand is separated from the nuclease recognition sequence of the nickase on the second strand by at least 2, 3, 4, 5, 6, 7, 8, 9, 10, 15, 20, 25, 30, 40, 50, 75, 100, 250, 500, or 1000 base pairs.

Site-specific cleavage of a target nucleic acid by a nuclease, in some embodiments, occurs at locations determined by base-pairing complementarity between the complementary strand nucleic acid and the target nucleic acid. Site-specific cleavage of a target nucleic acid by a nuclease protein, in some embodiments, occurs at locations determined by a short motif, called the protospacer adjacent motif (PAM), in the target nucleic acid. For example, the PAM flanks the nuclease recognition sequence at the 3' end of the recognition sequence. For example, the cleavage site of the nuclease, in some embodiments, is about 1 to about 25, or about 2 to about or about 19 to about 23 base pairs (e.g., 3 base pairs) upstream or downstream of the PAM sequence. In some embodiments, the cleavage site of the nuclease is 3 base pairs upstream of the PAM sequence. In some embodiments, the cleavage site of the nuclease is 19 bases on the (+) strand and 23 base on the (−) strand, producing a 5' overhang 5 nucleotides (nt) in length. In some cases, the cleavage produces blunt ends. In some cases, the cleavage produces staggered or sticky ends with 5' overhangs. In some cases, the cleavage produces staggered or sticky ends with 3' overhangs.

Orthologs of various nuclease proteins utilize different PAM sequences. For example different Cas proteins, in some embodiments, recognize different PAM sequences. For example, in *S. pyogenes*, the PAM is a sequence in the target nucleic acid that comprises the sequence 5'-XRR-3', where R is either A or G, where X is any nucleotide and X is immediately 3' of the target nucleic acid sequence targeted by the spacer sequence. The PAM sequence of *S. pyogenes* Cas9 (SpyCas9) is 5'-XGG-3', where X is any DNA nucleotide and is immediately 3' of the nuclease recognition sequence of the non-complementary strand of the target DNA. The PAM of Cpf1 is 5'-TTX-3', where X is any DNA nucleotide and is immediately 5' of the nuclease recognition sequence.

Complementary Strand Nucleic Acids

A complementary strand nucleic acid, for example, a complementary strand oligonucleotide or a complementary strand RNA, refers to a nucleic acid that hybridizes to another nucleic acid, for example, the target nucleic acid in genome of a cell. A complementary strand nucleic acid is RNA, in some embodiments. In some embodiments, a complementary strand nucleic acid is DNA. A complementary strand nucleic acid, in some embodiments, comprises a nucleotide analog. A complementary strand nucleic acid, in some embodiments, comprises a modified nucleotide. The complementary strand nucleic acid, in some embodiments, is programmed or designed to bind to a sequence of nucleic acid site-specifically.

A complementary strand nucleic acid, in some embodiments, comprises one or more modifications to provide the nucleic acid with a new or enhanced feature. In some embodiments, a complementary strand nucleic acid comprises a nucleic acid affinity tag. In some embodiments, a complementary strand nucleic acid comprises synthetic nucleotide, synthetic nucleotide analog, nucleotide derivatives, and/or modified nucleotides.

The complementary strand nucleic acid, in some embodiments, comprises a nucleotide sequence (e.g., a spacer), for example, at or near the 5' end or 3' end, that hybridizes to a sequence in a target nucleic acid. In some embodiments, the spacer of a complementary strand nucleic acid interacts with a target nucleic acid in a sequence-specific manner via hybridization (i.e., base pairing). In some embodiments, the spacer sequence hybridizes to a target nucleic acid (e.g., protospacer sequence) that is located 5' or 3' of protospacer adjacent motif (PAM).

In some embodiments, a complementary strand nucleic acid comprises two separate nucleic acid molecules, which is referred to as a double complementary strand nucleic acid. In some embodiments, a complementary strand nucleic acid comprises a single nucleic acid molecule, which is referred to as a single complementary strand nucleic acid. In some embodiments, the complementary strand nucleic acid is a single complementary strand nucleic acid comprising a crRNA. In some embodiments, the complementary strand nucleic acid is a single complementary strand nucleic acid comprising a fused construct.

The nucleic acid-targeting region of a complementary strand nucleic acid, in some embodiments, comprises a nucleotide sequence that is complementary to a sequence in a target nucleic acid. The nucleic acid-targeting region, in some embodiments, comprises the spacer region. In some embodiments, the spacer region interacts with a target nucleic acid in a sequence-specific manner via hybridization (i.e., base pairing). The nucleotide sequence of a spacer region varies and determines the location within the target nucleic acid with which the complementary strand nucleic acid interacts. The spacer region of a complementary strand nucleic acid, in some embodiments, is modified to hybridize to any desired sequence within a target nucleic acid.

Complementarity is alternatively perfect or substantial/sufficient. Perfect complementarity between two nucleic acids means that the two nucleic acids form a duplex in which every base in the duplex is bonded to a complementary base by Watson-Crick pairing. Substantial or sufficient complementarity means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods.

In some embodiments, the nucleic acid-targeting region of a complementary strand nucleic acid (e.g., spacer region) is between 18 to 72 nucleotides in length. The nucleic acid-targeting region of a complementary strand nucleic acid (e.g., spacer region) has a length of from about 12 nucleotides to about 100 nucleotides. For example, the nucleic acid-targeting region of a complementary strand nucleic acid (e.g., spacer region) has a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, from about 12 nt to about 19 nt, from about 12 nt to about 18 nt, from about 12 nt to about 17 nt, from about 12 nt to about 16 nt, or from about 12 nt to about 15 nt. Alternatively, the DNA-targeting segment has a length of from about 18 nt to about 20 nt, from about 18 nt to about 25 nt, from about 18 nt to about 30 nt, from about 18 nt to about 35 nt, from about 18 nt to about 40 nt, from about 18 nt to about 45 nt, from about 18 nt to about 50 nt, from about 18 nt to about 60 nt, from about 18 nt to about 70 nt, from about 18 nt to about 80 nt, from about 18 nt to about 90 nt, from about 18 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

In some embodiments, the nucleic acid-targeting region of a complementary strand nucleic acid (e.g., spacer region) is 20 nucleotides in length. In some embodiments, the nucleic acid-targeting region of a complementary strand nucleic acid (e.g., spacer region) is 19 nucleotides in length. In some embodiments, the nucleic acid-targeting region of a complementary strand nucleic acid (e.g., spacer region) is 18 nucleotides in length. In some embodiments, the nucleic acid-targeting region of a complementary strand nucleic acid (e.g., spacer region) is 17 nucleotides in length. In some embodiments, the nucleic acid-targeting region of a complementary strand nucleic acid (e.g., spacer region) is 16 nucleotides in length. In some embodiments, the nucleic acid-targeting region of a complementary strand nucleic acid (e.g., spacer region) is 21 nucleotides in length. In some embodiments, the nucleic acid-targeting region of a complementary strand nucleic acid (e.g., spacer region) is 22 nucleotides in length.

A protospacer sequence, in some embodiments, is identified by identifying a PAM within a region of interest and selecting a region of a desired size upstream or downstream of the PAM as the protospacer. A corresponding spacer sequence is designed by determining the complementary sequence of the protospacer region.

A spacer sequence, in some embodiments, is identified using a computer program (e.g., machine readable code). The computer program, in some embodiments, uses variables such as predicted melting temperature, secondary structure formation, and predicted annealing temperature, sequence identity, genomic context, chromatin accessibility, % GC, frequency of genomic occurrence, methylation status, presence of SNPs, and the like.

The percent complementarity between the nucleic acid-targeting sequence (e.g., spacer sequence) and the nuclease recognition sequence within the target nucleic acid (e.g., protospacer), in some embodiments, is at least 60%, at least 70%, at least 75%, at least 80%, at least 85%, at least 90%, at least 95%, at least 97%, at least 98%, at least 99%, or 100%. The percent complementarity between the nucleic acid-targeting sequence and the nuclease recognition sequence within the target nucleic acid, in some embodiments, is at least 60% over about 20 contiguous nucleotides.

In some embodiments, complementary strand nucleic acids include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' poly-adenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); or a modification or sequence that provides a binding site for proteins (e.g., proteins that act on DNA, including transcriptional activators, transcriptional repressors, DNA methyl transferases, DNA demethylases, histone acetyltransferases, histone deacetylases, and combinations thereof).

Complementary strand nucleic acids are provided in any form. For example, in some embodiments, the complementary strand nucleic acid is provided in the form of RNA, either as two molecules (e.g., separate crRNA and tracrRNA) or as one molecule (e.g., sgRNA). In some embodiments, the complementary strand nucleic acid is provided in the form of a complex with a nuclease protein. Alternatively, the complementary strand nucleic acid is also provided in the form of DNA encoding the RNA. The DNA encoding the complementary strand nucleic acid alternatively encodes a single complementary strand nucleic acid (e.g., sgRNA) or separate RNA molecules (e.g., separate crRNA and tracrRNA). In the latter case, the DNA encoding the complementary strand nucleic acid is provided as separate DNA molecules encoding the crRNA and tracrRNA, respectively.

In some embodiments, DNAs encoding complementary strand nucleic acid are stably integrated in the genome of the cell and, optionally, operably linked to a promoter active in the cell. DNAs encoding complementary strand nucleic acids, in some embodiments, are operably linked to a promoter in an expression construct.

Complementary strand nucleic acids are prepared by any suitable method. For example, complementary strand nucleic acids are prepared by in vitro transcription using, for example, T7 RNA polymerase. In some embodiments, complementary strand nucleic acids are also synthetically produced molecules prepared by chemical synthesis.

Nucleases

In some embodiments, compositions disclosed herein comprise a nuclease. Nucleases recognizing a targeting sequence are known by those of skill in the art and include, but are not limited to, zinc finger nucleases (ZFN), transcription activator-like effector nucleases (TALEN), clustered regularly interspaced short palindromic repeats (CRISPR) nucleases, and meganucleases. Nucleases found in compositions and useful in methods disclosed herein are described in more detail below.

Zinc Finger Nucleases (ZFNs)

"Zinc finger nucleases" or "ZFNs" are a fusion between the cleavage domain of FokI and a DNA recognition domain containing 3 or more zinc finger motifs. The heterodimerization at a particular position in the DNA of two individual ZFNs in precise orientation and spacing leads to a double-strand break in the DNA. In some cases, ZFNs fuse a cleavage domain to the C-terminus of each zinc finger domain. In order to allow the two cleavage domains to dimerize and cleave DNA, the two individual ZFNs bind opposite strands of DNA with their C-termini at a certain distance apart. In some cases, linker sequences between the zinc finger domain and the cleavage domain require the 5' edge of each binding site to be separated by about 5-7 bp. Exemplary ZFNs that are useful in the present invention include, but are not limited to, those described in Urnov et al., Nature Reviews Genetics, 2010, 11:636-646; Gaj et al., Nat Methods, 2012, 9(8):805-7; U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140.

ZFNs, in some embodiments, generate a double-strand break in a target DNA, resulting in DNA break repair which allows for the introduction of gene modification. DNA break repair, in some embodiments, occurs via non-homologous end joining (NHEJ) or homology-directed repair (HDR). In some embodiments, a ZFN is a zinc finger nickase which, in some embodiments, is an engineered ZFN that induces site-specific single-strand DNA breaks or nicks. Descriptions of zinc finger nickases are found, e.g., in Ramirez et al., Nucl Acids Res, 2012, 40(12):5560-8; Kim et al., Genome Res, 2012, 22(7):1327-33.

TALENs

"TALENs" or "TAL-effector nucleases" are engineered transcription activator-like effector nucleases that contain a central domain of DNA-binding tandem repeats, a nuclear localization signal, and a C-terminal transcriptional activation domain. In some instances, a DNA-binding tandem repeat comprises 33-35 amino acids in length and contains two hypervariable amino acid residues at positions 12 and 13 that recognize one or more specific DNA base pairs. TALENs are produced by fusing a TAL effector DNA binding domain to a DNA cleavage domain. For instance, a TALE protein may be fused to a nuclease such as a wild-type or mutated FokII endonuclease or the catalytic domain of FokII. Several mutations to FokII have been made for its use in TALENs, which, for example, improve cleavage specificity or activity. Such TALENs are engineered to bind any desired DNA sequence.

TALENs are often used to generate gene modifications by creating a double-strand break in a target DNA sequence, which in turn, undergoes NHEJ or HDR. In some cases, a single-stranded donor DNA repair template is provided to promote HDR.

Detailed descriptions of TALENs and their uses for gene editing are found, e.g., in U.S. Pat. Nos. 8,440,431; 8,440,432; 8,450,471; 8,586,363; and 8,697,853; Scharenberg et al., Curr Gene Ther, 2013, 13(4):291-303; Gaj et al., Nat Methods, 2012, 9(8):805-7; Beurdeley et al., Nat Commun, 2013, 4:1762; and Joung and Sander, Nat Rev Mol Cell Biol, 2013, 14(1):49-55.

DNA Guided Nucleases

"DNA guided nucleases" are nucleases that use a single stranded DNA complementary nucleotide to direct the nuclease to the correct place in the genome by hybridizing to another nucleic acid, for example, the target nucleic acid in the genome of a cell. In some embodiments, the DNA guided nuclease comprises an Argonaute nuclease. In some embodiments, the DNA guided nuclease is selected from TtAgo, PfAgo, and NgAgo. In some embodiments, the DNA guided nuclease is NgAgo.

Meganucleases

"Meganucleases" are rare-cutting endonucleases or homing endonucleases that, in certain embodiments, are highly specific, recognizing DNA target sites ranging from at least 12 base pairs in length, e.g., from 12 to 40 base pairs or 12 to 60 base pairs in length. In some embodiments, meganucleases are modular DNA-binding nucleases, such as any fusion protein comprising at least one catalytic domain of an endonuclease and at least one DNA binding domain or protein specifying a nucleic acid target sequence. The DNA-binding domain, in some embodiments, contains at least one motif that recognizes single- or double-stranded DNA. The meganuclease is alternatively monomeric or dimeric.

In some instances, the meganuclease is naturally-occurring (found in nature) or wild-type, and in other instances, the meganuclease is non-natural, artificial, engineered, synthetic, rationally designed, or man-made. In certain embodiments, the meganuclease of the present invention includes an I-CreI meganuclease, I-CeuI meganuclease, I-MsoI meganuclease, I-SceI meganuclease, variants thereof, mutants thereof, and derivatives thereof.

Any meganuclease is contemplated to be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, 1-ZbiIP, PI-MtuI, PI-MtuHIP PI-MtuHIIP, PI-PfuI, PI-PfuII, PI-PkoI, P1-PkoII, PI-Rma43812IP, PI-SpBetaIP, PI-SceI, PI-TfuI, PI-TfuII, PI-ThyI, PI-TliI, PI-TliII, or any active variants or fragments thereof.

CRISPR

The CRISPR (Clustered Regularly Interspaced Short Palindromic Repeats)/Cas (CRISPR-associated protein) nuclease system is an engineered nuclease system based on a bacterial system that is used for genome engineering. It is based in part on the adaptive immune response of many bacteria and archaea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide the Cas (e.g., Cas9) nuclease to a region homologous to the crRNA in the target DNA called a "protospacer." The Cas (e.g., Cas9) nuclease cleaves the DNA to generate blunt ends at the double-strand break at sites specified by a 20-nucleotide complementary strand sequence contained within the crRNA transcript. The Cas (e.g., Cas9) nuclease, in some embodiments, requires both the crRNA and the tracrRNA for site-specific DNA recognition and cleavage. This system has now been engineered such that, in certain embodiments, the crRNA and tracrRNA are combined into one molecule (the "single guide RNA" or "sgRNA"), and the crRNA equivalent portion of the single guide RNA is engineered to guide the Cas (e.g., Cas9) nuclease to target any desired sequence (see, e.g., Jinek et al. (2012) Science 337:816-821; Jinek et al. (2013) eLife 2:e00471; Segal (2013) eLife 2:e00563). Thus, the CRISPR/Cas system can be engineered to create a double-strand break at a desired target in a genome of a cell, and harness the cell's endogenous mechanisms to repair the induced break by homology-directed repair (HDR) or nonhomologous end-joining (NHEJ).

In some embodiments, the Cas nuclease has DNA cleavage activity. The Cas nuclease, in some embodiments, directs cleavage of one or both strands at a location in a target DNA sequence. For example, in some embodiments, the Cas nuclease is a nickase having one or more inactivated catalytic domains that cleaves a single strand of a target DNA sequence.

Non-limiting examples of Cas nucleases include Cast, Cas1B, Cas2, Cas3, Cas4, Cas5, Cas6, Cas7, Cas8, Cas9 (also known as Csn1 and Csx12), Cas10, Cpf1, C2c3, C2c2 and C2c1Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, Csx10, Csx16, CsaX, Csx3, Csx1, Csx15, Csf1, Csf2, Csf3, Csf4, homologs thereof, variants thereof, mutants thereof, and derivatives thereof. There are three main types of Cas nucleases (type I, type II, and type III), and 10 subtypes including 5 type I, 3 type II, and 2 type III proteins (see, e.g., Hochstrasser and Doudna, *Trends Biochem Sci*, 2015:40(1): 58-66). Type II Cas nucleases include, but are not limited to, Cas1, Cas2, Csn2, and Cas9. These Cas nucleases are known to those skilled in the art. For example, the amino acid sequence of the *Streptococcus pyogenes* wild-type Cas9 polypeptide is set forth, e.g., in NBCI Ref. Seq. No. NP_269215, and the amino acid sequence of *Streptococcus thermophilus* wild-type Cas9 polypeptide is set forth, e.g., in NBCI Ref. Seq. No. WP_011681470.

Cas nucleases, e.g., Cas9 polypeptides, in some embodiments, are derived from a variety of bacterial species including, but not limited to, *Veillonella* atypical, *Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes,* and *Francisella novicida*.

"Cas9" refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target DNA) when both functional domains are active. The Cas9 enzyme, in some embodiments, comprises one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor,* and *Campylobacter*. In some embodiments, the Cas9 is a fusion protein, e.g. the two catalytic domains are derived from different bacteria species.

Useful variants of the Cas9 nuclease include a single inactive catalytic domain, such as a RuvC⁻ or HNH⁻ enzyme or a nickase. A Cas9 nickase has only one active functional domain and, in some embodiments, cuts only one strand of the target DNA, thereby creating a single strand break or nick. In some embodiments, the mutant Cas9 nuclease having at least a D10A mutation is a Cas9 nickase. In other embodiments, the mutant Cas9 nuclease having at least a H840A mutation is a Cas9 nickase. Other examples of mutations present in a Cas9 nickase include, without limitation, N854A and N863A. A double-strand break is introduced using a Cas9 nickase if at least two DNA-targeting RNAs that target opposite DNA strands are used. A double-nicked induced double-strand break is repaired by NHEJ or HDR. This gene editing strategy favors HDR and decreases the frequency of indel mutations at off-target DNA sites. The Cas9 nuclease or nickase, in some embodiments, is codon-optimized for the target cell or target organism.

In some embodiments, the Cas nuclease is a Cas9 polypeptide that contains two silencing mutations of the RuvC1 and HNH nuclease domains (D10A and H840A), which is referred to as dCas9. In one embodiment, the dCas9 polypeptide from *Streptococcus pyogenes* comprises at least one mutation at position D10, G12, G17, E762, H840, N854, N863, H982, H983, A984, D986, A987, or any combination thereof. Descriptions of such dCas9 polypeptides and variants thereof are provided in, for example, International Patent Publication No. WO 2013/176772. The dCas9 enzyme in some embodiments, contains a mutation at D10, E762, H983, or D986, as well as a mutation at H840 or N863. In some instances, the dCas9 enzyme contains a D10A or D10N mutation. Also, the dCas9 enzyme alternatively includes a mutation H840A, H840Y, or H840N. In some embodiments, the dCas9 enzyme of the present invention comprises D10A and H840A; D10A and H840Y; D10A and H840N; D10N and H840A; D10N and H840Y; or D10N and H840N substitutions. The substitutions are alternatively conservative or non-conservative substitutions to render the Cas9 polypeptide catalytically inactive and able to bind to target DNA.

For genome editing methods, the Cas nuclease in some embodiments comprises a Cas9 fusion protein such as a polypeptide comprising the catalytic domain of the type IIS restriction enzyme, FokII, linked to dCas9. The FokII-dCas9 fusion protein (fCas9) can use two guide RNAs to bind to a single strand of target DNA to generate a double-strand break.

Compositions for Delivery

Any suitable delivery method is contemplated to be used for delivering the compositions of the disclosure. The individual components of the HITI system (e.g., nuclease and/or the exogenous DNA sequence), in some embodiments, are delivered simultaneously or temporally separated. The choice of method of genetic modification is dependent on the type of cell being transformed and/or the circumstances under which the transformation is taking place (e.g., in vitro, ex vivo, or in vivo). A general discussion of these methods is found in Ausubel, et al., Short Protocols in Molecular Biology, 3rd ed., Wiley & Sons, 1995.

In some embodiments, a method as disclosed herein involves contacting a target DNA or introducing into a cell (or a population of cells) one or more nucleic acids comprising nucleotide sequences encoding a complementary strand nucleic acid (e.g., gRNA), a site-directed modifying polypeptide (e.g., Cas protein), and/or a exogenous DNA sequence. Suitable nucleic acids comprising nucleotide sequences encoding a complementary strand nucleic acid and/or a site-directed modifying polypeptide include expression vectors, where an expression vector comprising a nucleotide sequence encoding a complementary strand nucleic acid and/or a site-directed modifying polypeptide is a recombinant expression vector.

Non-limiting examples of delivery methods or transformation include, for example, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, and nanoparticle-mediated nucleic acid delivery (see, e.g., Panyam et. al., Adv Drug Deliv Rev. 2012 Sep. 13. pii: 50169-409X(12)00283-9. doi: 10.1016/j.addr.2012.09.023).

In some aspects, the present disclosure provides methods comprising delivering one or more polynucleotides, such as one or more vectors as described herein, one or more transcripts thereof, and/or one or more proteins transcribed therefrom, to a host cell. In some aspects, the disclosure further provides cells produced by such methods, and organisms (such as animals, plants, or fungi) comprising or produced from such cells. In some embodiments, a nuclease protein in combination with, and optionally complexed with, a complementary strand sequence is delivered to a cell. Conventional viral and non-viral based gene transfer methods are contemplated to be used to introduce nucleic acids in mammalian cells or target tissues. Such methods are used to administer nucleic acids encoding components of a HITI system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems can include DNA and RNA viruses, which can have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon. TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids can include lipofection, nucleofection, microinjection, electroporation, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery is contemplated to be to cells (e.g. in vitro or ex vivo administration) or target tissues (e.g. in vivo administration).

The preparation of lipid:nucleic acid complexes, including targeted liposomes such as immunolipid complexes, is well known (see, e.g., Crystal, Science 270:404-410 (1995); Blaese et al., Cancer Gene Ther. 2:291-297 (1995): Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

RNA or DNA viral based systems are used to target specific cells in the body and trafficking the viral payload to the nucleus of the cell. Viral vectors are alternatively administered directly (in vivo) or they are used to treat cells in vitro, and the modified cells are optionally be administered (ex vivo). Viral based systems include, but are not limited to, retroviral, lentivirus, adenoviral, adeno-associated, and herpes simplex virus vectors for gene transfer. Integration in the host genome, in some embodiments, occurs with the retrovirus, lentivirus, and adeno-associated virus gene transfer methods, which results in long term expression of the inserted transgene, in some embodiments. High transduction efficiencies are observed in many different cell types and target tissues.

The tropism of a retrovirus is altered, in certain embodiments, by incorporating foreign envelope proteins, expanding the potential target population of target cells. Lentiviral vectors are retroviral vectors that are capable of transducing or infecting non-dividing cells and produce high viral titers. Selection of a retroviral gene transfer system depends on the target tissue. Retroviral vectors, in some embodiments, comprise cis-acting long terminal repeats with packaging capacity for up to 6-10 kb of foreign sequence. The minimum cis-acting LTRs, in some embodiments, are sufficient for replication and packaging of the vectors, which are capable of integrating the therapeutic gene into the target cell to provide permanent transgene expression. Retroviral vectors include but are not limited to those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In some embodiments, adenoviral-based systems are used. Adenoviral-based systems, in some embodiments, lead to transient expression of the transgene. Adenoviral based vectors are capable of high transduction efficiency in cells and in some embodiments do not require cell division. High titer and levels of expression are possible with adenoviral based vectors. In some embodiments, adeno-associated virus ("AAV") vectors are used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells, in some embodiments, are used to form virus particles capable of infecting a host cell. Such cells include but are not limited to 293 cells, (e.g., for packaging adenovirus), and .psi.2 cells or PA317 cells (e.g., for packaging retrovirus). Viral vectors are generated by producing a cell line that packages a nucleic acid vector into a viral particle. In some cases, the vectors contain the minimal viral sequences required for packaging and subsequent integration into a host. In some cases, the vectors contain other viral sequences being replaced by an expression cassette for the polynucleotide(s) to be expressed. In some embodiments, the missing viral functions are supplied in trans by the packaging cell line. For example, in some embodiments, AAV vectors comprise ITR sequences from the AAV genome which are required for packaging and integration into the host genome. Viral DNA is packaged in a cell line, which contains a helper plasmid encoding the other AAV genes, namely rep and cap, while lacking ITR sequences. Alternatively, the cell line is infected with adenovirus as a helper. The helper virus promotes replication of the AAV vector and expression of AAV genes from the helper plasmid. Contamination with adenovirus is reduced by, e.g., heat treatment, to which adenovirus is more sensitive than AAV.

A host cell is alternatively transiently or non-transiently transfected with one or more vectors described herein. In some embodiments, a cell is transfected as it naturally occurs in a subject. In some embodiments, a cell is taken or derived from a subject and transfected. In some embodiments, a cell is derived from cells taken from a subject, such as a cell line. In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence.

Any suitable vector compatible with the host cell is contemplated to be used with the methods of the invention. Non-limiting examples of vectors for eukaryotic host cells include pXT1, pSG5, pSVK3, pBPV, pMSG, and pSVLSV40.

In some embodiments, a nucleotide sequence encoding a complementary strand nucleic acid and/or a site-directed modifying polypeptide is operably linked to a control element, e.g., a transcriptional control element, such as a promoter. The transcriptional control element is functional, in some embodiments, in either a eukaryotic cell, e.g., a mammalian cell, or a prokaryotic cell (e.g., bacterial or archaeal cell). In some embodiments, a nucleotide sequence encoding a complementary strand nucleic acid and/or a site-directed modifying polypeptide is operably linked to multiple control elements that allow expression of the nucleotide sequence encoding a complementary strand nucleic acid and/or a site-directed modifying polypeptide in prokaryotic and/or eukaryotic cells.

Depending on the host/vector system utilized, any of a number of suitable transcription and translation control elements, including constitutive and inducible promoters, transcription enhancer elements, transcription terminators, etc. may be used in the expression vector (e.g., U6 promoter, H1 promoter, etc.; see above) (see e.g., Bitter et al. (1987) Methods in Enzymology, 153:516-544).

In some embodiments, a complementary strand nucleic acid and/or a site-directed modifying polypeptide is provided as RNA. In such cases, the complementary strand nucleic acid and/or the RNA encoding the site-directed modifying polypeptide is produced by direct chemical synthesis or may be transcribed in vitro from a DNA encoding the complementary strand nucleic acid. The complementary strand nucleic acid and/or the RNA encoding the site-directed modifying polypeptide are synthesized in vitro using an RNA polymerase enzyme (e.g., T7 polymerase, T3 polymerase, SP6 polymerase, etc.). Once synthesized, the RNA directly contacts a target DNA or is introduced into a cell using any suitable technique for introducing nucleic acids into cells (e.g., microinjection, electroporation, transfection, etc).

Nucleotides encoding a complementary strand nucleic acid (introduced either as DNA or RNA) and/or a site-directed modifying polypeptide (introduced as DNA or RNA) and/or an exogenous DNA sequence are provided to the cells using a suitable transfection technique; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. Nucleic acids encoding a complementary strand nucleic acid and/or a site-directed modifying polypeptide and/or a chimeric site-directed modifying polypeptide and/or an exogenous DNA sequence may be provided on DNA vectors. Many vectors, e.g., plasmids, cosmids, minicircles, phage, viruses, etc., useful for transferring nucleic acids into target cells are available. The vectors comprising the nucleic acid(s) in some embodiments are maintained episomally, e.g. as plasmids, minicircle DNAs, viruses such cytomegalovirus, adenovirus, etc., or they are integrated into the target cell genome, through homologous recombination or random integration, e.g. retrovirus-derived vectors such as MMLV, HIV-1, and ALV.

Methods of Making Changes to Genomic DNA

Provided herein are homology-independent targeted integration (HITI) methods and compositions for making changes to nucleic acid, such as genomic DNA, including genomic DNA in non-dividing or terminally differentiated cells that do not divide. Methods herein, at least in some embodiments, are homology independent, using non-homologous end-joining to insert exogenous DNA into a target DNA, such as a genomic DNA of a cell, such as a non-dividing or terminally differentiated cell. In some embodiments, methods herein comprise a method of integrating an exogenous DNA sequence into a genome of a non-dividing cell comprising contacting the non-dividing cell with a composition comprising a targeting construct comprising the exogenous DNA sequence and a targeting sequence, a complementary strand oligonucleotide homologous to the targeting sequence, and a nuclease, wherein the exogenous DNA sequence comprises at least one nucleotide difference compared to the genome and the targeting sequence is recognized by the nuclease.

In some embodiments of HITI methods disclosed herein, exogenous DNA sequences are fragments of DNA containing the desired sequence to be inserted into the genome of the target cell or host cell. At least a portion of the exogenous DNA sequence has a sequence homologous to a portion of the genome of the target cell or host cell and at least a portion of the exogenous DNA sequence has a sequence not homologous to a portion of the genome of the target cell or host cell. For example, in some embodiments, the exogenous DNA sequence may comprise a portion of a host cell genomic DNA sequence with a mutation therein. Therefore, when the exogenous DNA sequence is integrated into the genome of the host cell or target cell, the mutation found in the exogenous DNA sequence is carried into the host cell or target cell genome.

In some embodiments of HITI methods disclosed herein, the exogenous DNA sequence is flanked by at least one targeting sequence. In some embodiments, the exogenous DNA sequence is flanked by two targeting sequences. The targeting sequence comprises a specific DNA sequence that is recognized by at least one nuclease. In some embodiments, the targeting sequence is recognized by the nuclease in the presence of a complementary strand oligonucleotide having a homologous sequence to the targeting sequence.

In some embodiments, in HITI methods disclosed herein, a targeting sequence comprises a nucleotide sequence that is recognized and cleaved by a nuclease. Nucleases recognizing a targeting sequence are known by those of skill in the art and include but are not limited to zinc finger nucleases (ZFN), transcription activator-like effector nucleases (TALEN), and clustered regularly interspaced short palindromic repeats (CRISPR) nucleases. ZFNs, in some embodiments, comprise a zinc finger DNA-binding domain and a DNA cleavage domain, fused together to create a sequence specific nuclease. TALENs, in some embodiments, comprise a TAL effector DNA binding domain and a DNA cleavage domain, fused together to create a sequence specific nuclease. CRISPR nucleases, in some embodiments, are naturally occurring nucleases that recognize DNA sequences homologous to clustered regularly interspaced short palindromic repeats, commonly found in prokaryotic DNA. CRISPR nucleases include, but are not limited to, Cas9 Cpf1, C2c3, C2c2, and C2c1.

HITI methods disclosed herein, in some embodiments, are capable of introducing mutations into a host genome or a target genome as well as repairing mutations in a host genome or a target genome. Mutations or wild-type sequences, in some embodiments of the methods described herein, are found in the exogenous DNA sequence to be inserted into the host genome or target genome. Mutations are known by those of skill in the art and include single base-pair changes or point mutations, insertions, and deletions. In some embodiments, a single base-pair change results in a missense mutation which creates a codon that encodes a different amino acid in transcribed mRNA than the wild-type sequence. In some embodiments, a single base-pair change results in a nonsense mutation which encodes for a stop codon in transcribed mRNA. In some embodiments, a stop codon in transcribed RNA results in early truncation of a protein translated from the mRNA. In some embodiments, a single base-pair change results in a silent mutation that does not result in any change in amino acids encoded by a mRNA transcribed from the host genome or the target genome. In some embodiments, a silent mutation is in an intron. In some embodiments, a silent mutation is in an exon and creates a codon encoding for the same amino acid as the wild-type sequence. In some embodiments, a silent mutation, is in a promoter, an enhancer, a 5' UTR, a 3' UTR, or other non-coding region of the host genome or target genome. In some embodiments, a silent mutation results in aberrant splicing of an mRNA transcript. In some embodiments, a silent mutation disrupts a RNA splice donor or splice acceptor site. In some embodiments, a silent mutation results in aberrant RNA export. In some embodiments, a silent mutation results in aberrant or reduced translation of an mRNA. In some embodiments, a silent mutation results in aberrant or reduced transcription of an RNA. In some embodiments, mutations comprise insertions into the host genome or target genome. In some embodiments, insertions comprise a specific number of nucleotides ranging from 1 to 1,000,000 base pairs, for example 1-10, 5-20, 15-30, 20-50, 40-80, 50-100, 100-1000, 500-2000, 1000-5000, 2000-8000, 5000-10000, 10000-50000, 50000-100000, 100000-120000, 120000-150000, 150000-300000, 250000-500000, 400000-800000, or 500000-1000000 base pairs. In some embodiments, deletions comprise a specific number of nucleotides ranging from 1 to 10,000 base pairs. In some embodiments, the method comprises eliminating at least one gene, or fragment thereof, from the host genome or target genome. In some embodiments, the method comprises introducing an exogenous gene, or fragment thereof, into the host genome or target genome. In some embodiments, the method comprises replacing a mutated gene, or fragment thereof, in the host genome or target genome with a wild-type gene, or fragment thereof. In some embodiments, the method changes at least one nucleotide of a host genome or target genome resulting in increased expression of a gene. In some embodiments, the method changes at least one nucleotide of a host genome or target genome resulting in decreased expression of a gene. In some embodiments, the method introduces an exogenous promoter into the host genome or target genome resulting in altered expression of a gene. In some embodiments, the promoter is an inducible promoter.

HITI methods disclosed herein have increased capabilities in making changes to genomic DNA in non-dividing cells currently not accessible to current methods of making changes to genomic DNA. Non-dividing cells are present in high numbers in fully developed organisms and in terminally differentiated cells or quiescent stem cells. Non-dividing cells include, but are not limited to: cells in the central nervous system including neurons, oligodendrocytes, microglia and ependymal cells; sensory transducer cells; autonomic neuron cells; sense organ and peripheral neuron supporting cells; cells in the retina including photoreceptors, rods and cones; cells in the kidney including parietal cells, glomerulus podocytes, proximal tubule brush border cells, loop of henle thin segment cells, distal tubule cells, collecting duct cells; cells in the hematopoietic lineage including lymphocytes, monocytes, neutrophils, eosinophils, basophils, thrombocytes; cells of liver including hepatocytes, stellate cells, the Kupffer cells and the liver endothelial cells; pancreatic endocrine cells including alpha, beta, delta, gamma, and epsilon cells; cells of the respiratory epithelium including ciliated cells, basal cells, goblet cells and alveolar cells, germ cells including oogonium/oocyte, spermatid, spermatocyte, spermatogonium cell and spermatozoon; cells of the bone including osteocytes, osteoclasts and osteoblasts; cells of the heart including cardiomyocytes and cardiac pacemaker cells; follicular cells in the thyroid; cells in the upper digestive tract including serous cells, mucous cells and taste buds; cells in the stomach including parietal cells, chief cells, enteroendocrine cells; endothelial cells, epithelial cells, adipocytes, bone marrow cells, inner ear cells, dermis cells, smooth muscle cells, skeletal muscle cells. In some embodiments, HITI methods disclosed herein provide a method of making changes to genomic DNA in dividing cells, wherein the method has higher efficiency than previous methods disclosed in the art. Dividing cells include, but are not limited to, hematopoietic stem cells, mesenchymal stem cells, neural stem cells, liver stem cells, muscle satellite cells, epidermis cells, glial cells, and astrocytes.

In some embodiments, the targeting construct, the complementary strand oligonucleotides, and/or a polynucleotide encoding the nuclease for HITI methods described herein are introduced into the target cell or the host cell by a virus. Viruses, in some embodiments, infect the target cell and express the targeting construct, the complementary strand oligonucleotides, and the nuclease, which allows the exogenous DNA of the targeting construct to be integrated into the host genome. In some embodiments, the virus comprises a sendai virus, a retrovirus, a lentivirus, a baculovirus, an adenovirus, or an adeno-associated virus. In some embodiments the virus is a pseudotyped virus. In some embodiments, the targeting construct, the complementary strand oligonucleotides, and/or a polynucleotide encoding the nuclease for HITI methods described herein are introduced into the target cell or the host cell by a non-viral gene delivery method. Non-viral gene delivery methods, in some embodiments, deliver the genetic materials (including DNA, RNA and protein) into the target cell and express the targeting construct, the complementary strand oligonucleotides, and the nuclease, which allows the exogenous DNA of the targeting construct to be integrated into the host genome. In some embodiments, the non-viral method comprises transfection reagent (including nanoparticles) for DNA mRNA or protein, or electroporation.

Methods of Treating Disease

Also provided herein are methods and compositions for treating disease, such as genetic disease. Genetic diseases are those that are caused by mutations in inherited DNA. In some embodiments, genetic diseases are caused by mutations in genomic DNA. Genetic mutations are known by those of skill in the art and include, single base-pair changes or point mutations, insertions, and deletions. In some embodiments, methods provided herein include a method of treating a genetic disease in a subject in need thereof, wherein the genetic disease results from a mutated gene having at least one changed nucleotide compared to a wild-type gene, wherein the method comprises contacting at least one cell of the subject with a composition comprising a targeting construct comprising a DNA sequence homologous to the wild-type gene and a targeting sequence, a complementary strand oligonucleotide homologous to the targeting sequence, and a nuclease, wherein the targeting sequence is recognized by the nuclease such that the mutated gene, or fragment thereof, is replaced with the wild-type gene, or fragment thereof.

Genetic diseases that are treated by methods disclosed herein include but are not limited to aceruloplasminemia, Achondrogenesis type II, achondroplasia, acute intermittent porphyria, adenylosuccinate lyase deficiency, Adrenoleukodystrophy, ALA dehydratase deficiency, Alagille syndrome, Albinism, Alexander disease, alkaptonuria, alpha 1-antitrypsin deficiency, Alström syndrome, Alzheimer's disease, Amelogenesis imperfecta, amyotrophic lateral sclerosis, androgen insensitivity syndrome, Anemia, Angelman syndrome, Apert syndrome, ataxia telangiectasia, Beare-Stevenson cutis gyrata syndrome, Benjamin syndrome, beta-thalassemia, biotinidase deficiency, bladder cancer, Bloom syndrome, Bone diseases, breast cancer, Birt-Hogg-Dubé syndrome, CADASIL syndrome, CGD Chronic granulomatous disorder, Campomelic dysplasia, Canavan disease, Cancer, Charcot-Marie-Tooth disease, CHARGE syndrome, Cockayne syndrome, Coffin-Lowry syndrome, collagenopathy, types II and XI, Colorectal cancer, Connective tissue disease, Cowden syndrome, Cri du chat, Crohn's disease (fibrostenosing), Crouzon syndrome, Crouzonodermoskeletal syndrome, Degenerative nerve diseases, developmental disabilities, Di George's syndrome, distal hereditary motor neuropathy, Dwarfism, Ehlers-Danlos syndrome, erythropoietic protoporphyria, Fabry disease, Facial injuries and disorders, factor V Leiden thrombophilia, familial adenomatous polyposis, familial dysautonomia, FG syndrome, fragile X syndrome, Friedreich's ataxia, G6PD deficiency, galactosemia, Gaucher disease, Genetic brain disorders, Harlequin type ichthyosis, Head and brain malformations, Hearing disorders and deafness, Hearing problems in children, hemochromatosis, hemophilia, hepatoerythropoietic porphyria, Hereditary coproporphyria, Hereditary hemorrhagic telangiectasia (HHT), Hereditary multiple exostoses, Hereditary nonpolyposis colorectal cancer, homocystinuria, Huntington's disease, primary hyperoxaluria, hyperphenylalaninemia, Hypochondrogenesis, Hypochondroplasia, Incontinentia pigmenti, infantile-onset ascending hereditary spastic paralysis, Infertility, Jackson-Weiss syndrome, Joubert syndrome, Klinefelter syndrome, Leber's congenital amaurosis, Kniest dysplasia, Krabbe disease, Lesch-Nyhan syndrome, Leukodystrophies, Li-Fraumeni syndrome, familial lipoprotein lipase deficiency, Male genital disorders, Marfan syndrome, McCune-Albright syndrome, McLeod syndrome, MEDNIK, Familial Mediterranean fever, Menkes disease, Metabolic disorders, Methemoglobinemia beta-globin type, methylmalonic academia, Micro syndrome, Microcephaly, Movement disorders, Mowat-Wilson syndrome, Mucopolysaccharidosis (MPS I), Muenke syndrome, Muscular dystrophy, Muscular dystrophy, Duchenne and Becker type, myotonic dystrophy, Neurofibromatosis type I, Neurofibromatosis type II, Neurologic diseases, Neuromuscular disorders, Sphingomyelin phosphodiesterase 1SMPD1, nonsyndromic deafness, Noonan syndrome, Ogden syndrome, osteogenesis imperfecta, otospondylomegaepiphyseal dysplasia, pantothenate kinase-associated neurodegeneration, Pendred syndrome, Peutz-Jeghers syndrome, Pfeiffer syndrome, phenylketonuria, Polycystic kidney disease, porphyria, Prader-Willi syndrome, Primary ciliary dyskinesia (PCD), primary pulmonary hypertension, progeria, propionic academia, protein C deficiency, protein S deficiency, pseudo-Gaucher disease, pseudoxanthoma elasticum, Retinal disorders, Retinoblastoma, Rett syndrome, Rubinstein-Taybi syndrome, Schwartz-Jampel syndrome, severe achondroplasia with developmental delay and acanthosis nigricans (SADDAN), sickle cell anemia, Siderius X-linked mental retardation syndrome, Skin pigmentation disorders, Smith-Lemli-Opitz syndrome, Smith Magenis Syndrome, Speech and communication disorders, spinal and bulbar muscular atrophy, Spinal Muscular Atrophy, Stargardt disease, spinocerebellar ataxia, Strudwick type spondyloepimetaphyseal dysplasia, spondyloepiphyseal dysplasia congenital, Stickler syndrome, Tay-Sachs disease, tetrahydrobiopterin deficiency, thanatophoric dysplasia, Thyroid disease, Treacher Collins syndrome, Usher syndrome, variegate porphyria, von Hippel-Lindau disease, Waardenburg syndrome, Weissenbacher-Zweymilller syndrome, Williams Syndrome, Wilson disease, Wolf-Hirschhorn syndrome, Xeroderma pigmentosum, X-linked severe combined immunodeficiency, or X-linked sideroblastic anemia.

Methods of treating genetic disease disclosed herein employ exogenous DNA sequences comprising at least a portion of a wild type DNA sequence that corresponds to the DNA sequence of mutated gene, so that in the method, the mutated DNA sequence is replaced with the wild type DNA sequence. In some embodiments, the exogenous DNA sequence comprises 100 base pairs of wild type DNA sequence. In some embodiments, the exogenous DNA sequence comprises 200 base pairs of wild type DNA sequence.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "genome editing" refers to a type of genetic engineering in which DNA is inserted, replaced, or removed from a target DNA, e.g. the genome of a cell, using one or more nucleases and/or nickases. The nucleases create specific double-strand breaks (DSBs) at desired locations in the genome, and harness the cell's endogenous mechanisms to repair the induced break by nonhomologous end joining (NHEJ). The nickases create specific single-strand breaks at desired locations in the genome. In one non-limiting example, two nickases can be used to create two single strand breaks on opposite strands of a target DNA, thereby generating a blunt or a sticky end. Any suitable nuclease can be introduced into a cell to induce genome editing of a target DNA sequence including, but not limited to, CRISPR-associated protein (Cas) nucleases, zinc finger nucleases (ZFNs), transcription activator-like effector nucleases (TALENs), meganucleases, other endo- or exo-nucleases, variants thereof, fragments thereof, and combinations thereof.

The term "homology-directed repair" or "HDR" refers to a mechanism in cells to accurately and precisely repair double-strand DNA breaks using a homologous template to guide repair. The most common form of HDR is homologous recombination (HR), a type of genetic recombination in which nucleotide sequences are exchanged between two similar or identical molecules of DNA.

The term "nonhomologous end joining" or "NHEJ" refers to a pathway that repairs double-strand DNA breaks in which the break ends are directly ligated without the need for a homologous template.

The term "nucleic acid," "nucleotide," or "polynucleotide" refers to deoxyribonucleic acids (DNA), ribonucleic acids (RNA) and polymers thereof in either single, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic, or derivatized nucleotide bases. In some embodiments, a nucleic acid can comprise a mixture of DNA, RNA, and analogs thereof. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, and mRNA encoded by a gene.

The term "gene" or "nucleotide sequence encoding a polypeptide" means the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

A "recombinant expression vector" is a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant protein produced from the expression vector.

"Recombinant" refers to a genetically modified polynucleotide, polypeptide, cell, tissue, or organism. For example, a recombinant polynucleotide (or a copy or complement of a recombinant polynucleotide) is one that has been manipulated using well known methods. A recombinant expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, New York, (1989) or Current Protocols in Molecular Biology Volumes 1-3, John Wiley & Sons, Inc. (1994-1998)). A recombinant expression cassette (or expression vector) typically comprises polynucleotides in combinations that are not found in nature. For instance, human manipulated restriction sites or plasmid vector sequences can flank or separate the promoter from other sequences. A recombinant protein is one that is expressed from a recombinant polynucleotide, and recombinant cells, tissues, and organisms are those that comprise recombinant sequences (polynucleotide and/or polypeptide).

The term "single nucleotide polymorphism" or "SNP" refers to a change of a single nucleotide with a polynucleotide, including within an allele. This can include the replacement of one nucleotide by another, as well as deletion or insertion of a single nucleotide. Most typically, SNPs are biallelic markers although tri- and tetra-allelic markers can also exist. By way of non-limiting example, a nucleic acid molecule comprising SNP A\C may include a C or A at the polymorphic position.

The terms "subject," "patient," and "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

As used herein, the term "administering" includes oral administration, topical contact, administration as a suppository, intravenous, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "sufficient amount" refers to the amount of an agent (e.g., DNA nuclease, etc.) that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

The term "pharmaceutically acceptable carrier" refers to a substance that aids the administration of an agent (e.g., DNA nuclease, etc.) to a cell, an organism, or a subject. "Pharmaceutically acceptable carrier" refers to a carrier or excipient that can be included in a composition or formulation and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical carriers are useful in the present invention.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Methods

Plasmids. Vectors expressing both gRNA and mCherry (pCAGmCherry-gRNA) were generated. To construct gRNA expression vectors, each 20 bp target sequence was sub-cloned into pCAGmCherry-gRNA or gRNA_Cloning Vector (Addgene 41824). pMDLg/pRRE, pRSV-Rev and pMD2.G (Addgene 12251, 12253 and 12259) were used for packaging lentiviruses. pEGIP*35 and tGFP (Addgene 26776 and 26864) were used for examining HDR and HITI efficiencies. To construct IRESmCherry-0c, IRESmCherry-1c, and IRESmCherry-2c, IRES and mCherry sequence were amplified with Cas9 target sequence by PCR from pEGIP*35 and pCAGmCherry-gRNA, respectively and co-integrated into pCR-bluntII vector (Invitrogen). To generate different NLS-dCas9 constructs, pMSCV-LTR-dCas9-VP64-BFP (Addgene 46912) was used to amplify dCas9, which was subsequently subcloned into pCAG-containing plasmid with different NLS and 3xFlag tag. To construct pCAG-Cas9(no NLS), pCAG-1NLS-Cas9-1NLS, and pCAG-1BPNLS-Cas9-1BPNLS, D10A and H840A mutations of dCas9 plasmids were exchanged to wild type sequence by In-Fusion HD Cloning kit (Clontech). Then, pCAG-Cas9-2AGFP (no NLS), pCAG-1NLS-Cas9-1NLS-2AGFP, and pCAG-1BPNLS-Cas9-1BPNLS-2AGFP were constructed by adding 2AGFP to the downstream of Cas9. To construct pCAG-floxSTOP-1BPNLS-Cas9-1BPNLS, 1BPNLS-Cas9-1BPNLS was amplified by PCR and exchanged to GFP of pCAG-floxSTOP-EGFP-N1 vector. To construct HITI donor plasmids for mouse and human Tubb3 gene (Tubb3-1c, Tubb3-2c, hTUBB3-1c, and hTUBB3-2c), GFP were subcloned into pCAG-floxSTOP plasmid with one or two CAS9/gRNA target sequence. To construct HDR donor for mouse Tubb3 gene (Tubb3-HR), GFP, 5' and 3' homology arms were amplified from pCAG-GFP-N1 or mouse genome, then subcloned into pCAG-floxSTOP plasmid. pCAG-ERT2-Cre-ERT2 was purchased from Addgene (13777). PX551 and PX552 were purchased from Addgene (60957 and 60958). To construct AAV-Cas9, nEF (hybrid EF1α/HTLV) promoter (Invivogen) was exchanged to Mecp2 promoter of PX551. To construct donor/gRNA AAVs, donor DNA sandwiched by Cas9/gRNA target sequence, gRNA expression cassette and GFPKASH (or mCherryKASH) expression cassettes were subcloned between ITRs of PX552.

Genomic DNA extraction and genomic PCR. All of the genomic DNA was extracted using Blood & Tissue kit (QIAGEN) or PicoPure DNA Extraction Kit (Thermo Fisher Scientific). All of the genomic PCR were done with Prime-STAR GXL DNA polymerase (Takara).

Bisulfite sequencing. Genomic DNA from the transfected HEK293 lines was extracted and bisulfite converted using the Zymo EZ DNA Methylation-direct Kit (Zymo Research). The DNA methylation profile of a previously described region of the mCherry was analyzed by TOPO cloning as described previously (Liu, G.-H. G. et al. Targeted gene correction of laminopathy-associated LMNA mutations in patient-specific iPSCs. Cell Stem Cell 8, 688-694 (2011)).

Cell lines. H1 hESC was purchased from WiCell Research, and maintained in hESC medium (Liu, G.-H. G. et al Recapitulation of premature ageing with iPSCs from Hutchinson-Gilford progeria syndrome. Nature 472, 221-225 (2011). HEK293 cells were purchased from ATCC.

AAV production. All of AAVs were packaged with serotype 8 or serotype 9.

Animals. ICR, C57BL/6 and ROSA$^{LSL-tdTomato/LSL-tdTomato}$ mice (known as Ai14 mouse, Madisen, L. et al. A robust and high-throughput Cre reporting and characterization system for the whole mouse brain. Nat Neurosci 13, 133-140 (2009)) were purchased from the Jackson laboratory. Some of pregnant ICR mice were purchased from SLC Japan (Sizuoka, Japan). RCS and Brown Norway rats were purchased from the Jackson laboratory. All mice used in this study were from mixed gender, mixed strains and P1 to 12 weeks old. All mouse experiments were approved by the IACUC committee or the RIKEN Center for Developmental Biology and conform to regulatory standards. All rat procedures were conducted with the approval and under the supervision of the Institutional Animal Care Committee at the University of California San Diego and adhered to the ARVO Statement for the Use of Animals in Ophthalmic and Vision Research. The midday of the vaginal plug was designated as embryonic day 0.5 (E0.5).

Minicircle DNA vectors. Construction and production of minicircle DNA vectors were performed as previously described Kay, M. A., He, C.-Y. & Chen, Z.-Y. A robust system for production of minicircle DNA vectors. Nature Biotechnology 28, 1287-1289 (2010). Briefly, to construct pre-minicircle plasmids (pIRESmCherry-MC, pTubb3-MC, phTUBB3-MC, pAi14-GFP-MC, and pAi14-luc-MC), IRESmCherry, GFP, or luciferase genes with Cas9/gRNA targeting sequence were cloned into ApaI and SmaI sites of the minicircle producer plasmid pMC.BESPX. The final minicircle constructs were introduced into the E. coli strain 3S2T and amplified overnight in Terrific Broth (pH7.0) (Fisher Scientific). The minicircle production was induced by mixing the overnight TB culture with an equal volume of minicircle induction mix comprising fresh LB and 20% L-arabinose (SBI), followed by a 5 h incubation at 32° C. with shaking at 250 rpm. Minicircle DNA was isolated with EndoFree Plasmid Mega Kit (QIAGEN) following the manufacturer's protocol except that the volumes of P1, P2 and P3 buffers were doubled.

Surveyor assay. To examine the efficacy of the generated nuclear localized Cas9, a Surveyor assay was performed in human H1 ESCs. Briefly, each 1.5×10 7 feeder-free cultured H1 ESCs were dissociated by TrypLE (Invitrogen), and resuspended in 1 ml of MEF-conditioned medium containing 10 µM ROCK inhibitor Y-27632 (Biomol Inc.). Cells were electroporated with 25 µg of pCAGmCherry-KCNQ1 and 25 µg of different Cas9 (pCAG-Cas9-2AGFP, pCAG-1NLS-Cas9-1NLS-2AGFP, or pCAG-1BPNLS-Cas9-1BPNLS-2AGFP), and were plated onto 100 mm dishes pre-coated with Matrigel. Two days after electroporation, the cells were dissociated by TrypLE, and Cas9 and gRNA expressing cells were sorted out as GFP/mCherry double positive cells by BD influx cell sorter (BD), and extracted genomic DNA with DNeasy Blood & Tissue kit (QIAGEN), which is used for Surveyor assay as described previously Sanjana, N. E. et al A transcription activator-like effector toolbox for genome engineering. *Nature Protocols* 7, 171-192 (2012).

Generation of HEK293 GFP-correction line. To assess the efficiency of targeted gene modification by HDR and HITI in dividing cells, a mutated GFP gene-based reporter system was established in HEK293. Briefly, pEGIP*35 was co-transfected with pMDLg/pRRE, pRSV-Rev and pMD2.G, packaged and purified as lentiviral vectors according to a published protocol Kutner, R. H., Zhang, X.-Y. & Reiser, J. Production, concentration and titration of pseudotyped HIV-1-based lentiviral vectors. *Nature Protocols* 4, 495-505 (2009). HEK293 cells were transduced in suspension with lentiviral EGIP*35 vector and 4 µg/ml polybrene for 1 h. After brief centrifugation to remove any residual lentiviral vector, the cells were seeded in 100 mm dishes. Three days after transduction, puromycin (1-2 µg/ml; Invitrogen) was added to the medium. After 10 days, single colonies were individually picked up and expanded as HEK293 GFP-correction line.

Culture of mouse primary neurons. Primary cultures of neurons were obtained from brain cortex of E15.5 days-old mice. After the embryo retrieval, all dissection procedures were performed in a cold solution of 1× phosphate-buffered saline (PBS) with 2% glucose (Gibco). Cortical tissue was dissociated by trypsinization, and $1.5 \times 10^5$ cells/cm 2 were plated over coated poly-D-lysine coverslips (Neuvitro) with Neurobasal media (Gibco) supplemented with 2% B27 (Gibco) and 0.25% Glutamax TM-I 100X (Gibco). The cultures were incubated at standard conditions (37° C. in humidified 5% CO2/95% air atmosphere). Half volume of culture media was replaced every 3 days.

Differentiation and Culture of human ESC-derived pan neurons. The differentiation protocol from human ESC to pan neuron was performed using methods routinely used by those of skill in the art.

Transfection of in vitro cultured cells. Lipofectamine 3000 (Invitrogen), CombiMag Reagent (OZBiosciences), and DNA-In Neuro Transfection Regent (Amsbio) were used for transfection of HEK293 cells, mouse primary cells, and human ESC derived pan neurons, respectively. Transfection complexes were prepared following the manufacturer instructions.

Immunocytochemistry of primary neurons. Cells were fixed in 4% paraformaldehyde (PFA) at room temperature for 15 min. Then cells were blocked and permeabilized with 5% Bovine Serum Albumin (BSA) and 0.1% Triton X-100 in PBS during 50 min shaking at room temperature. Primary antibodies were incubated in 2.5% BSA/PBS overnight at 4° C. in a wet chamber with anti-GFP (Ayes) and anti-βIII tubulin (Sigma) antibodies. Next day, cells were washed with 0.2% Tween 20 in PBS, and incubated 1 h at room temperature with the secondary antibodies Alexa fluor 488 (Thermo Fisher) or Alexa fluor 647 (Thermo Fisher). After a second round of washing with 0.2% Tween 20 in PBS, the cells were mounted using DAPI-Vector Shield mounting media (Vector) and stored at 4° C. To examine non-dividing status, 2 µM EdU was added (Invitrogen) in the transfected neurons, and detected EdU positive cells by Click-iT EdU kit (Invitrogen).

Immunocytochemistry of primary tissues. Animals were harvested after transcardial perfusion using PBS followed by 4% PFA. Organs were each dissected out and post-fixed with 2% PFA and 15% sucrose in PBS at 4° C. for 16-20 hours, then immersed in 30% sucrose in PBS at 4° C. before sectioning. Mouse brains were fixed in 1% PFA in 0.1 M phosphate buffer (pH 7.4) at 4° C. for 24 hours followed by cryoprotection in 25% sucrose overnight at 4° C. For neonatal brain, brains were embedded in OCT compound (Sakura Tissue-Tek) and sectioned by cryostat (14 µm). Well dried sections were washed 3 times with PBST (1% Tween 20 in PBS) and treated with blocking buffer (2% donkey serum and 0.2% Triton X-100 in PBS, pH 7.4) for 1 hour at room temperature, followed by incubation with primary antibodies diluted in the same buffer overnight at 4° C. The primary antibodies used were Anti-GFP (Ayes) and anti-RFP (Abcam). Sections were washed 3 times in PBST and treated with secondary antibodies conjugated to Alexa 488 or Alexa 546 (Jackson) for 1 hour at room temperature. After wash, the sections were mounted with mounting medium (Perma-Fluor, Thermo scientific). For adult brain, 50 µm coronal brain sections were prepared using a freezing microtome and stored in PBS with 0.01% sodium azide at 4° C. Free-floating sections were incubated at 4° C. for 16-48 hours with goat anti-GFP (Rockland) primary antibodies in PBS/0.5% normal donkey serum/0.1% Triton X-100, followed by the appropriate secondary antibodies conjugated with Alexa 488 (Molecular Probes) at room temperature for 2-3 hours. Sections were counterstained with 10 µM DAPI in PBS for 30 min to visualize cell nuclei Immunostained tissue sections were mounted on slides with polyvinyl alcohol mounting medium containing DABCO and allowed to air-dry overnight. For other tissues, the harvested tissues were embedded in OCT compounds and frozen. Serial or axial frozen sections (thickness 10-20 µm) were prepared using a cryostat, which were then placed on salinized slides and air-dried. The sections were washed with PBS, followed by 1 hour room temperature incubation by blocking buffer containing 3% normal goat serum, 0.3% and Triton X-100 in PBS, then incubated with a primary antibody solution overnight. The primary antibodies used were Anti-GFP (Ayes), Anti-mCherry (Abcam), Anti-dystrophin (Sigma), Anti-Actin, α-Smooth Muscle antibody (Sigma) and Anti-human Serum Albumin antibody (R&D). After wash, the sections were immunostained with secondary antibody solution for 1 hour at room temperature. The secondary antibodies used were Alexa 488, 568 or 647 (Molecular Probes). After sequential washing with 0.2% Tween 20/PBS, 0.05% Tween 20/PBS, and PBS, the sections were mounted with DAPI Fluoromount-G (Southern Biotech). For rat, retinal cryosections were rinsed in PBS and blocked in 0.5% Triton X-100 in 5% BSA in PBS for 1 hour at room temperature. Anti-Mertk antibody (Santa Cruz), anti-Rhodopsin antibody (Santa Cruz) were diluted in 5% BSA in PBS and incubated with sections overnight at 4° C. The sections were then washed three times with PBS, incubated with IgG secondary antibody tagged with Alexa-488 or Alexa-555 (Molecular Probes) in PBS at room temperature for 1 hour, and washed with PBS. Cell nuclei were counterstained with DAPI. Sections were mounted with Fluoromount-G (SouthernBiotech) and coverslipped. Images were captured using a Keyence BZ-9000 microscope.

Image capture and analysis. For immunocytochemical analyses, the cells and tissues were visualized by confocal microscopy using a Zeiss LSM 780 Laser Scanning Confocal or Olympus FV1000 confocal microscope (Olympus). Microscope inverted, and at least 5 pictures were obtained from each coverslip. Pictures were analyzed with ZEN 2 (blue edition) and NIH ImageJ (FIJI) software. For the mouse primary neurons and human pan-neurons analyses, the total number of positive cells for each marker was directly counted with the multi-point tool of NIH ImageJ software. The percentage of GFP+ cells was calculated considering the amount of transfected cells. The intracellular distribution of GFP was observed in around 100 independent events for each condition, where the focused cell was observed at different stacks to determine the presence or absence of GFP at the nucleus space.

Nuclear/cytoplasm ratio. To measure intracellular localization of dCas9, a previous report was followed (Wu, J., Corbett, A. H. & Berland, K. M. The intracellular mobility of nuclear import receptors and NLS cargoes. *Biophys. J.* 96, 3840-3849 (2009)). In brief, the dCas9 transfected HEK293 cells were fixed with 4% PFA and stained with anti-FLAG (Sigma) and DAPI (Vector). The intensity of fluorescence was measured using the PlotProfile tool of ImageJ software. Values were obtained independently in cytoplasmic and nuclear compartments in single transfected cells. Relative fluorescence values of nuclear intensity were divided by the values found in cytoplasm to obtain the nuclear/cytoplasm ratio.

Gene transfer into mouse embryos by in utero electroporation. The experimental procedures for electroporation have been described previously (Takahashi, M., Nomura, T., & Osumi N Transferring genes into cultured mammalian embryos by electroporation. *Dev Growth Differ* 50, 485-497 (2008)). E15.5 pregnant ICR was anesthetized by 500 jai IP injection of 10% Nembutal (Dainippon sumitomo kagaku). Embryos were injected into the hemisphere with 1 μl of DNA mixture, containing the pCAG-1BPNLS-Cas9-1BPNLS mouse Tubb3 gene target pCAGmCherry-gRNA (0.5 μg/μl) and either minicircle donor (Tubb3-MC) or HDR donor (Tubb3-HDR) vectors (0.8 μg/μl). For visually confirming the injection, 0.005% fast green solution (Wako) was mixed with the DNA. Embryos were tweezed by paddles of the tweezer electrodes (CUY21 electroporator, NEPA GENE). For tamoxifen (TAM) inducible Cre-dependent Cas9 expression system, embryos were injected into the hemisphere with 1 μl of DNA mixture, containing the pCAG-flox-1BPNLS-Cas9-1BPNLS (0.5 μg/μl), pCAG-ERT2CreERT2 (0.5 μg/μl), pCAG-mcherry-U6-gRNA (0.5 μg/μl), and either minicircle donor (Tubb3-MC) or HDR donor (Tubb3-HDR) vectors (0.8 μg/μl). 50 jai of 10 mg/ml tamoxifen (Sigma) dissolved in corn oil were injected to P10 and P11 electroporated pups for induction of the Cas9 expression.

In vivo muscle electroporation. The DNA mixture for −Cas9 (25 pig of empty vector, 25 μg of gRNA expression vector and 10 μg of Ai14-luc-MC or Ai14-GFP-MC) and for +Cas9 (25 pig of pCAG-1BPNLS-Cas9-1BPNLS, 25 pig of gRNA expression vector and 10 μg of Ai14-luc-MC or Ai14-GFP-MC) were prepared in 50 jai TE. Ai14 mice were anesthetized with intraperitoneal injection of ketamine (100 mg/kg) and xylazine (16 mg/kg). For quadriceps muscle electroporation, a small portion of the quadriceps muscle was surgically exposed in the hind limb. Plasmid DNA mixture was injected into the muscle using a 29-gauge insulin syringe. One minute following plasmid DNA injection, a pair of electrodes was inserted into the muscle to a depth of 5 mm to encompass the DNA injection site and muscle was electroporated using an Electro Square Porator T820 (BTX Harvard Apparatus). Electrical stimulation was delivered twenty pulses at 100 V for 20 msec. After electroporation, skin was closed and mice were recovered on a 37° C. warm pad. For panniculus *carnosus* muscle electroporation, the hair of back skin was depilated with depilatory cream. The above mixture of DNA solutions were conjugated and subcutaneously injected to right and left side, respectively. The injected areas of skin and subcutaneous tissue was vertically sandwiched by plate-and-fork type electrodes, consist of a pair of stainless-steel tweezers, one with a rectangular plate, 10 mm long and 5 mm wide, and the other with a fork consisting of three straight needles at 2.5 mm intervals, which are 10 mm long and 0.5 mm in diameter. The interface of skin and the rectangular electrode were covered with electroconductive gel (SpectraGel 360, Parker Labs). Twenty18V/50 ms/1 Hz-square pulses followed by another 20 pulses of the opposite polarity were delivered using Electro Square Porator T820. Two weeks after the electroporation, mice were euthanized, and tissues were obtained.

Tissue pressure-mediated transfection. The DNA mixture for −Cas9 (100 pig of empty vector, 100 μg of gRNA expression vector, and 50 μg of Ai14-luc-MC) and for +Cas9 (100 pig of pCAG-1BPNLS-Cas9-1BPNLS, 100 μg of gRNA expression vector, and 50 μg of Ai14-luc-MC) were prepared in 200 ul saline. A midline laparotomy was performed and the right kidney of Ai14 mouse was exteriorized. After exposure of kidney, mice were intravenously injected with plasmid DNA mixture, immediately followed by pressing the right kidney gripped between thumb and index finger 20 times for a period of 1 sec each as described (Mukai, H., Kawakami, S. & Hashida, M. Renal press-mediated transfection method for plasmid DNA and siRNA to the kidney. *Biochemical and Biophysical Research Communications* 372, 383-387 (2008)).

In vivo electroporation for kidney. The DNA mixture for −Cas9 (100 ug of empty vector, 100 ug of gRNA expression vector and 50 ug of Ai14-GFP-MC) and for +Cas9 (100 ug of pCAG-1BPNLS-Cas9-1BPNLS, 100 ug of gRNA expression vector and 50 ug of Ai14-GFP-MC) were prepared in 200 ul saline. A midline laparotomy was performed. The right kidney of Ai14 mouse was exteriorized and subsequently decapsulated, leaving the adrenal gland intact. Then, the exposed kidney was picked with electrode needles after injection of plasmid DNA mixture from tail vein and subsequently received electroporation 100 V, 50 ms pulse, 6 times using an Electro Square Porator T820.

Luciferase detection. Mice were examined at 2 weeks after DNA transfection or electroporation by BLI performed using an IVIS Kinetic 2200 (Caliper Life sciences). Mice were IP injected with 150 mg/kg D-Luciferin (BIOSYNTH), anesthetized with isoflurane, and dorsal images were then captured 10 minutes post luciferin injection.

AVV infection in mouse primary neuron. Primary cultures of neurons were used after three days in culture, the AAV solution (−Cas9, AAV-mTubb3 ($1.5\times10^{10}$ GC); +Cas9, AAV-Cas9 ($1.5\times10^{10}$ GC) and AAV-mTubb3 ($1.5\times10^{10}$ GC)) was added and cultures were kept at standard conditions for 5 days, following immunocytochemistry or DNA extraction.

Stereotax AAV injection in adult brain. C57BL/6 mice received AAV injections at P75. A 1:1 mixture of AAV-Cas9 ($1.5\times10^{13}$ GC/ml) and AAV-mTubb3 ($2.3\times10^{13}$ GC/ml) was used. As a control, 1:1 mixture of AAV-mTubb3 and HBSS buffer was used. Mice were anesthetized with 100 mg/kg of ketamine and 10 mg/kg of xylazine cocktail via intraperitoneal injections and mounted in a stereotax (David Kopf Instruments Model 940 series) for surgery and stereotaxic injections. Virus was injected into the center of V1, using the following coordinates: 3.4 mm rostral, 2.6 mm lateral relative to bregma and 0.5-0.7 mm ventral from the pia. 200 nl of AAVs were injected using air pressure by picospritzer (General Valve Corp). To prevent virus backflow, the pipette was left in the brain for 5-10 minutes after completion of injection. Mice were housed for two weeks to allow for gene knock-in.

Intramuscular AAV injection. Ai14 mice were anesthetized with intraperitoneal injection of ketamine (100 mg/kg) and xylazine (16 mg/kg). A small portion of the quadriceps muscle was surgically exposed in the hind limb. The AAV mixture (−Cas9, AAV-Ai14-GFP ($1.5 \times 10^{10}$ GC); +Cas9, AAV-Cas9 ($1.5 \times 10^{10}$ GC) and AAV-Ai14-GFP ($1.5 \times 10^{10}$ GC)) was injected into the quadriceps muscle using a 29 Gauge insulin syringe. After electroporation, skin was closed and mice were recovered on a 37° C. warm pad.

Intravenous (IV) AAV injection. The newborn (P1) of Ai14 mice was used for IV AAV injection as following previous report (Lampe, S. E. G., Kaspar, B. K. & Foust, K. D. Intravenous Injections in Neonatal Mice. JoVE (Journal of Visualized Experiments) e52037-e52037 (2014). doi: 10.3791/52037). The AAV mixture (−Cas9, AAV-Ai14-GFP ($5 \times 10^{10}$ GC); +Cas9, AAV-Cas9 ($5 \times 10^{10}$ GC) and AAV-Ai14-GFP ($5 \times 10^{10}$ GC)) were injected via temporal vein at P1 mouse.

Tail vein AAV injection. The AAV mixture (−Cas9, AAV-Ai14-luc ($5 \times 10^{10}$ GC); +Cas9, AAV-Cas9 ($5 \times 10^{10}$ GC) and AAV-Ai14-luc ($5 \times 10^{10}$ GC)) were injected via tail vein for luciferase knock-in. The AAV mixture (−Cas9, AAV-Ai14-GFP ($5 \times 10^{10}$ GC); +Cas9, AAV-Cas9 ($5 \times 10^{10}$ GC) and AAV-Ai14-GFP ($5 \times 10^{10}$ GC)) were injected via tail vein for GFP knock-in.

Targeted deep sequencing. The top 12 predicted off-target sites were searched using The CRISPR Design Tool (Hsu, P. D. et al. DNA targeting specificity of RNA-guided Cas9 nucleases. *Nature Biotechnology* 31, 827-832 (2013)). The on-target and potential off-target regions were amplified using PrimeSTAR GXL DNA polymerase from the liver DNA via IV injection and used for library construction. Equal amounts of the genomic DNA was used to amplify genomic regions flanking the on-target and top 12 predicted off-target nuclease binding sites for library construction. Next, PCR amplicons were purified using Ampure beads (Beckman Coulter), then subject to second round PCR to attach Illumina P5 adapters and sample-specific barcodes. The purified PCR products were pooled at equal ratio for single-end sequencing using Illumina MiSeq. The raw reads were mapped to mouse reference genome mm9 using BWA (Li, H. & Durbin, R. Fast and accurate short read alignment with Burrows-Wheeler transform. *Bioinformatics* 25, 1754-1760 (2009)). High quality reads (score >30) were analyzed for insertion and deletion (indel) events from 5 nucleotides upstream to 5 nucleotides downstream of the nuclease binding site (a total of 32 bp) using Freebayes (Garrison, E. & Marth, G. Haplotype-based variant detection from short-read sequencing. (2012)).

Subretinal injection for rats. Congenic RCS rats at 21 days old were used in the study and divided into two groups. Group A (n=3) received a subretinal injection of 2 ul of AAV mixture (AAV-Cas9 ($1.5 \times 10^{10}$ GC) and AAV-rMertk ($1.5 \times 10^{10}$ GC)) in the eyes. Group B (n=3) was given a sham injection as a negative control with injection of the vesicles. Wild type rats (n=3) without an injection served as a normal control. Experimental rats were anesthetized with an intraperitoneal injection of a mixture of ketamine and xylazine. Pupils were dilated with 1% topical tropicamide. Subretinal injection was performed under direct visualization using a dissecting microscope with a pump microinjection apparatus (Picospritzer III; Parker Hannifin Corporation) and a glass micropipette (internal diameter 50-75 m). Two ul of AAV mixture was injected into the subretinal space through a small scleral incision. A successful injection was judged by creation of a small subretinal fluid bleb. Fundus examination was performed immediately following injection, and rats showing any sign of retinal damage such as bleeding were discarded and excluded from the final animal counts.

ERG Recording. To monitor the efficacy of gene knock-in in vision rescue, ERG studies were performed at 4 weeks after treatment before the animals were sacrificed for histology. The dark-adapted ERG response was recorded as described previously (Sauvé, Y., Lu, B. & Lund, R. D. The relationship between full field electroretinogram and perimetry-like visual thresholds in RCS rats during photoreceptor degeneration and rescue by cell transplants. *Vision Research* 44, 9-18 (2004)). In brief, rats were dark-adapted for 14 hour prior to the commencement of each ERG recording session. They were deeply anesthetized as described for the surgical procedure above. Eyes were treated with 1% topical tropicamide to facilitate pupillary dilation. Each rat was tested in a fixed state and maneuvered into position for examination within a Ganzfeld bowl (Diagnosys LLC). One active lens electrode was placed on each cornea, with a subcutaneously placed ground needle electrode positioned in the tail and the reference electrodes placed subcutaneously in the head region approximately between the two eyes. Light stimulations were delivered with a xenon lamp at 0.01 and 0.3 cds/m$^2$ in a Ganzfeld bowl. For the flicker ERG measurement, rats were adapted at a background light of 10 cds/m$^2$, and light stimulation was set at 30 cds/m$^2$. The recordings were processed using software supplied by Diagnosys.

Histological Analysis for rat. Following ERG recordings, rats were sacrificed, and retinal cross-sections were prepared for histological evaluation of ONL preservation. Rats were euthanized with $CO_2$, and eyes were dissected out and fixed in 4% PFA. Cornea, lens, and vitreous were removed from each eye without disturbing the retina. The remaining retina containing eyecup was infiltrated with 30% sucrose and embedded in OCT compound. Horizontal frozen sections were cut on a cryostat. Retinal cross-sections were prepared for histological evaluation by staining with hematoxylin and eosin (H&E).

DNA extraction and genotyping from rat eye. Genomic DNA was isolated from cryo-sections of the above mentioned embedded eyecup samples. Twenty frozen sections were cut and the material was transferred to Eppendorf tubes and subject to DNA extraction using an established protocol (Talaulikar, D., Shadbolt, B., McNiven, M. & Dahlstrom, J. E. DNA amplification from formalin-fixed decalcified paraffin-embedded bone marrow trephine specimens: does the duration of storage matter? *Pathology* 40, 702-706 (2008)). The quality (OD260/OD280) and quantity (OD260) of DNA was determined using the NANODROP 2000 (Thermo Scientific) equipment. DNA was used for PCR and direct DNA sequencing for genotype determination.

Statistical analysis. Results are shown as mean±s.d. Comparisons were performed with Student's t-test.

Example 2: Homology Independent Strategy for Efficient Targeted Transgene Integration One of the major therapeutic approaches to combat detrimental cellular phenotypes caused by loss-of-function mutations relies on intracellular delivery of a wild-type gene copy. In this regard viral-mediated gene-replacement therapy, a rapid evolving field, has been providing some solutions, however, is limited by incomplete control over transgene copy numbers and expression levels, as well as the risk of adverse phenotypic effects such as insertional mutagenesis and activation of (proto)-oncogenes. Site-specific transgene integration exploiting the homology-directed repair (HDR) pathway offers the most pertinent solution for these problems. However, the utility of HDR is currently limited by its low efficiency in most primary cell types. Moreover, HDR only occurs during the S/G2 phases of the cell cycle making it inaccessible to non-dividing cells, which are prevalent in post-natal animal tissues. The other major DNA double-strand break (DSB) repair pathway, non-homologous end joining (NHEJ), is active throughout the cell cycle in a variety of adult cell types, including both proliferating and post-mitotic cells. In addition, in most cases, NHEJ activity has been found to be much higher than that of HDR in higher organisms and most recently harnessed for efficient targeted gene disruption in vivo to improve muscle function for a mouse model of muscular dystrophy. These attributes suggest that, if possible, hijacking the NHEJ pathway for targeted knock-in might constitute a fruitful approach towards overcoming some of the hurdles related to HDR. Although methods relying on homology independent NHEJ-based DNA ligation have been proposed to bypass HDR for precise transgene insertion, their efficacy in post-mitotic cells remains elusive. Moreover, to date, it is unknown whether such strategies could be harnessed for in vivo applications in adult animals. To this end, a robust homology independent strategy was developed for efficient targeted transgene integration in both dividing and post-mitotic cells in vivo.

Figure 1B:
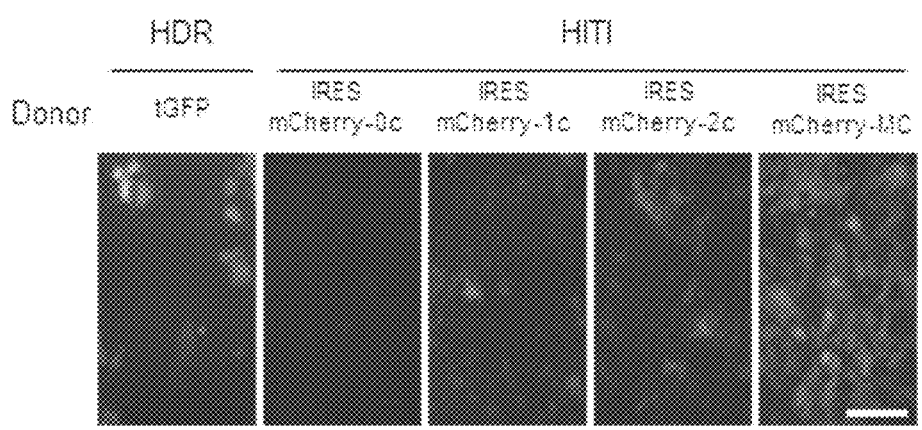
Figure 1C:
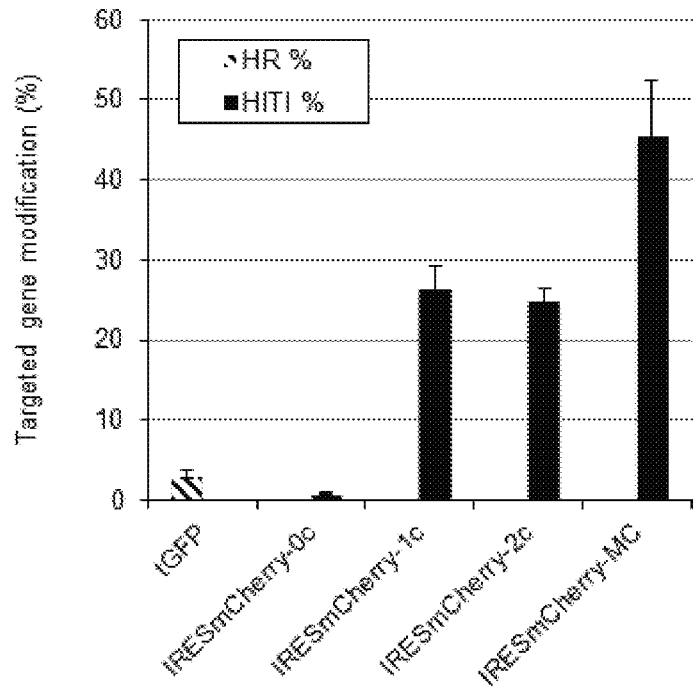
Figure 1D:
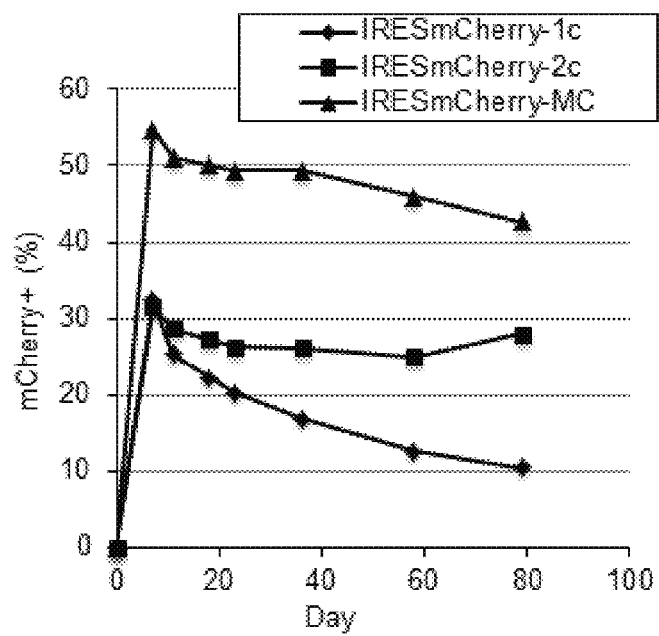
Figure 1E:
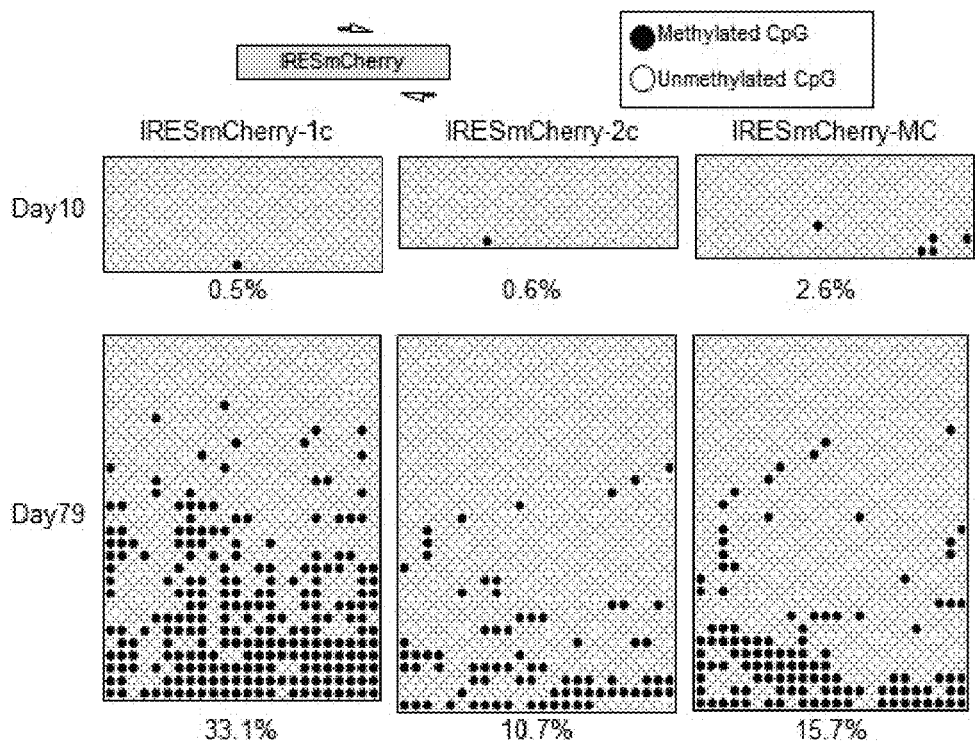
Figure 5A:
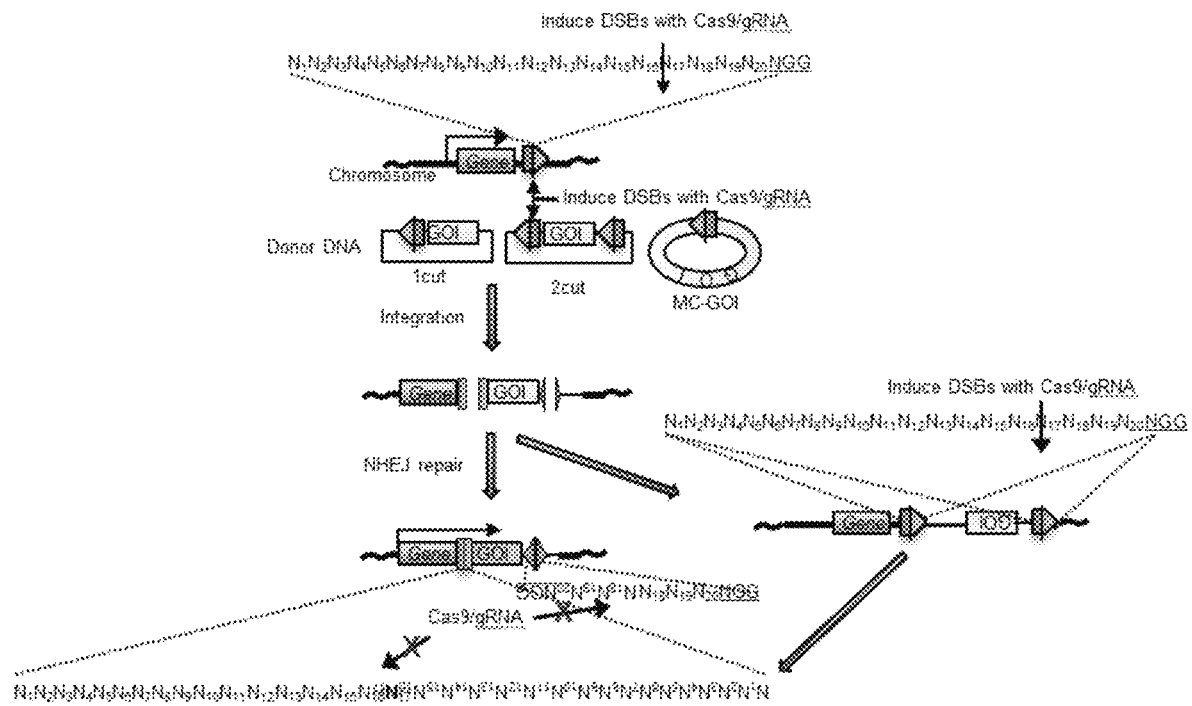
Figure 5B:
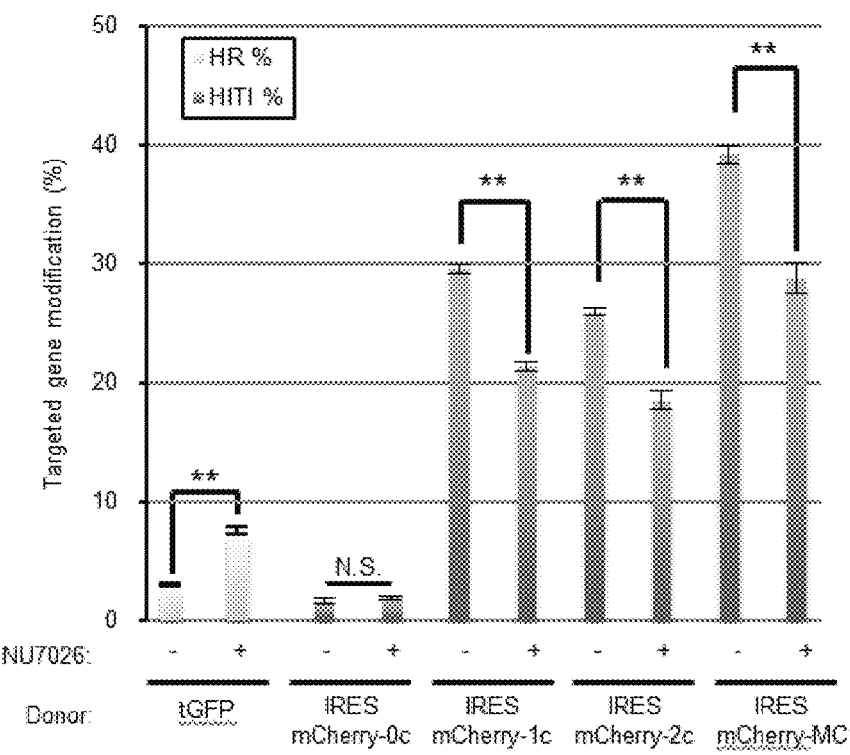
Figure 5C:
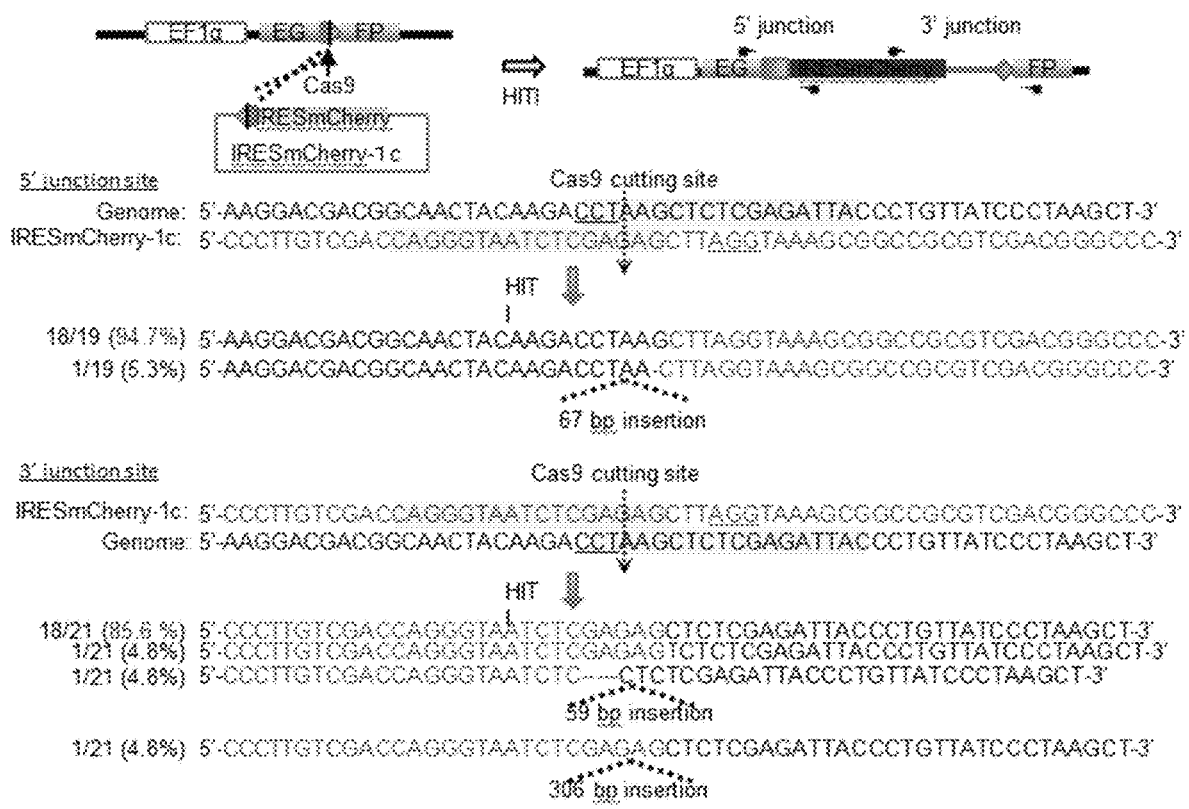
Figure 5D:
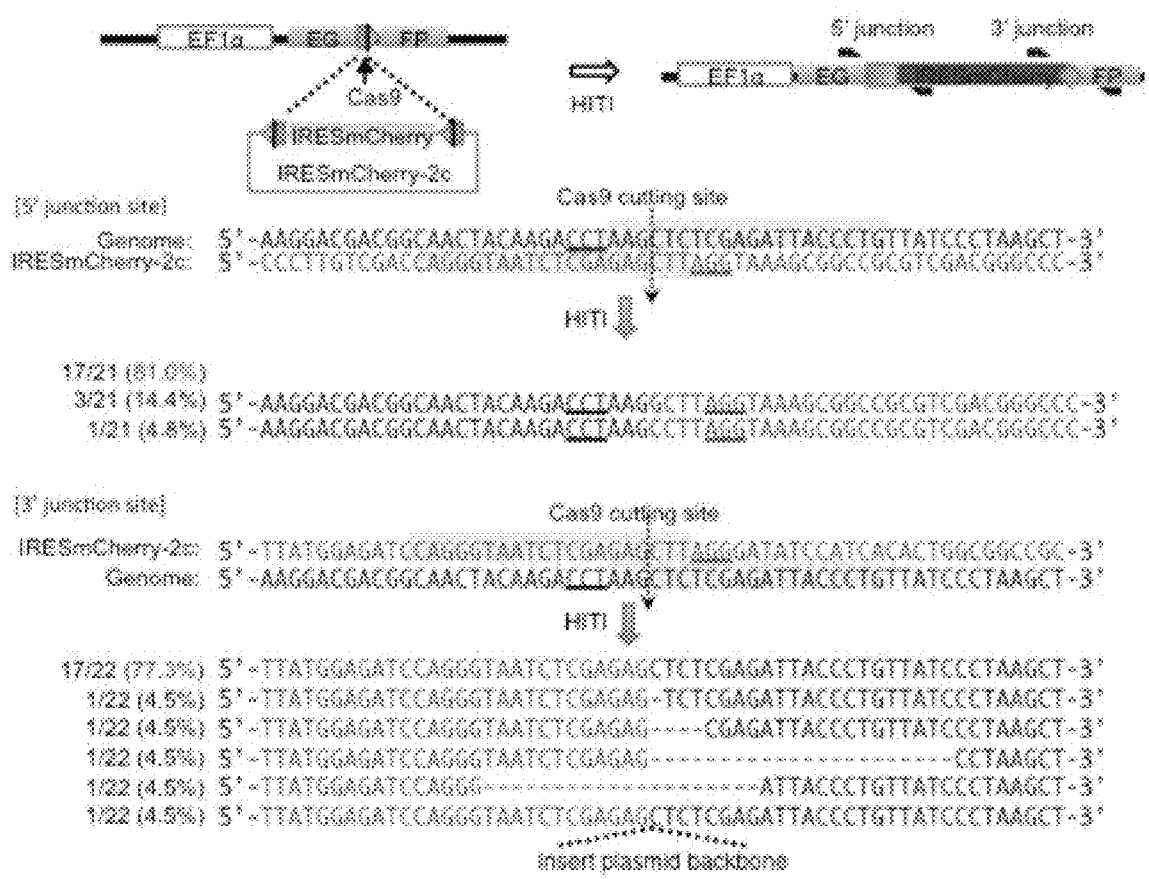
Figure 5E:
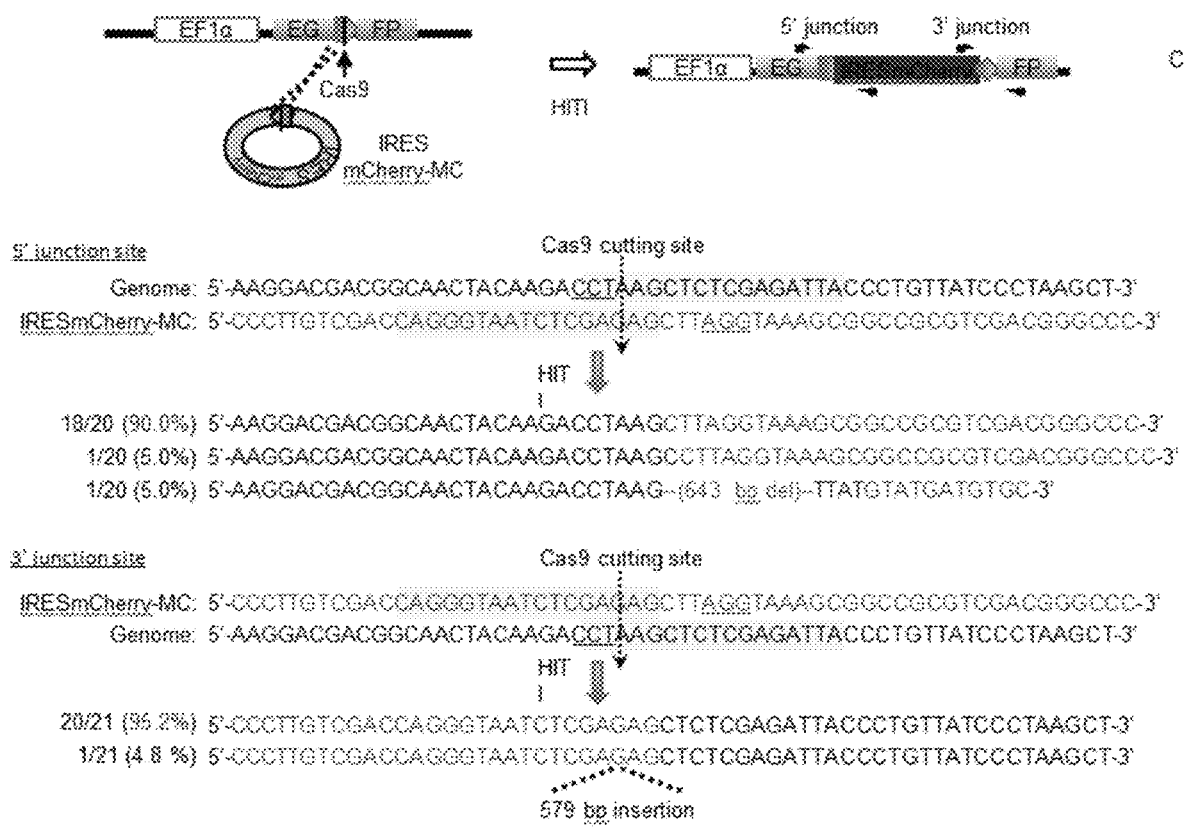

Existing methods were improved for more robust NHEJ-based targeted knock-in. To measure the knock-in efficiencies of both HDR- and NHEJ-based gene-targeting activities in dividing cells, a HEK293 line was generated stably expressing a mutated GFP gene driven by the EF1a promoter (designated as GFP-correction HEK293 line). Next, Cas9/gRNA and different donor plasmids were co-transfected. The efficiencies of targeted gene replacement via HDR and homology-independent targeted integration (HITI) were determined by GFP and mCherry signals respectively (FIG. 1A). Using this system, higher efficiency integration of 1-cut donor (IRESmCherry-1c) via NHEJ versus HDR donor (tGFP) in HEK293 cells was confirmed (FIG. 1B, FIG. 1C). However, it was observed that the percentage of mCherry+ cells decreased over time in culture, probably due to increased DNA methylation in the mCherry gene (FIG. 1D, FIG. 1E). It was reasoned that the inclusion of the bacterial backbone might have triggered gene silencing. To overcome this, a 2-cut plasmid (IRESmCherry-2c) harboring gRNA recognition sequences at both sides of the IRESmCherry gene, and a minicircle DNA devoid of the bacterial backbone (IRESmCherry-MC) were designed and tested. Both plasmids could be inserted at the targeted genome locus with high efficiency and minimal silencing, as evidenced by less pronounced DNA methylation and a significantly higher percentage of mCherry+ cells after 80 days in culture (FIGS. 1A-1E). These results demonstrated an enhanced stability of the transgene introduced by 2-cut and minicircle donor plasmids than previously reported with 1-cut donor. Of note is that the efficiency with a minicircle donor is higher than that of both 1-cut and 2-cut donors. Treatment with the NHEJ inhibitor NU7026 significantly decreased the efficiency of HITI, suggesting that the HITI is mediated by the NHEJ repair machinery (FIG. 5B). Contingent on the necessity of processing DNA ends prior to joining, the classical NHEJ-mediated DSB repair yields either error-prone or error-free end joining. Sanger sequencing results showed that, upon integration, the majority of junction sites had no insertions or deletions (indels), suggesting error-free repair is dominant in this context (FIGS. 5C-E). To examine the directionality of targeted insertion (FIG. 5A), mCherry-cells were sorted and single cell clones were generated. Out of 48 clones examined only one (2.1%) showed the IRESmCherry cassette integrated in the opposite direction, indicating that HITI mostly generated unidirectional knock-ins (FIG. 5F). Taken together, the results demonstrate that the HITI method with 2-cut or minicircle donor plasmids provide a more stable and efficient transgene integration via NHEJ-based DSB repair.

Example 3: Gene Delivery in Non-Dividing Cells

Figure 6A:
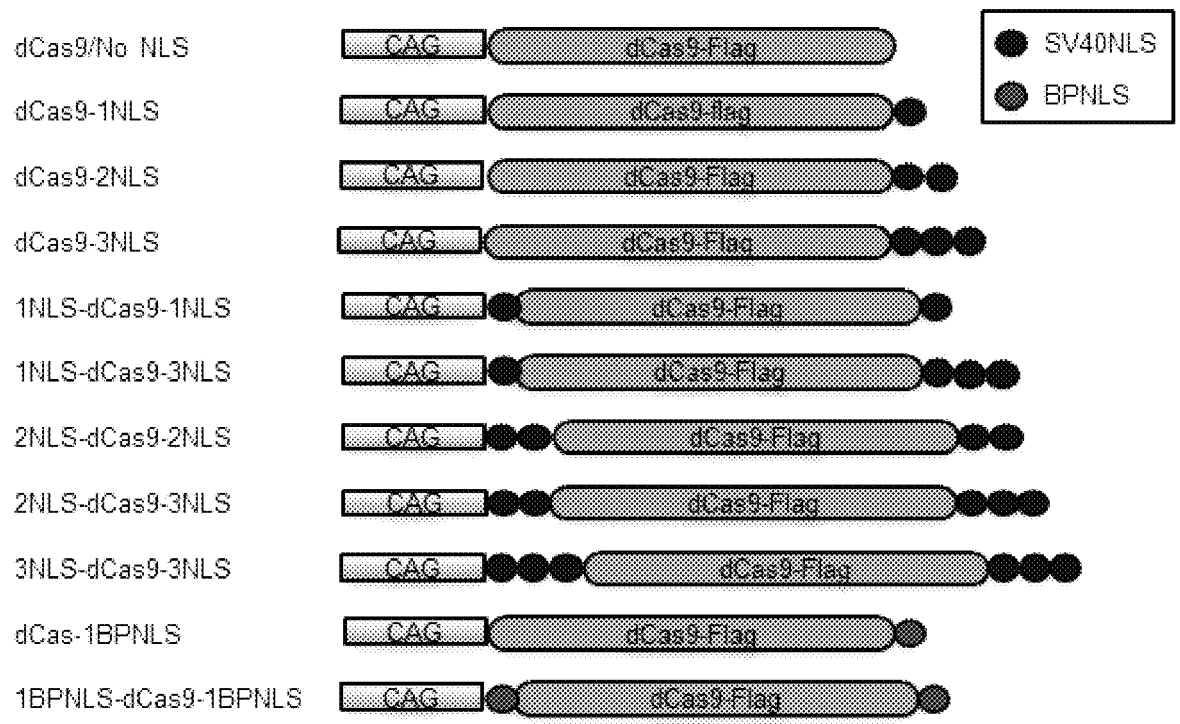
FIGS. 6A-6E show optimization of nuclear transport of Cas9 for HITI.
Figure 6B:
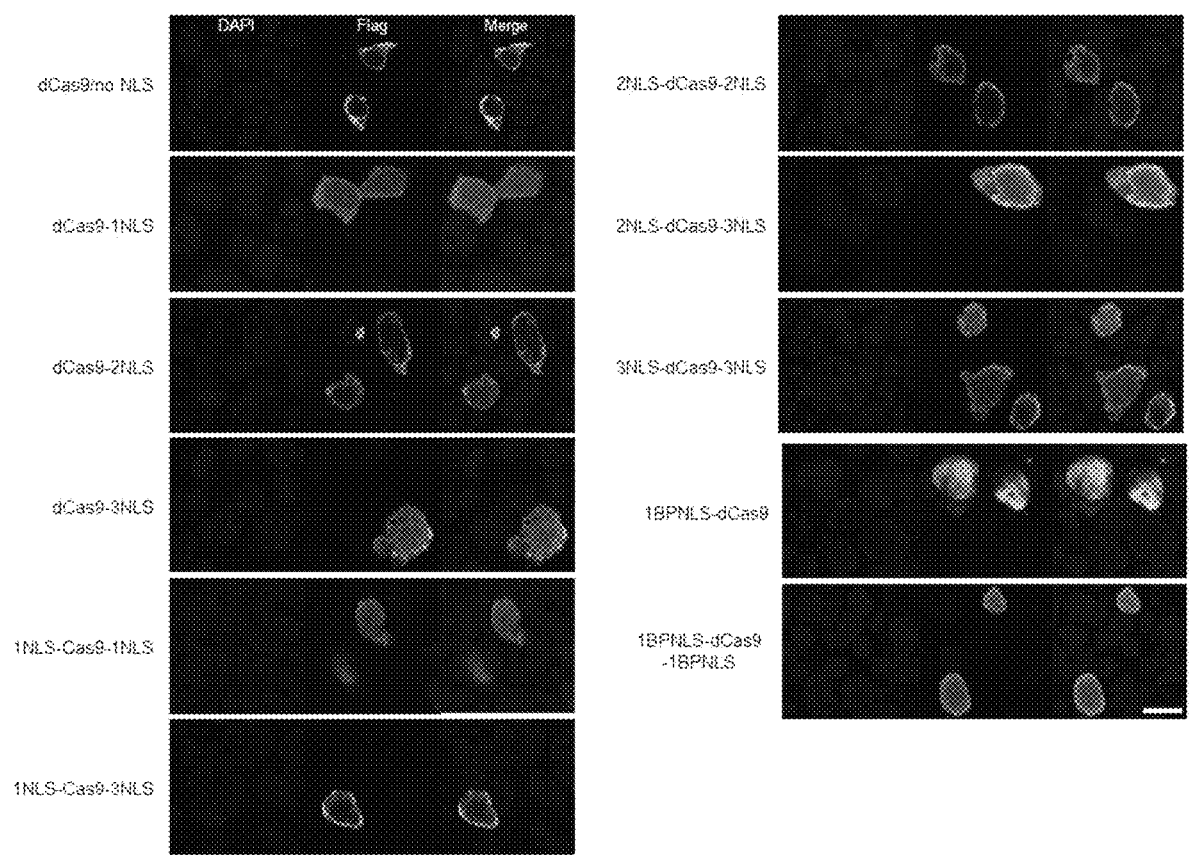
Figure 6C:
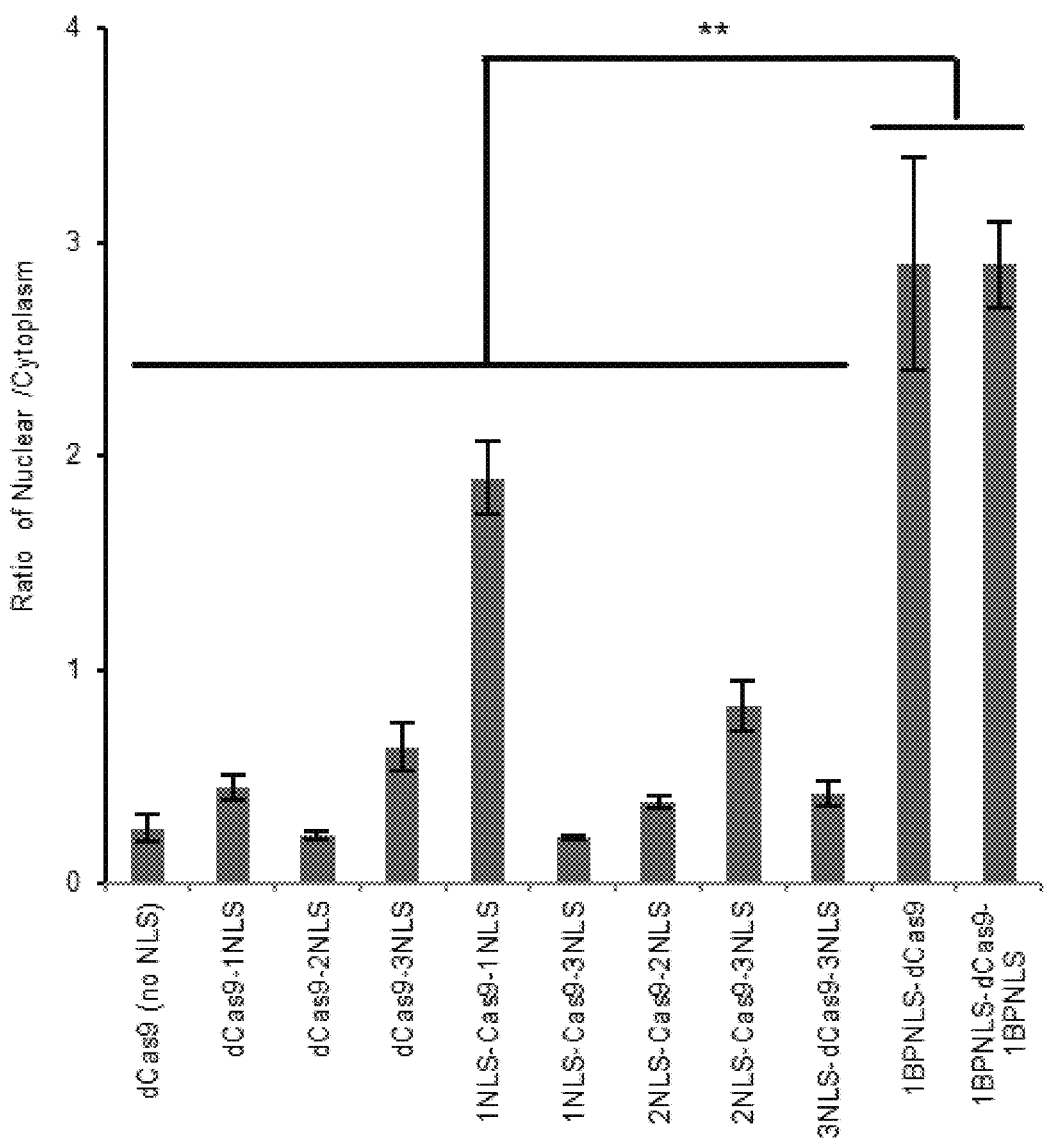
Figure 6D:
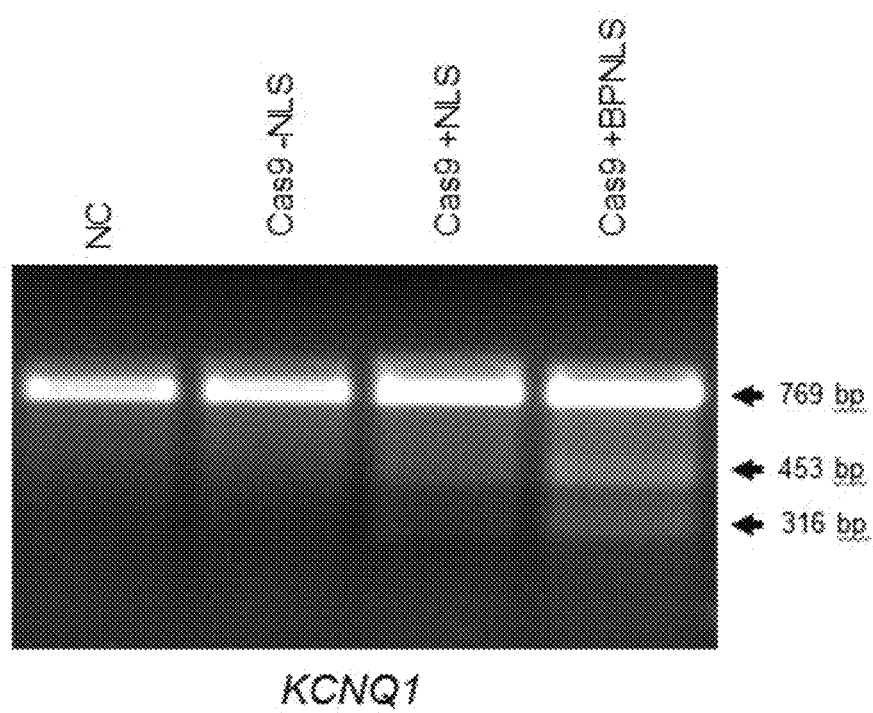
Figure 6E:
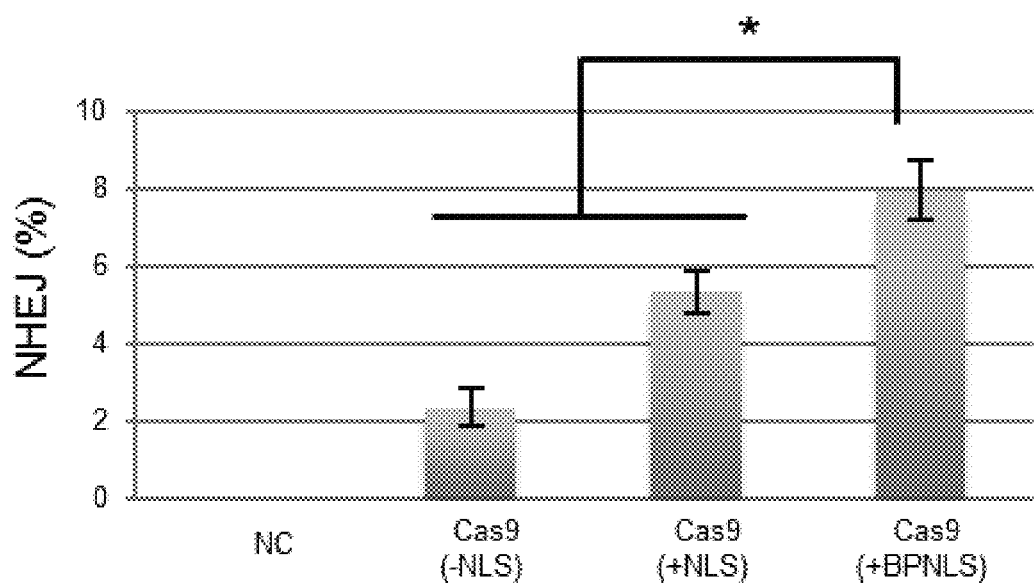

In addition to knock-in efficiency, it was hypothesized that intra-nucleus delivery of Cas9 would enhance CRISPR-Cas9 gene targeting effectiveness, particularly for non-dividing cells. To this end, the nuclear transport of Cas9 was improved by design optimization of the nuclear localization signal (NLS). A series of NLS attached to catalytically inactive Cas9 (dCas9) were designed and constructed and the nuclear/cytoplasm ratio was evaluated upon delivery to HEK293 cells. The results revealed that an artificial long NLS (bipartite SV40 NLS or BPNLS) was more potent in enriching dCas9 in the nucleus than conventional Cas9 sandwiched by two SV40NLS (FIGS. 6A-C). Consequently, enhanced nuclear localization efficiency conferred by BPNLS resulted in more efficient genome editing in human embryonic stem cells (ESCs) with catalytically active Cas9 (FIGS. 6D and 6E).

Figure 1F:
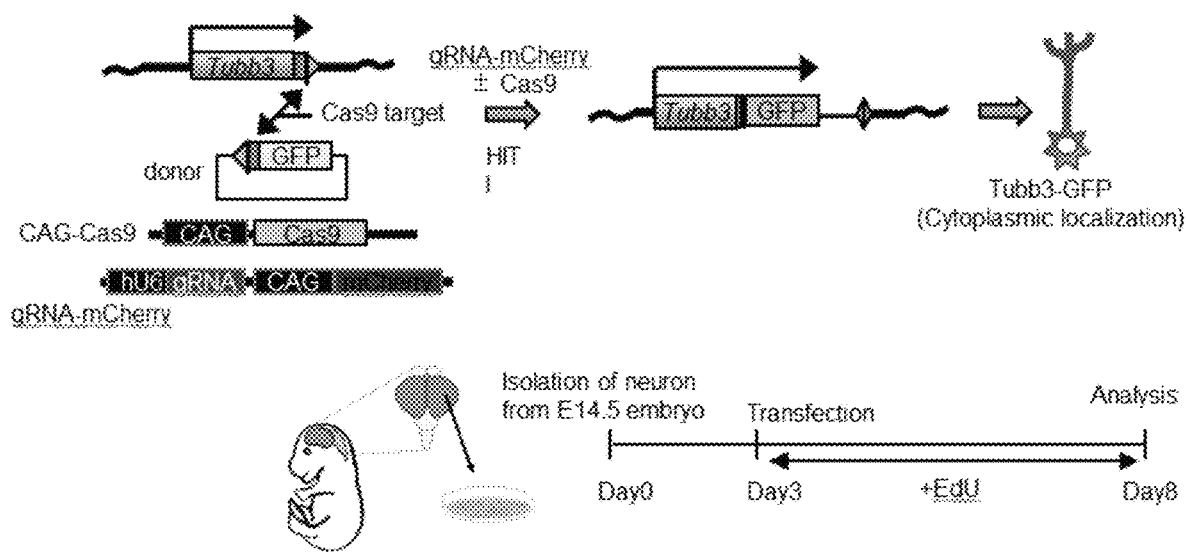
Figure 1G:
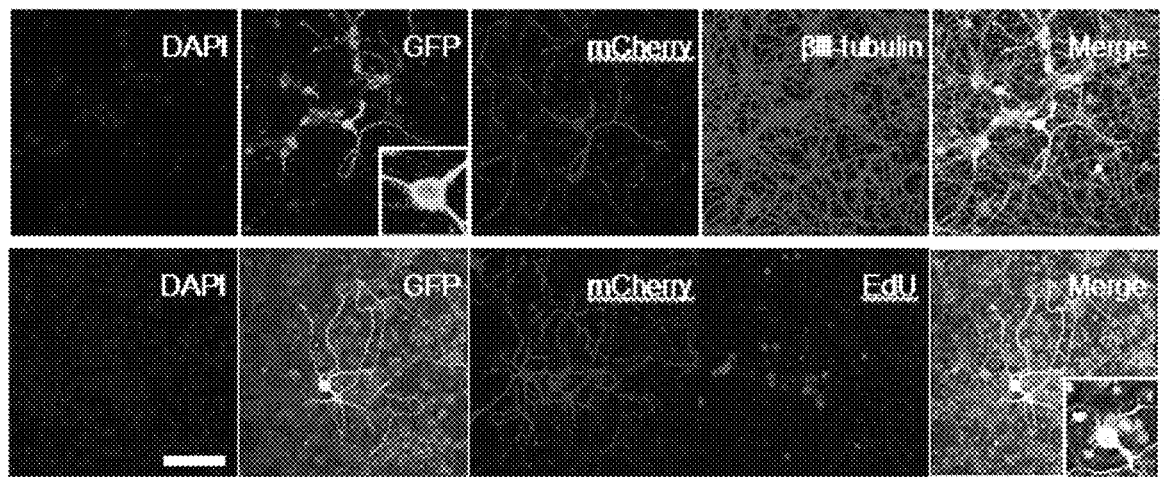
Figure 1H:
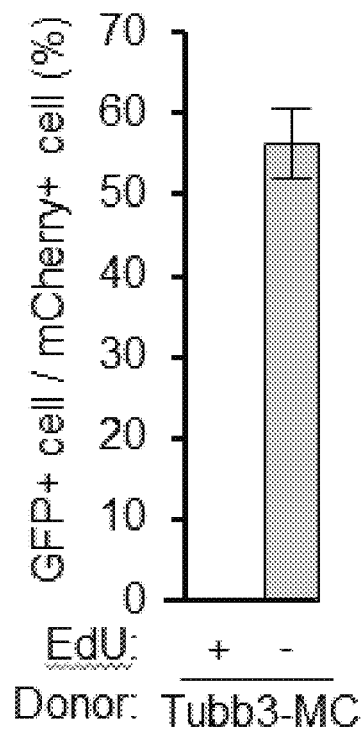
Figure 1I:
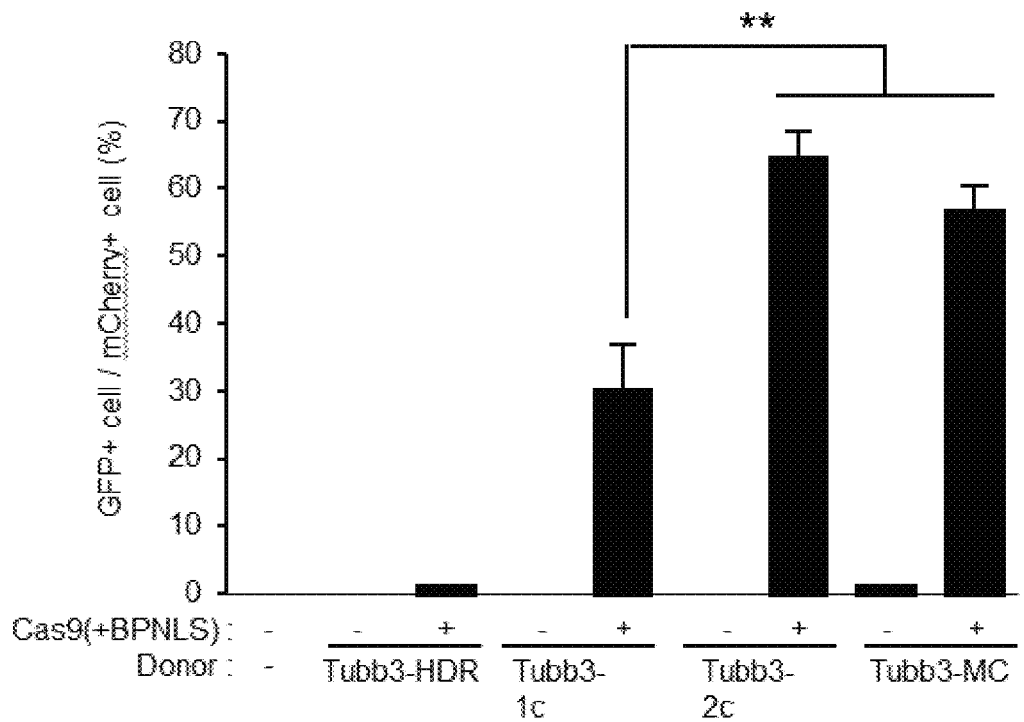
Figure 1J:
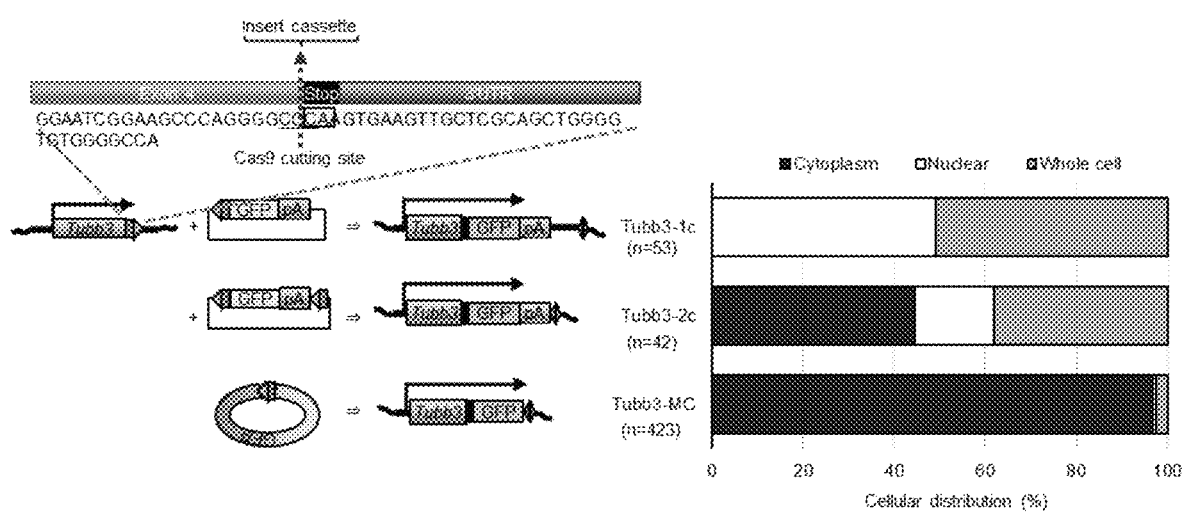
Figure 1K:
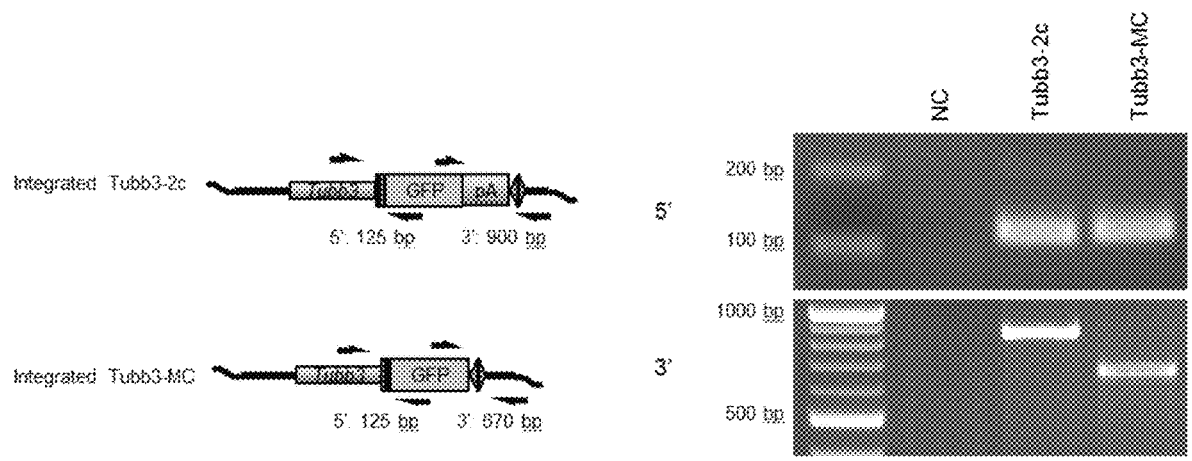
Figure 1L:
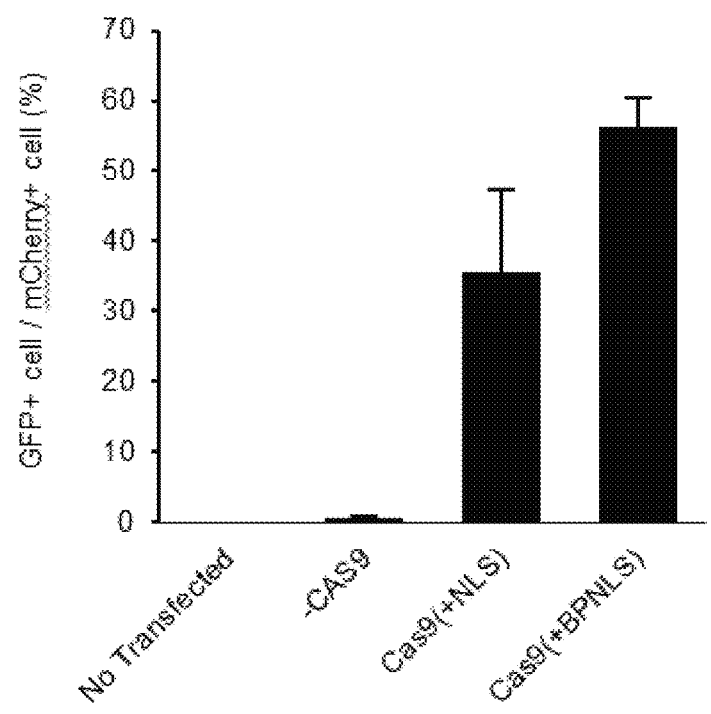
Figure 7:
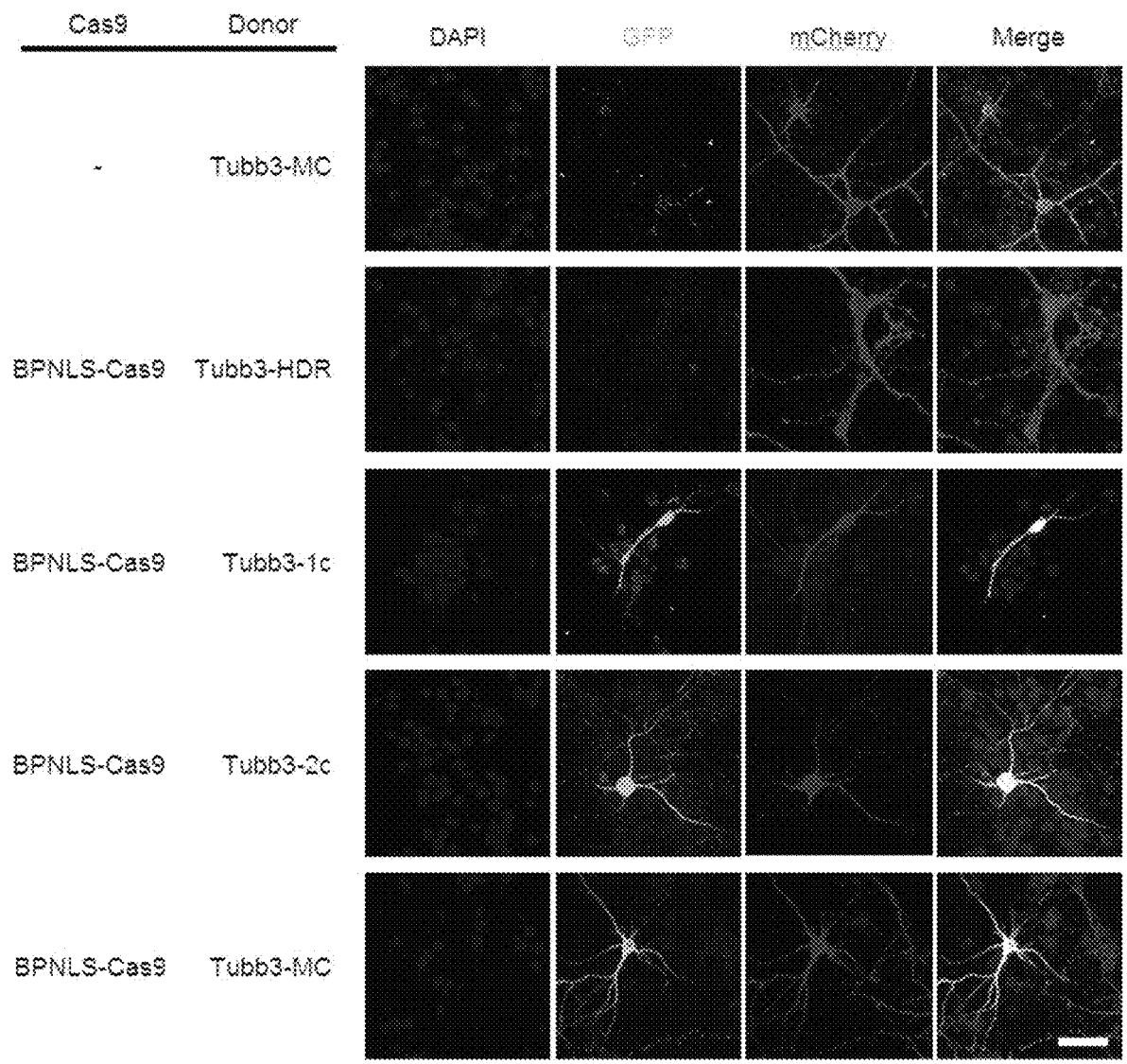
FIG. 7 shows intracellular localization of Tubb3-GFP with different donor DNA. Representative fluorescence images of the primary neurons transfected with BPNLS-Cas9, gRNA, and different donor DNA (Tubb3-HDR, Tubb3-1c, Tubb3-2c or Tubb3-MC). Different intracellular localization patterns of Tubb3-GFP were observed for different donors. Scale bar, 100 μm.
Figure 8A:
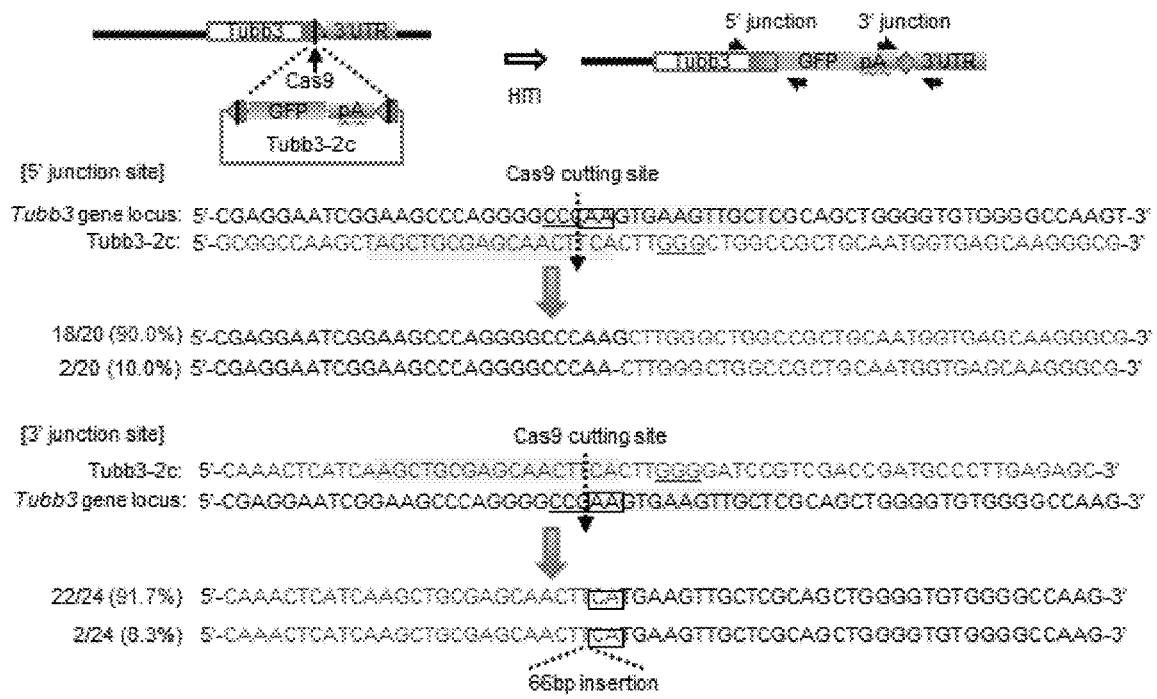
FIGS. 8A-8B show DNA sequencing analysis of GFP knock-in in mouse primary neurons. Sequences of the 5' and 3' junction sites after GFP knock-in by HITI in mouse primary neurons with Tubb3-2c (FIG. 8A) and Tubb3-MC (FIG. 8B).
Figure 8B:
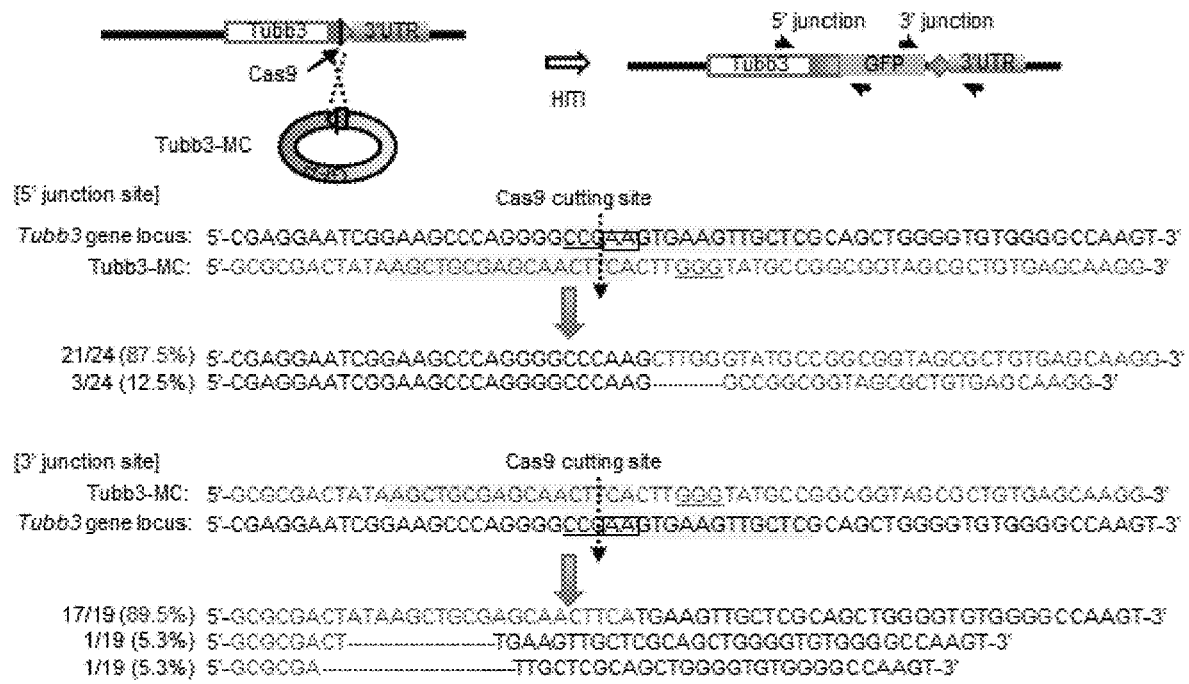
Figure 9A:
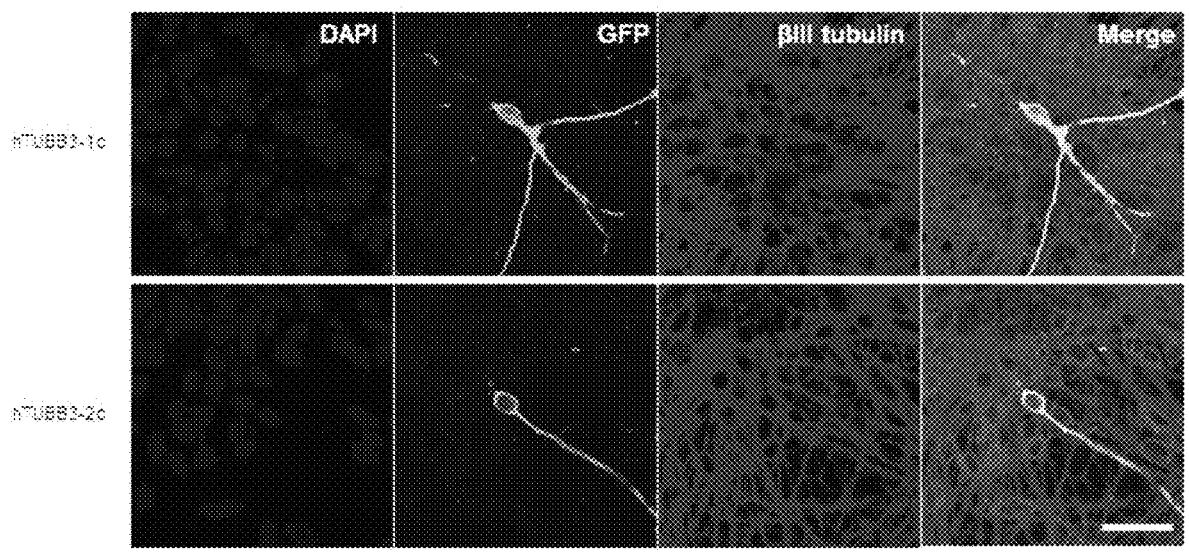
FIGS. 9A-9D show HITI in hESC-derived pan neurons in vitro.
Figure 9B:
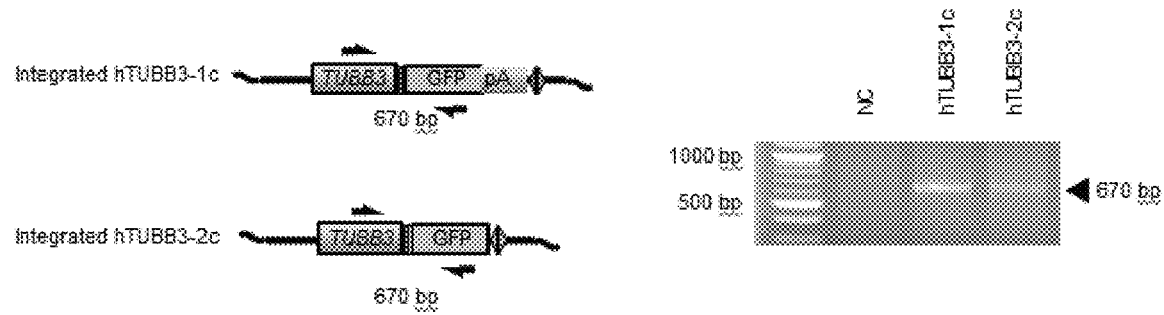
Figure 9C:
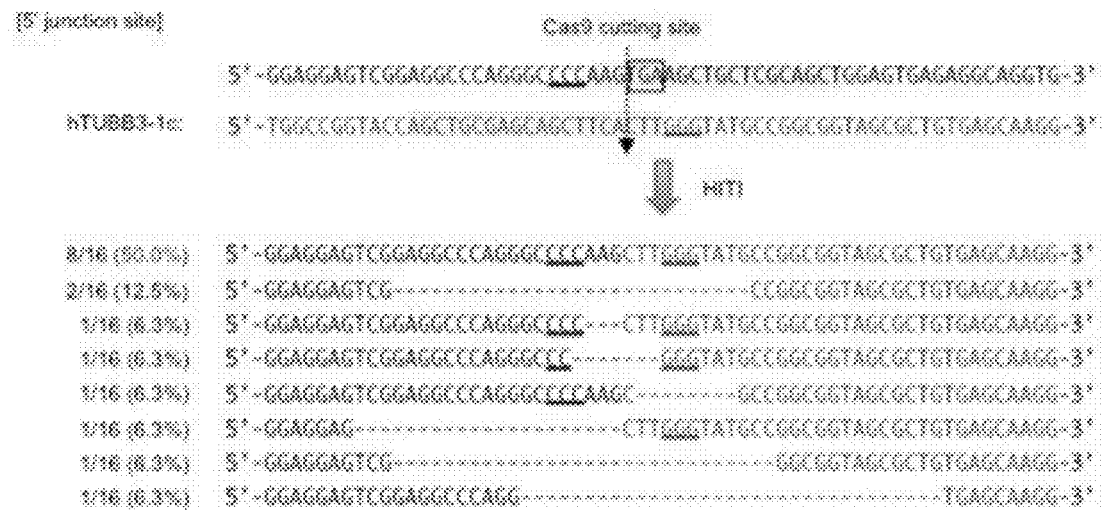
Figure 9D:
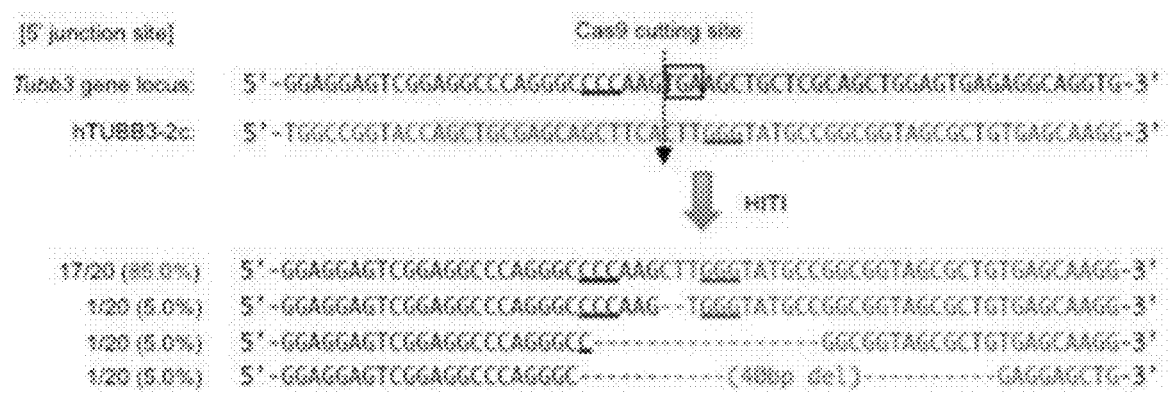

The HITI method was tested in non-dividing cells in vitro. To this end, E14.5 mouse primary neurons were isolated and cultured in vitro for 3 days before transfection with Cas9/gRNA constructs along with different donor plasmids. Donor plasmids were designed for targeted insertion of GFP downstream of the Tubb3 gene, resulting in the expression of Tubb3-GFP fusion protein under the endogenous Tubb3 promoter. Correct GFP knock-in was determined by cytoplasmic localization of the GFP signal. To ensure that cultured neurons were bona fide post-mitotic cells, the transfected neurons were treated with EdU for tracing proliferating cells. Five days after transfection, GFP expression was analyzed (FIG. 1F). It was found many neurons that expressed GFP in the cytoplasm, which co-localized with OM-Tubulin/Tuj1, confirming corrected gene knock-in (FIG. 1G). Importantly, the GFP+ cells were found EdU−, demonstrating that HITI-mediated gene knock-in events took place in non-dividing cells (FIG. 1H). Comparison of the three donor plasmids (1-cut (Tubb3-1c), 2-cut (Tubb3-2c) and minicircle (Tubb3-MC)) revealed that the 2-cut and minicircle donors had significantly higher GFP knock-in efficiency (~60%) per transfected mCherry+ neurons than the 1-cut donor (~30%) (FIG. M. GFP signal was found exclusively localized to the cytoplasm with the minicircle donor, whereas, 1-cut and 2-cut donors showed lower cytoplasmic distribution (FIG. 1J and FIG. 7). These results indicate that the inclusion of DNA sequences, such as a bacterial backbone and polyA, disrupts the endogenous localization pattern of Tubb3-GFP. The correct gene knock-in with minimal indels was further validated by PCR and sequencing (FIG. 1K, FIG. 8A and FIG. 8B). Comparison of the effects of different NLSs demonstrated a better knock-in efficiency with BPNLS than conventional SV40NLS in non-dividing neurons similar to dividing cells (FIG. 1L, FIG. 6A, FIG. 6B, FIG. 6C, FIG. 6D, and FIG. 6E). Furthermore, HITI was also effective for knocking-in GFP downstream of the human Tubb3 locus using human ESC-derived pan neurons (FIG. 9A, FIG. 9B, FIG. 9C, and FIG. 9D).

Example 4: In Vivo Genome Editing

Figure 2A:
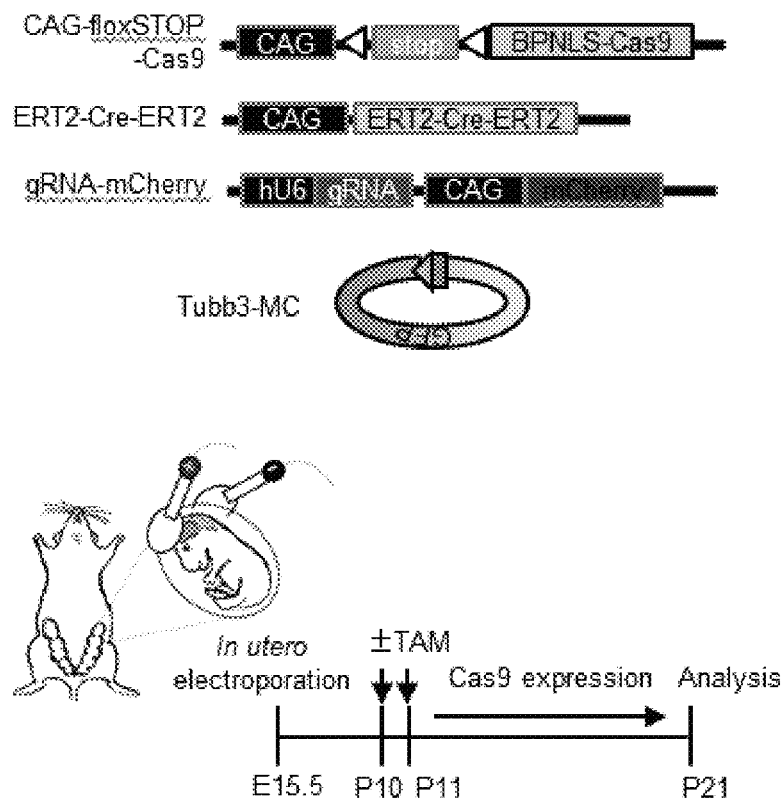
FIGS. 2A-2L show in vivo HITI via non-viral vectors.
Figure 2B:
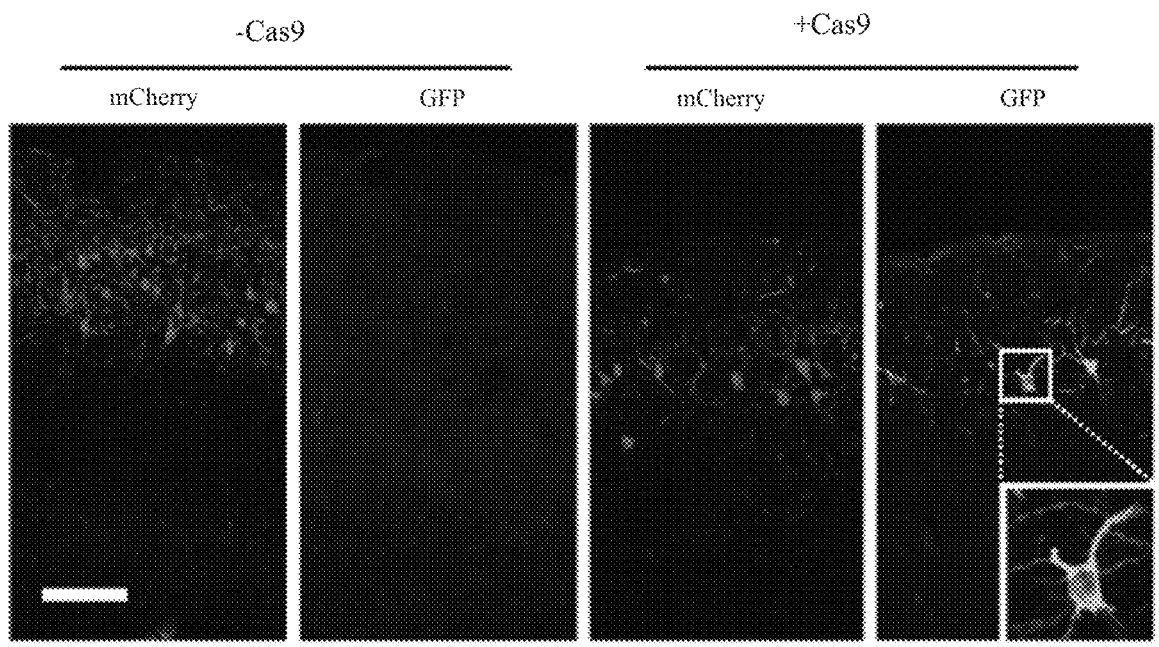
Figure 2C:
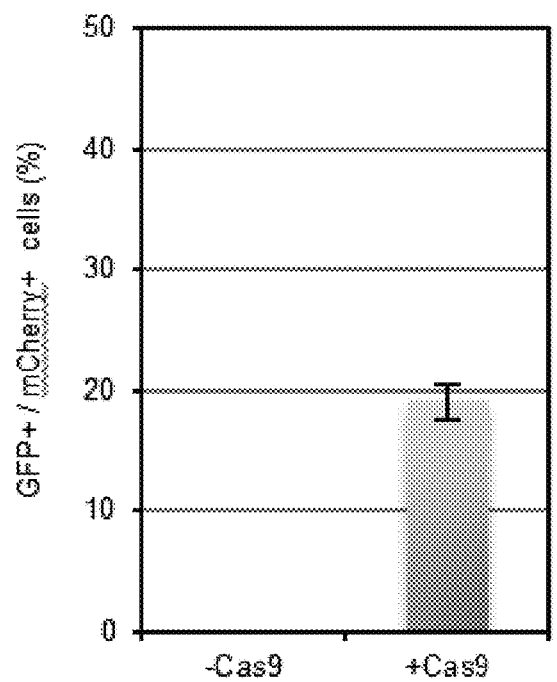
Figure 2D:
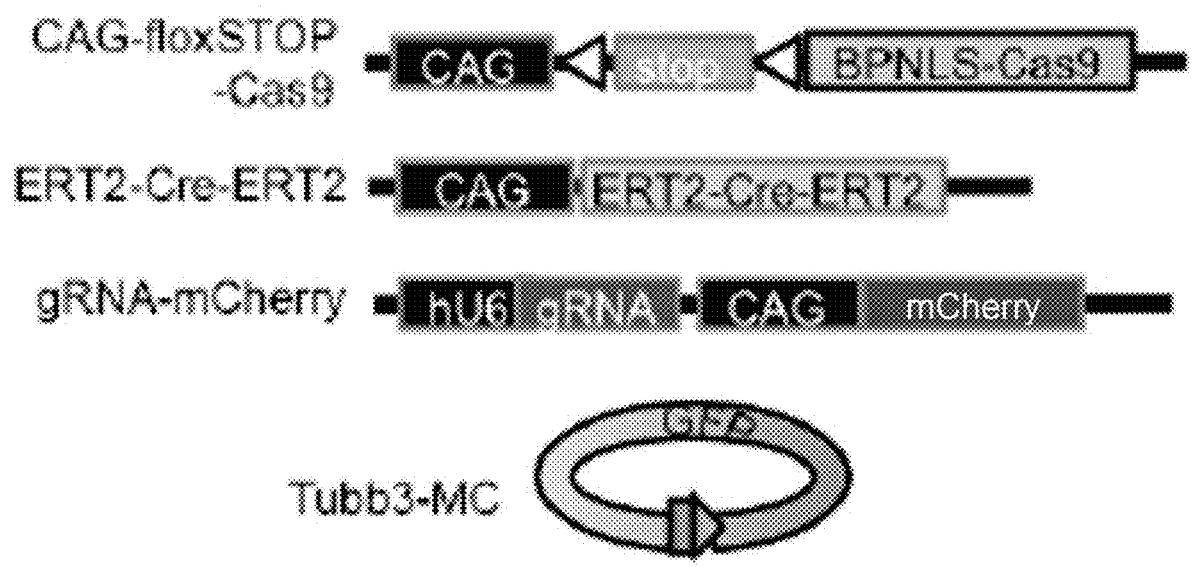
Figure 2E:
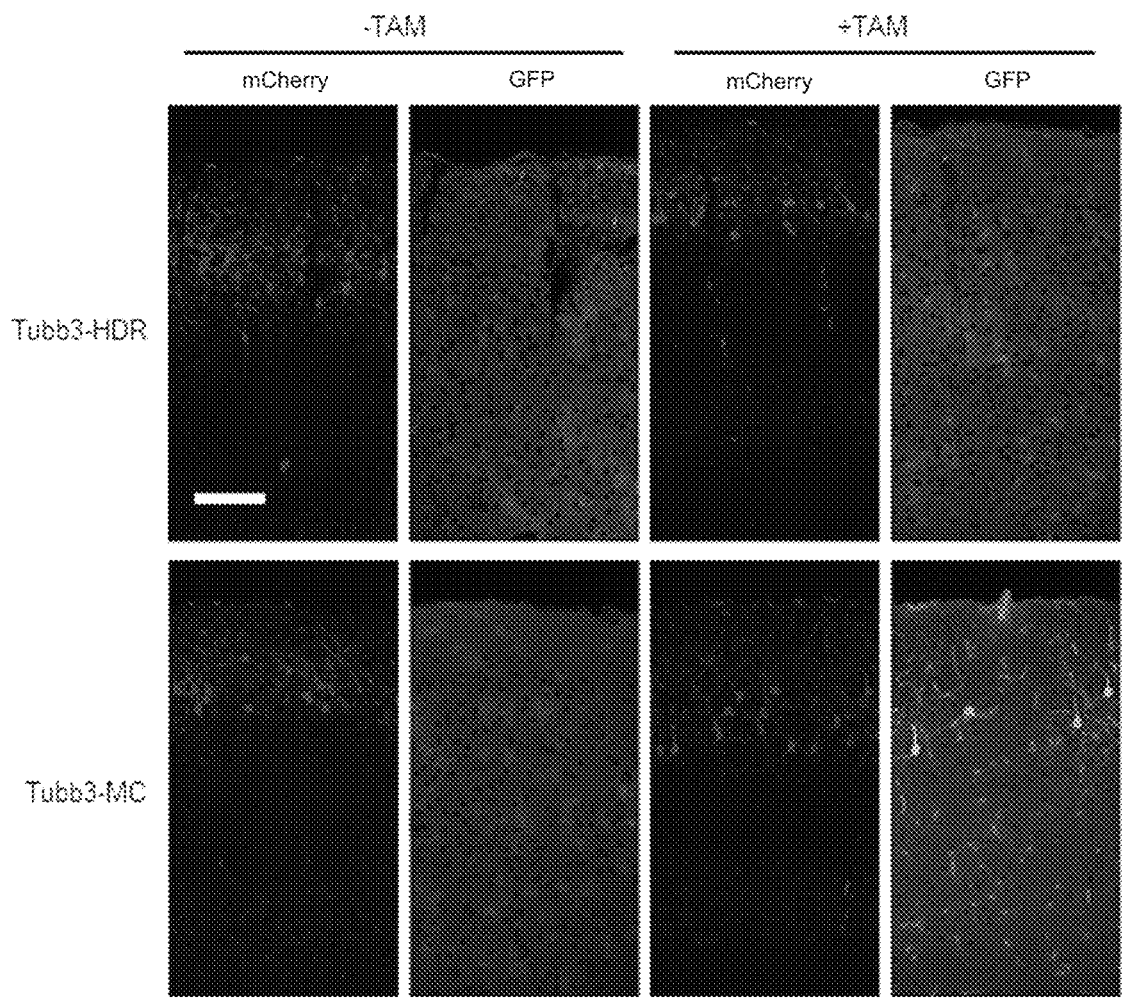
Figure 2F:
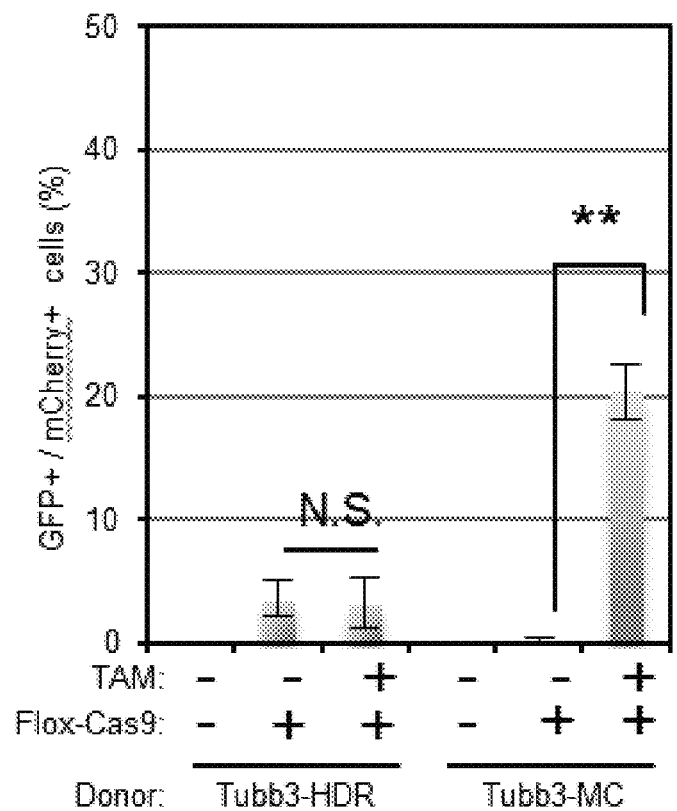

In vivo genome editing therapy offers several advantages over ex vivo strategies including a wider range of target cell types, especially those not amenable for in vitro culture, and thus has the potential to target multiple tissues. After successful demonstration of HITI in cultured cells the efficacy of HITI was determined in live animals. Based on the in vitro optimization studies, BPNLS-Cas9 was chosen with a minicircle donor for in vivo testing. A knock-in GFP at the Tubb3 gene locus was attempted in E15.5 mouse embryos by in utero electroporation, a well-established non-viral meditated in vivo gene-delivery method for brain studies. Three weeks after birth, twenty percent of successfully transfected cells (mCherry+) showed cytoplasmic GFP expression in the brain (FIGS. 2A-C). Of note, is that the electroporated progenitor cells at E15.5 with HITI constructs were still mitotically active, which prevented us from ascertaining whether HITI indeed occurred in non-dividing cells. To unequivocally demonstrate HITI-mediated postmitotic knock-in, a Tamoxifen (TAM) inducible Cre-dependent Cas9 expression system was delivered together with gRNA and Tubb3-MC donor into the E15.5 fetal brain via in utero electroporation. Cas9 expression was induced at P10 and P11 via TAM treatment, at which stage electroporated progenitor cells already differentiated to post-mitotic neurons (FIG. 2D). The results revealed a high GFP knock-in efficiency with Tubb3-MC donor DNA and little to no knock-in with a HDR donor (Tubb3-HDR) (FIG. 2E and FIG. 2F). These results indicate that HITI is also effective for targeted insertion of transgenes in post-mitotic cells in vivo.

Figure 2G:
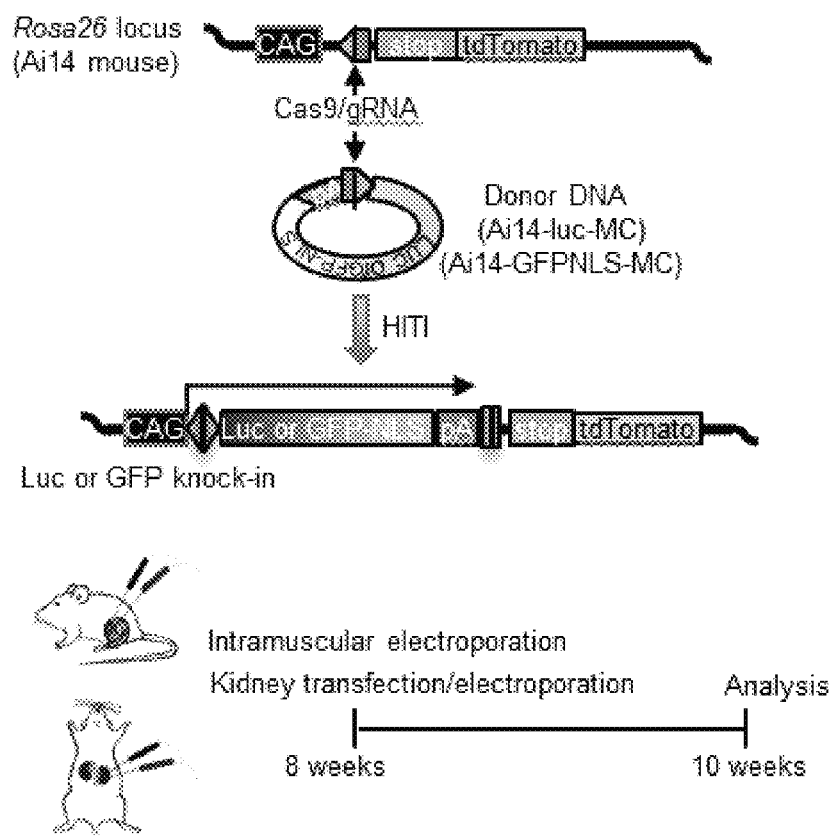
Figure 2H:
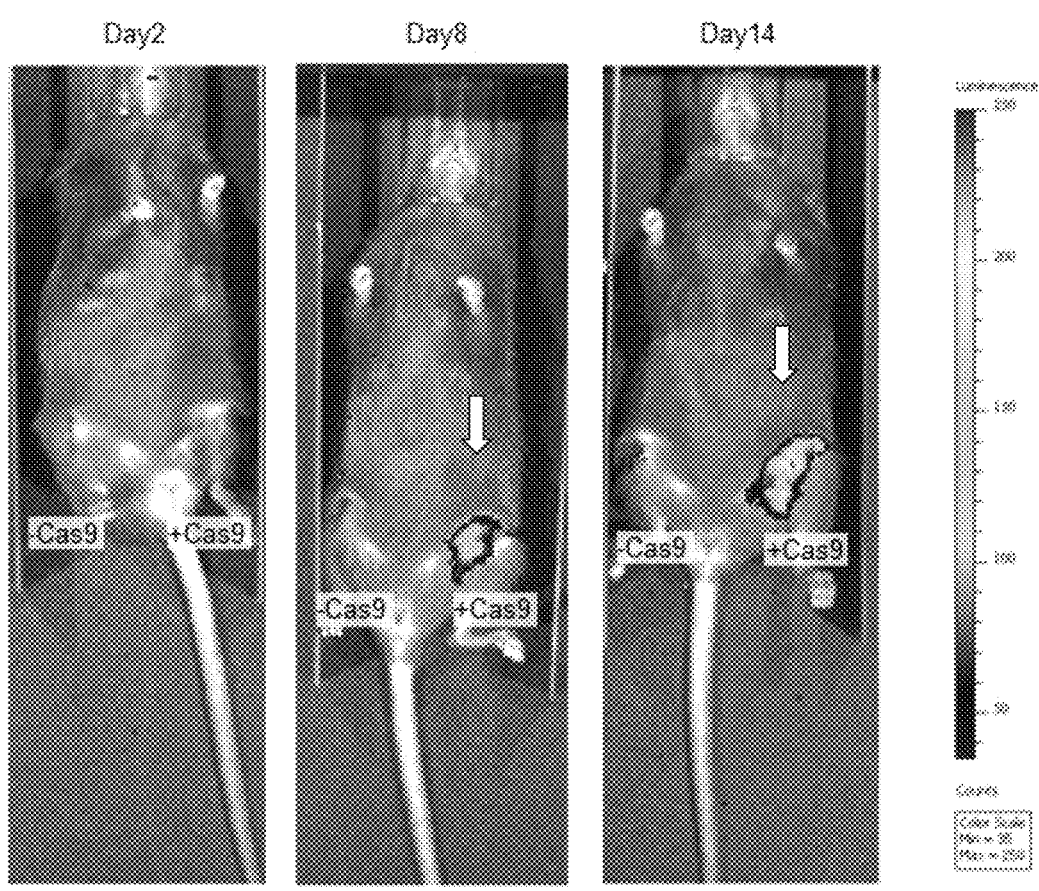
Figure 2I:
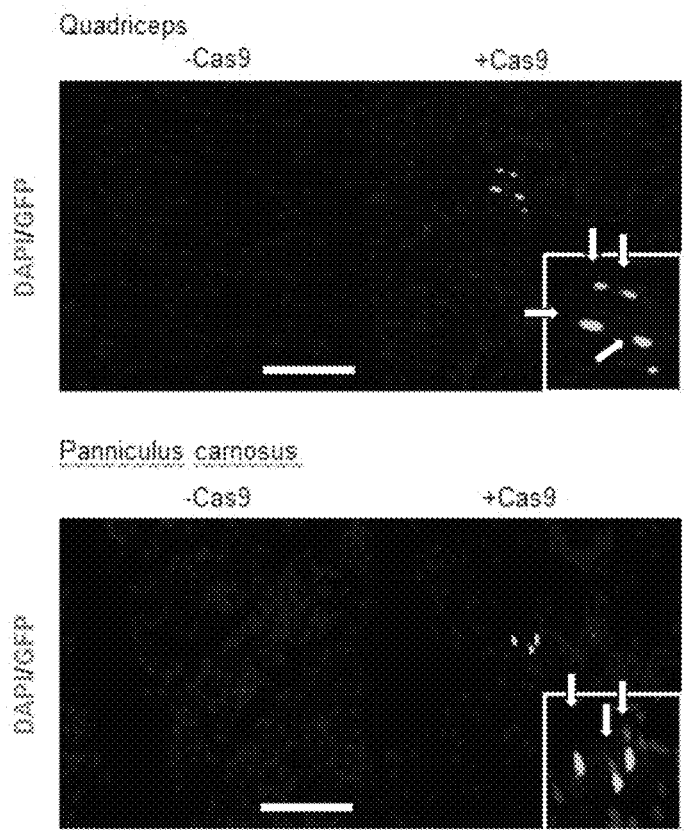
Figure 2J:
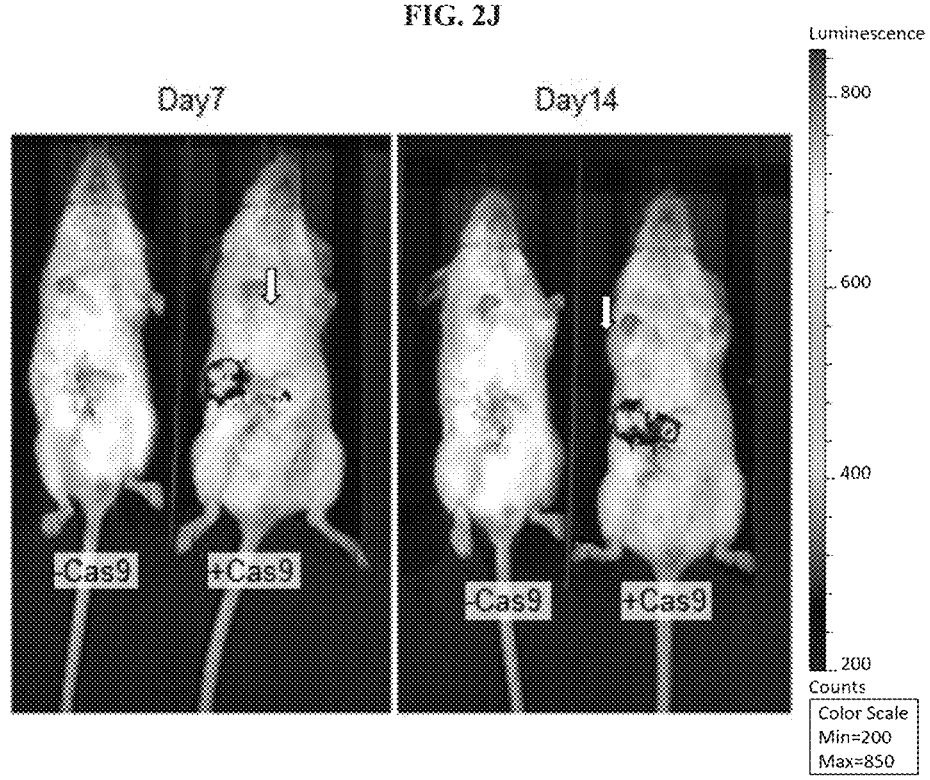
Figure 2K:
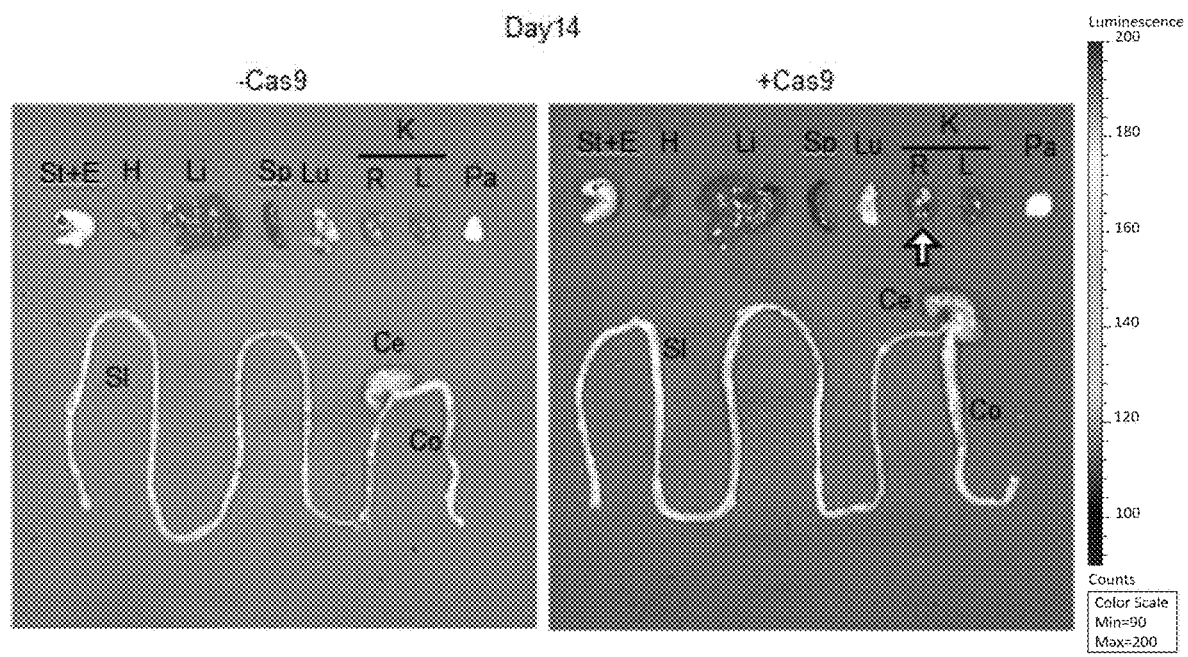
Figure 2L:
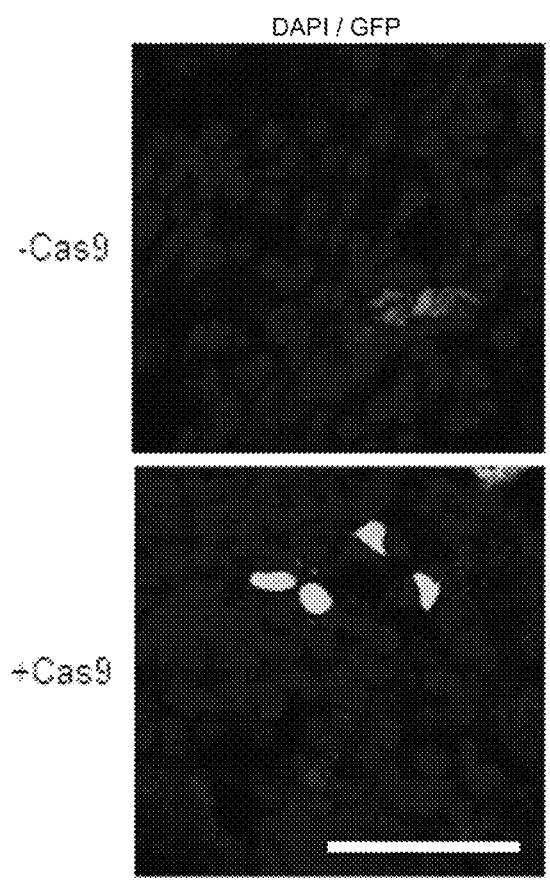

To broaden the utility of HITI for in vivo applications, targeted knock-in was tested using HITI plasmids in a variety of other somatic tissues. For this purpose the Ai14 mouse was used, which has a constitutively active CAG promoter inserted at the Rosa26 locus. To examine the efficacies of HITI to edit muscle and kidney tissues, GFP or luciferase coding minicircle donor plasmids (Ai14GFP-MC or Ai14luc-MC, respectively) were delivered together with BPNLS-Cas9 and gRNA by either electroporation or pressure-mediated transfection (FIG. 2G). Eight days post-electroporation luciferase signals were detected in quadriceps muscle cells for the luciferase minicircle donor (FIG. 2H). A small amount of nuclear localized GFP was also seen in quadriceps and panniculus muscle cells when the GFP minicircle donor was delivered (FIG. 2I). Similar results were observed in kidney (FIGS. 2J-L). These results demonstrate the applicability of HITI for targeted transgene knock-in for a variety of somatic tissues.

Example 5: Adeno-Associated Viral Delivery of HITI

Figure 3A:
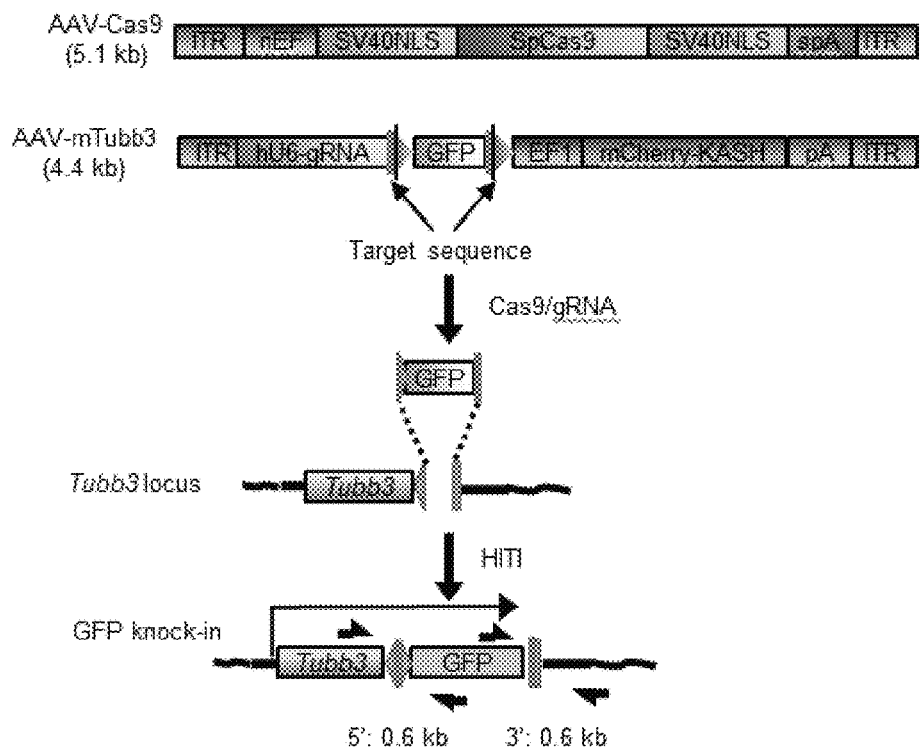
FIGS. 3A-3M show in vivo HITI via adeno-associated viral (AAV) vectors.
Figure 3B:
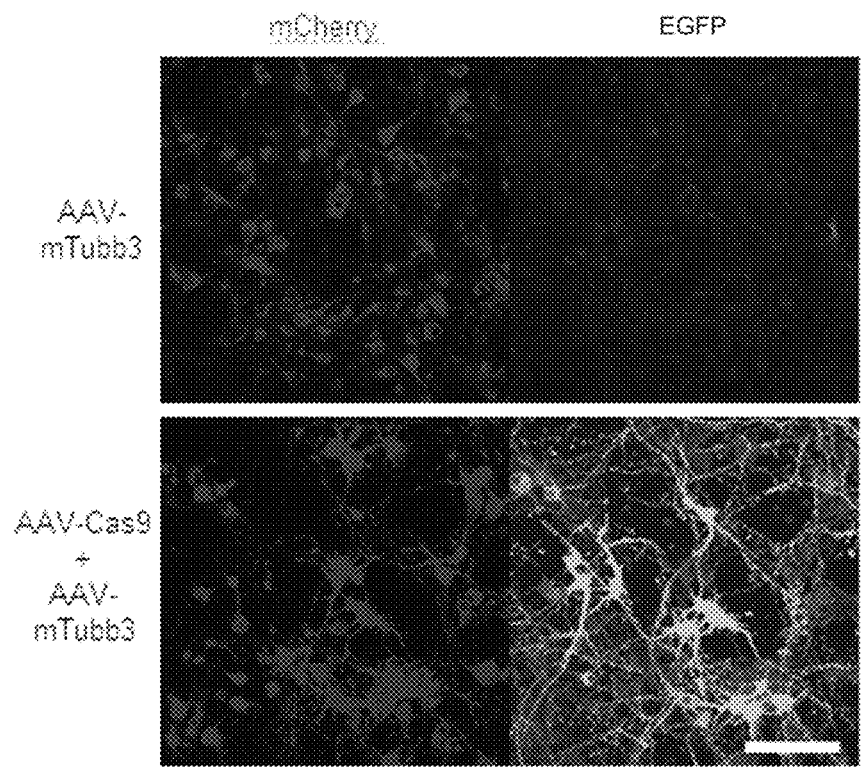
Figure 3C:
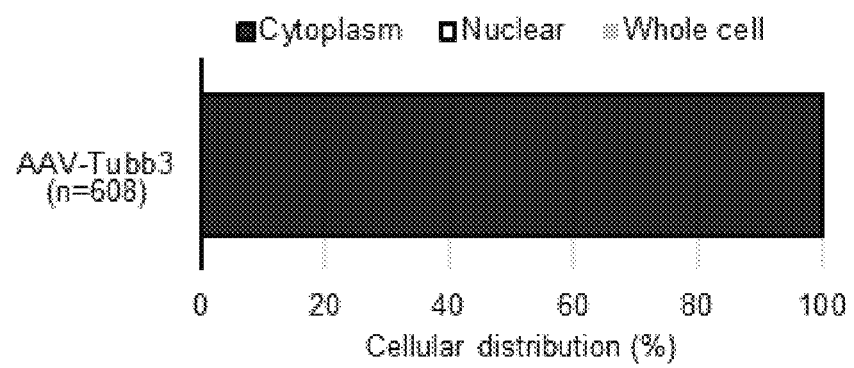
Figure 3D:
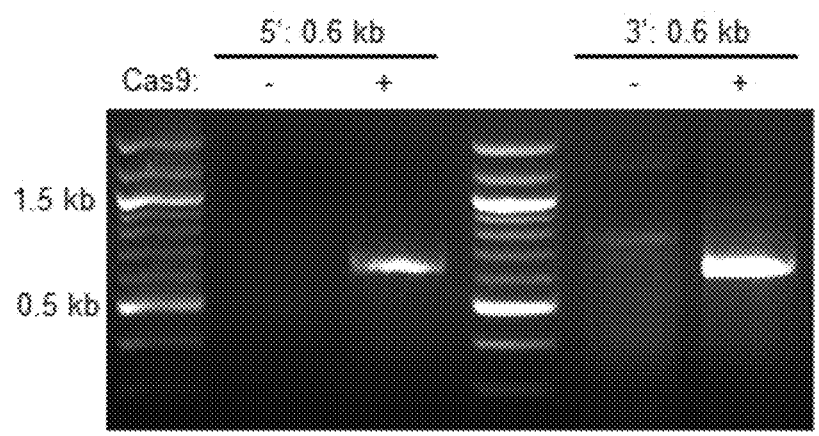
Figure 10A:
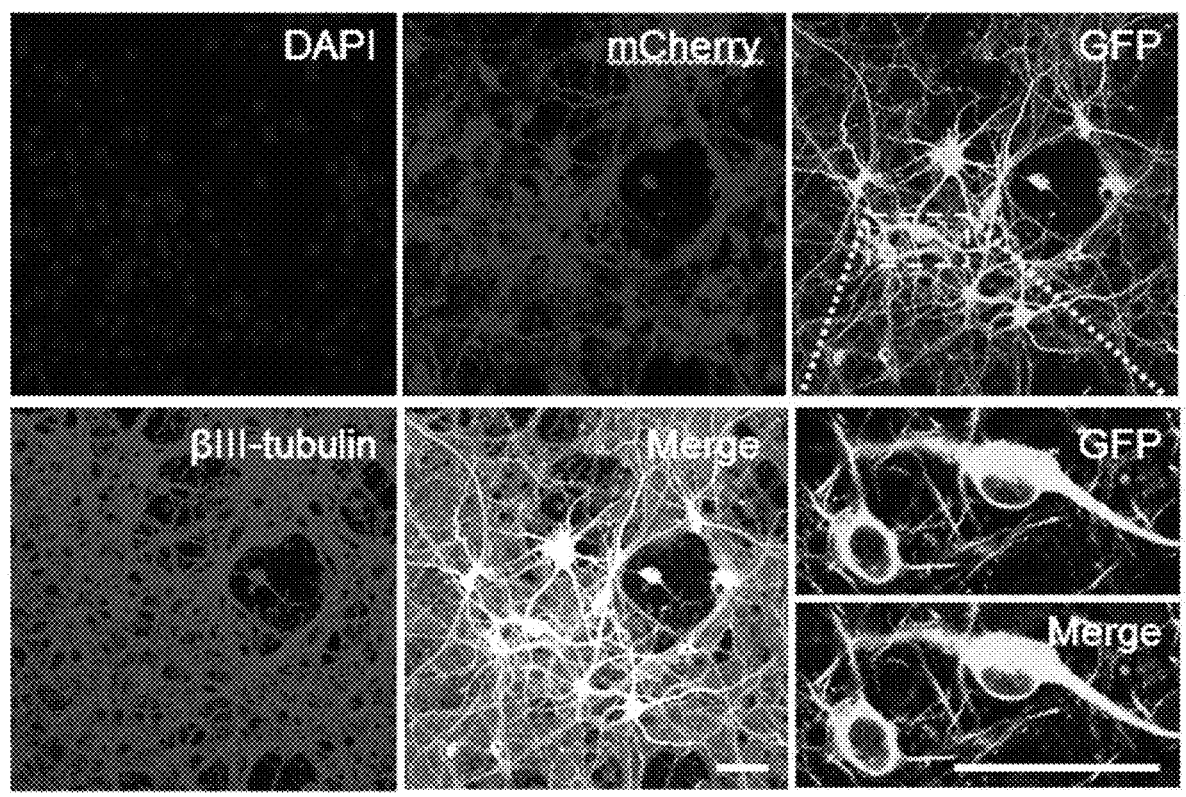
FIGS. 10A-B show AAV mediated HITI in mouse primary neurons.
Figure 10B:
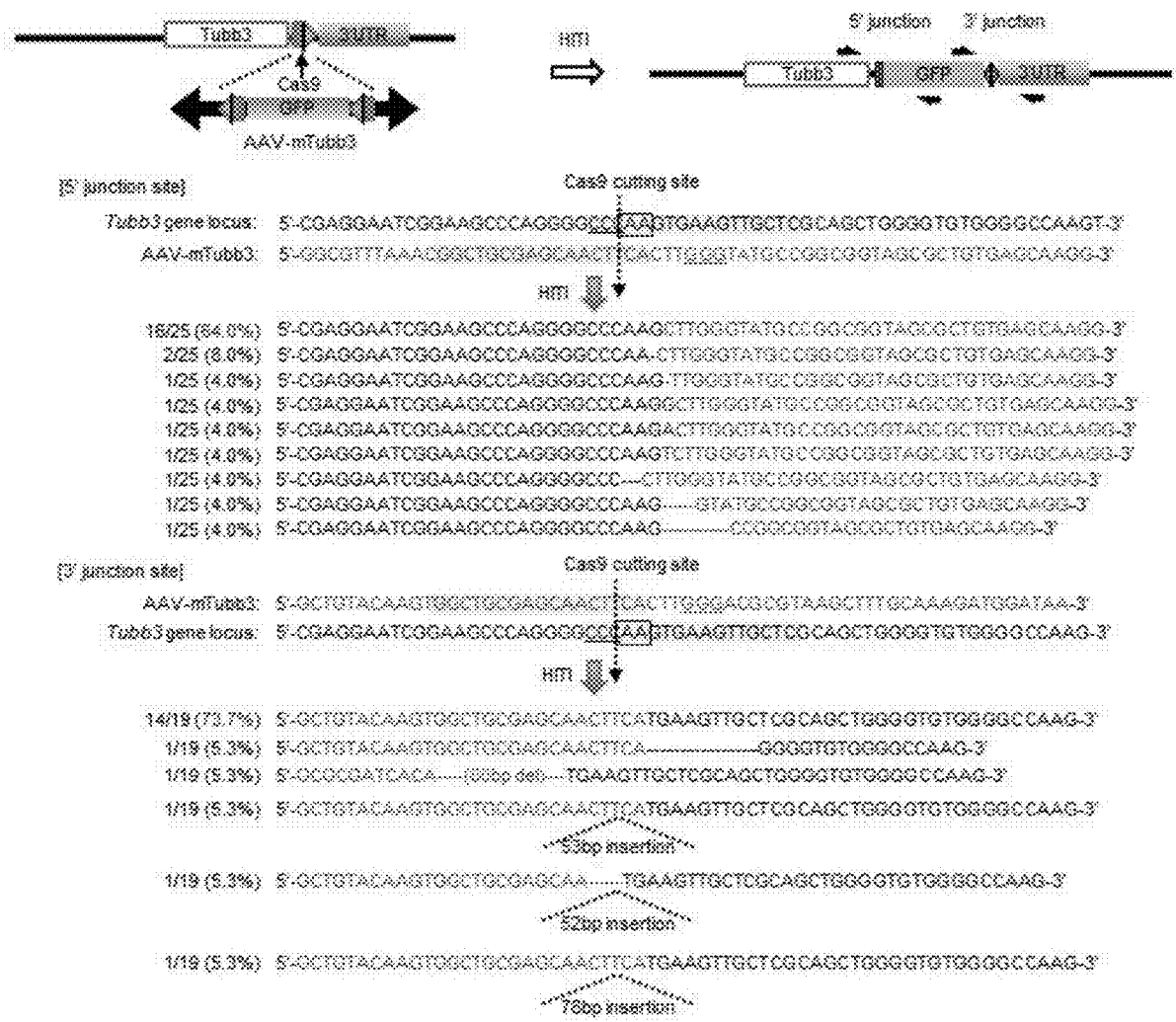

Although effective, plasmid delivery through electroporation and transfection is not efficient and robust for in vivo applications. For efficient and on-target in vivo gene delivery adeno-associated viral vectors (AAVs) are the method of choice. Thus, to attempt improving in vivo HITI efficiency and utility, Cas9, gRNA, and donor DNA were loaded into two AAV vectors. One of the vectors harbored a minimal constitutive hybrid promoter (nEF) driven Cas9 sandwiched by SV40NLS (instead of BPNLS due to the limited cloning capacity of AAV (AAV-Cas9)). The other vector was constructed to accommodate the Tubb3-gRNA expression cassette, 2-cut donor and a fluorescent marker (AAV-mTubb3). Both AAVs were packaged with serotype 8, which have previously displayed high infection capability for many organs and therapeutic safety (FIG. 3A). The AAV-Cas9 and AAV-mTubb3 co-infected cultured primary neurons expressed GFP in the cytoplasm, which co-localized with (3111-tubulin staining (FIG. 3B, FIG. 3C, and FIG. 10A). The fidelity of GFP knock-in was further confirmed by PCR and sequencing (FIG. 3D and FIG. 10B).

Figure 3E:
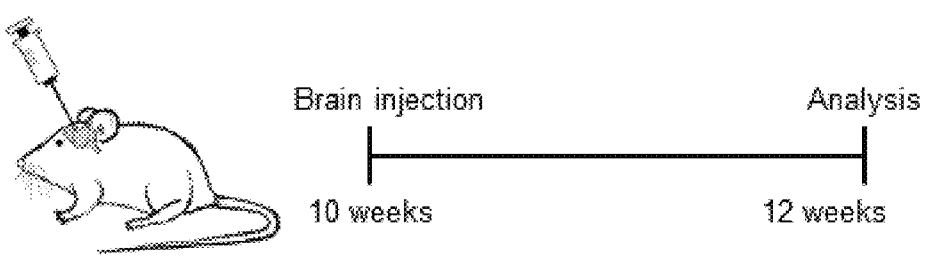
Figure 3F:
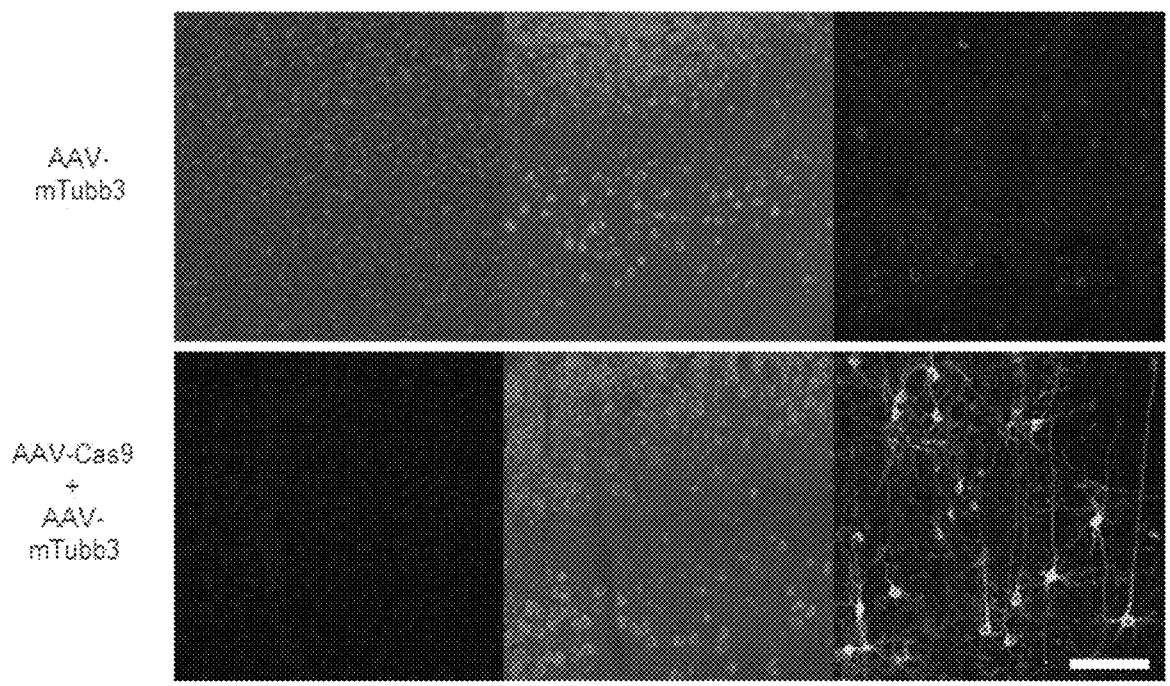
Figure 3G:
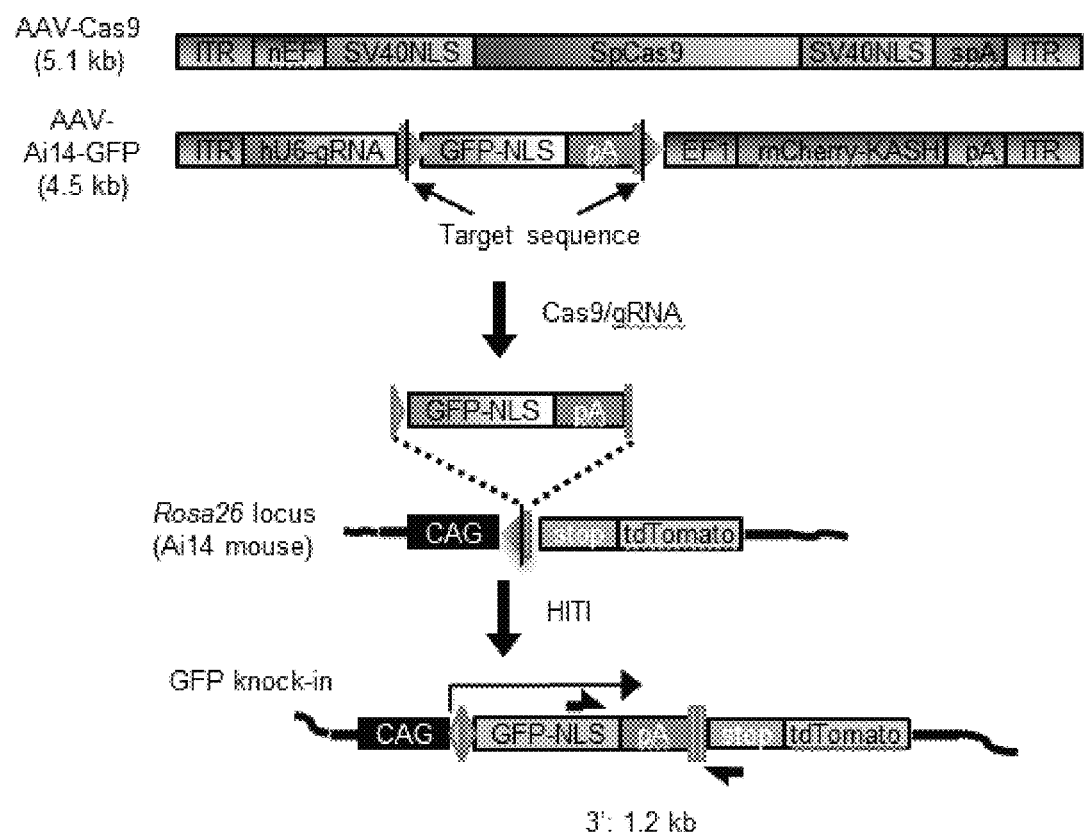
Figure 3H:
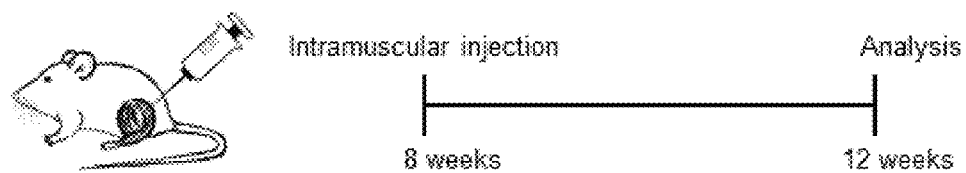
Figure 3I:
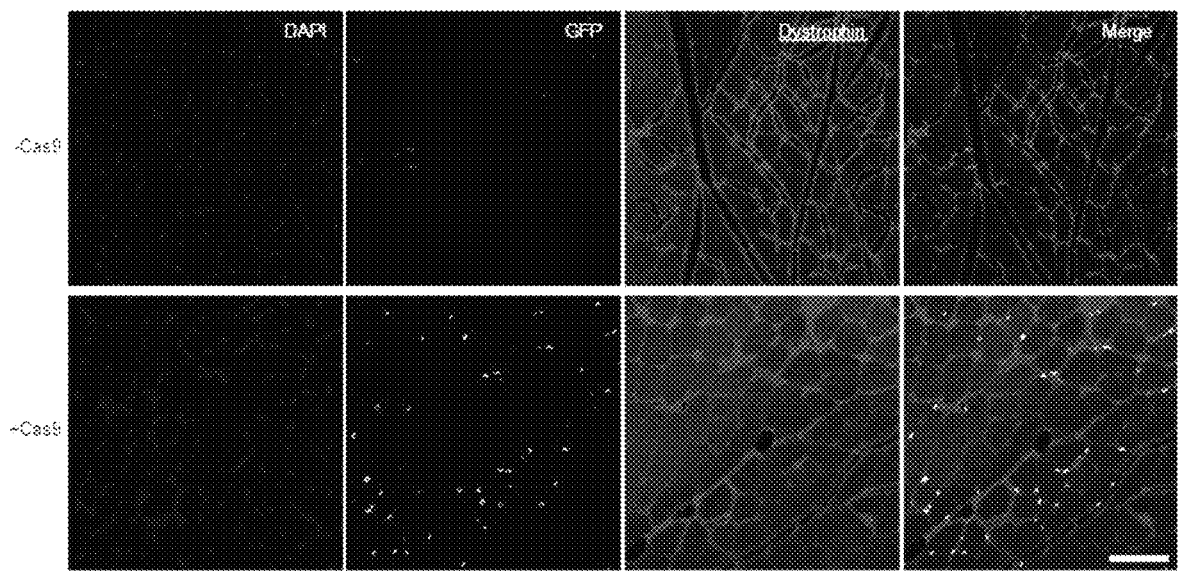
Figure 3J:
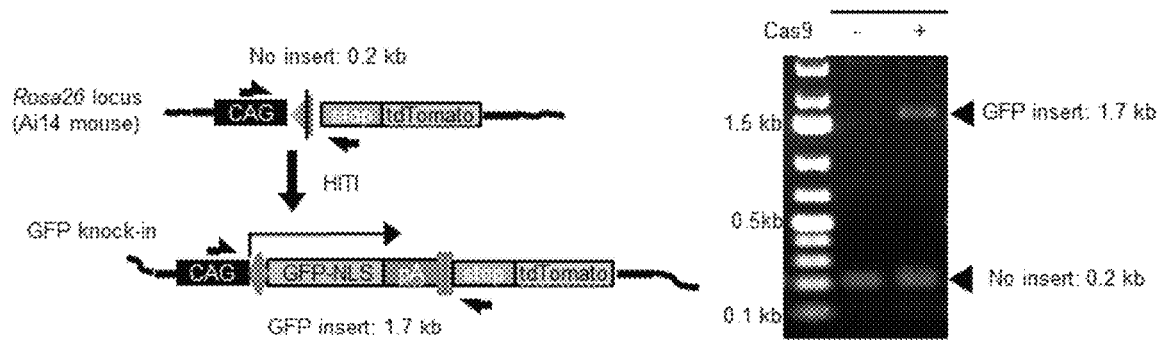
Figure 3K:
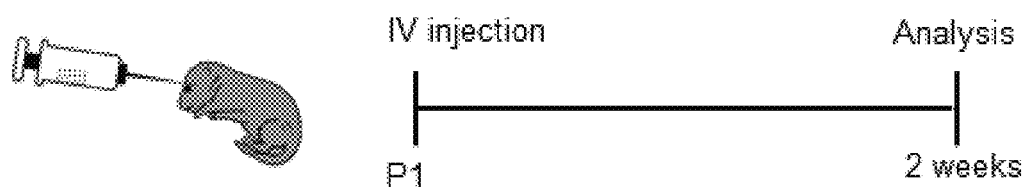
Figure 3L:
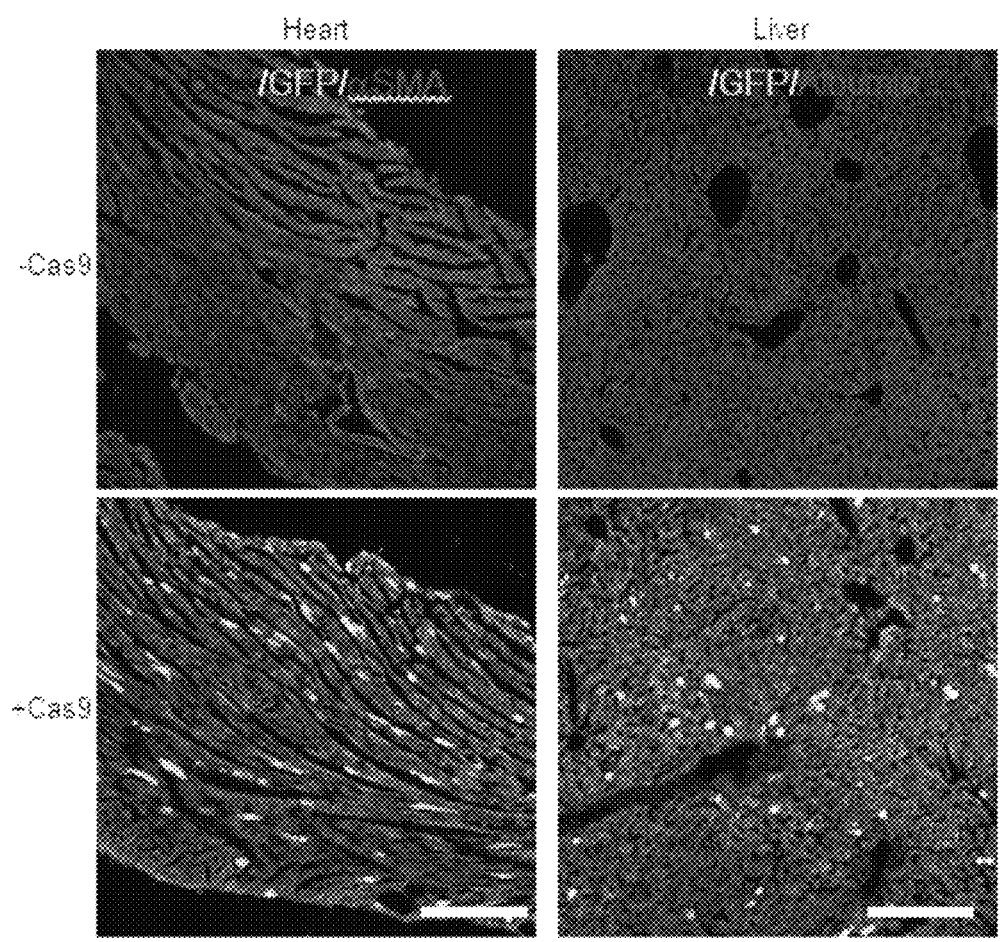
Figure 3M:
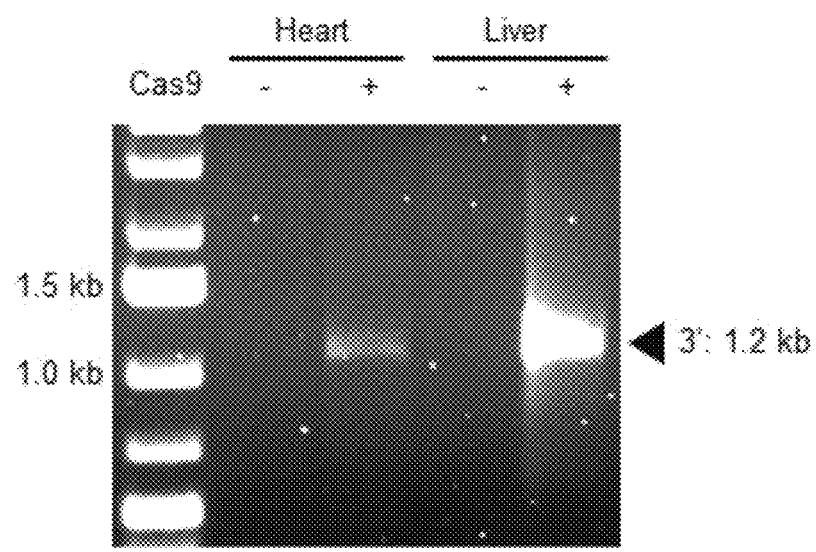
Figure 11A:
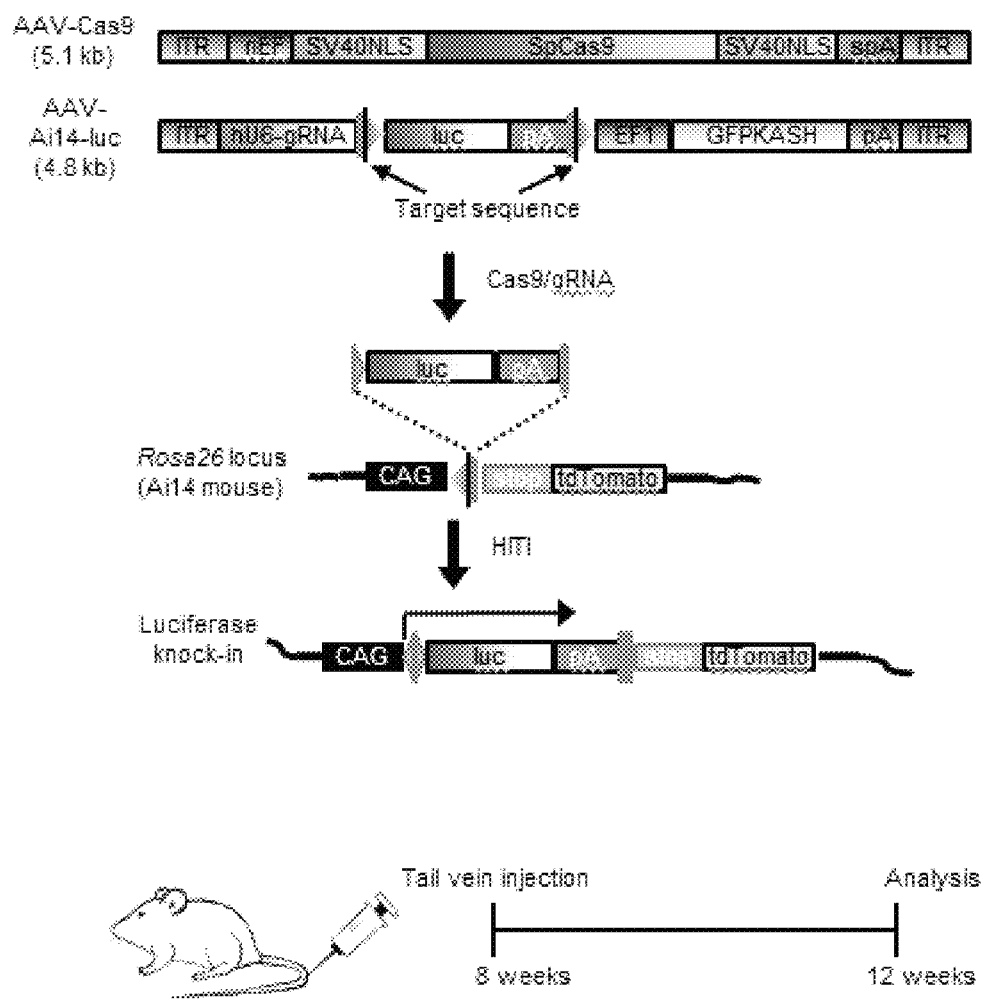
FIGS. 11A-11D show in vivo HITI via tail vein injection of AAVs in adult mice.
Figure 11B:
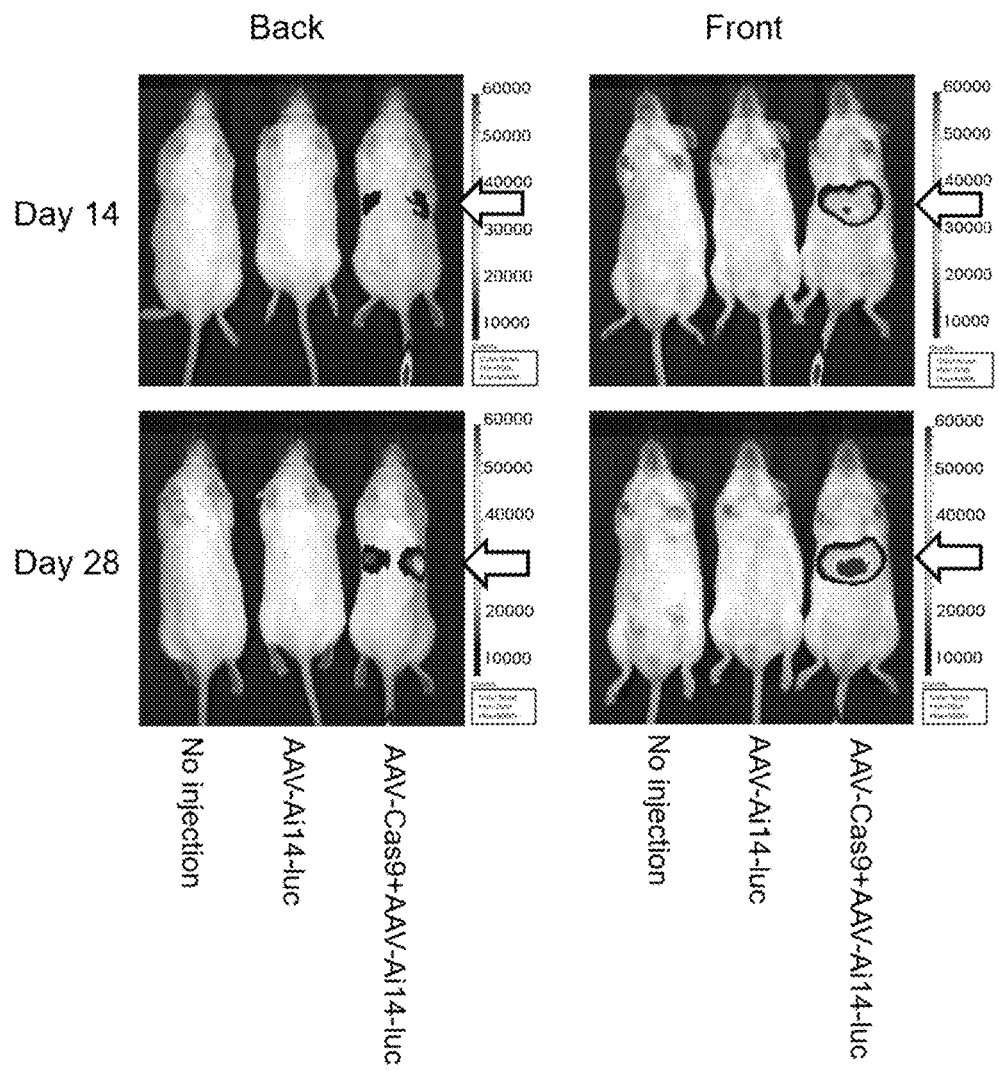
Figure 11C:
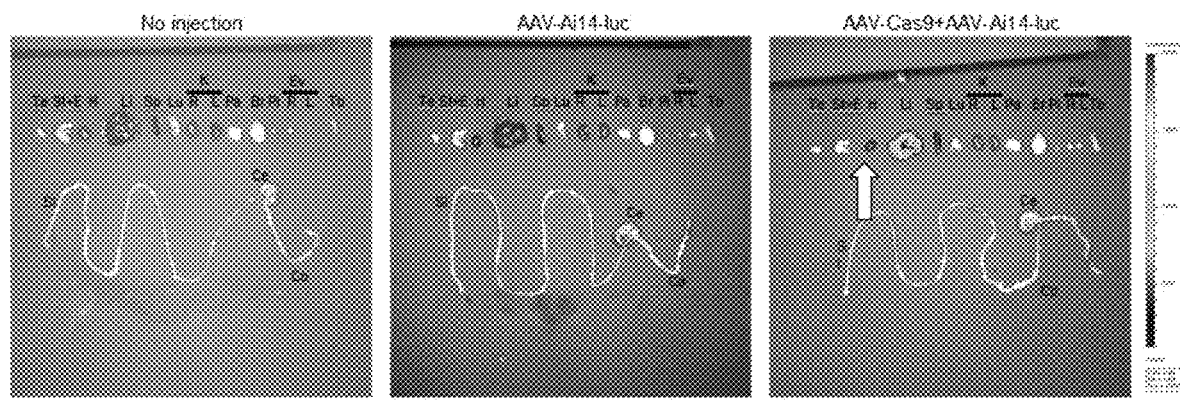
Figure 11D:
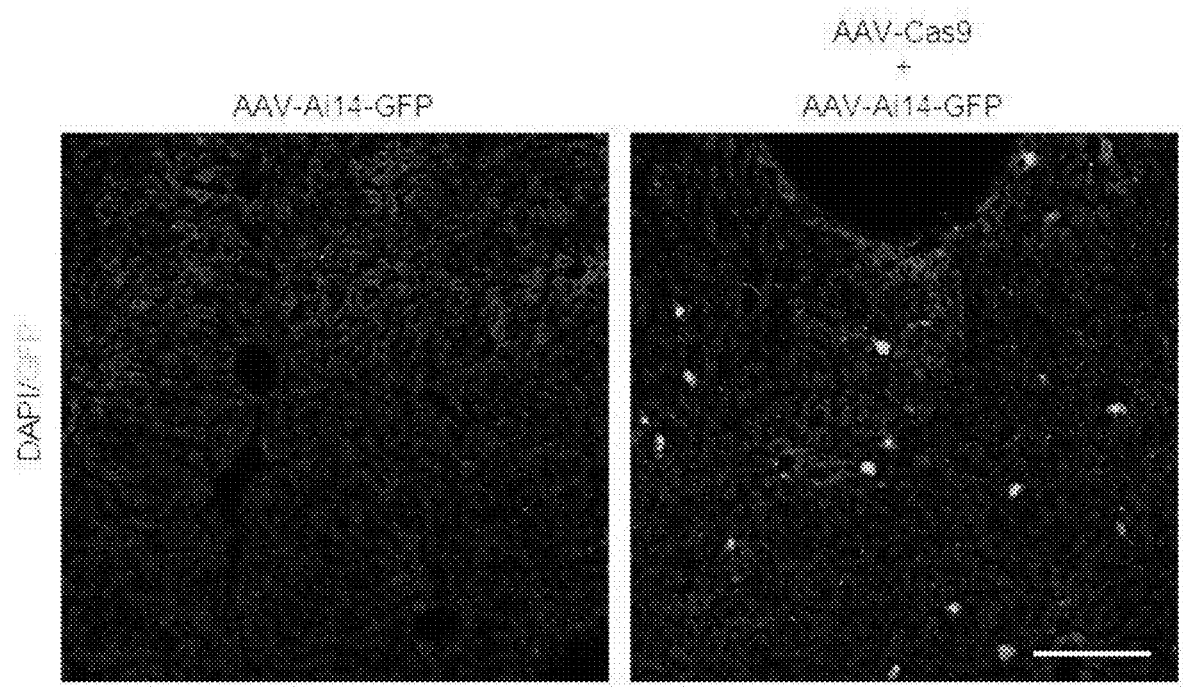
Figure 12A:
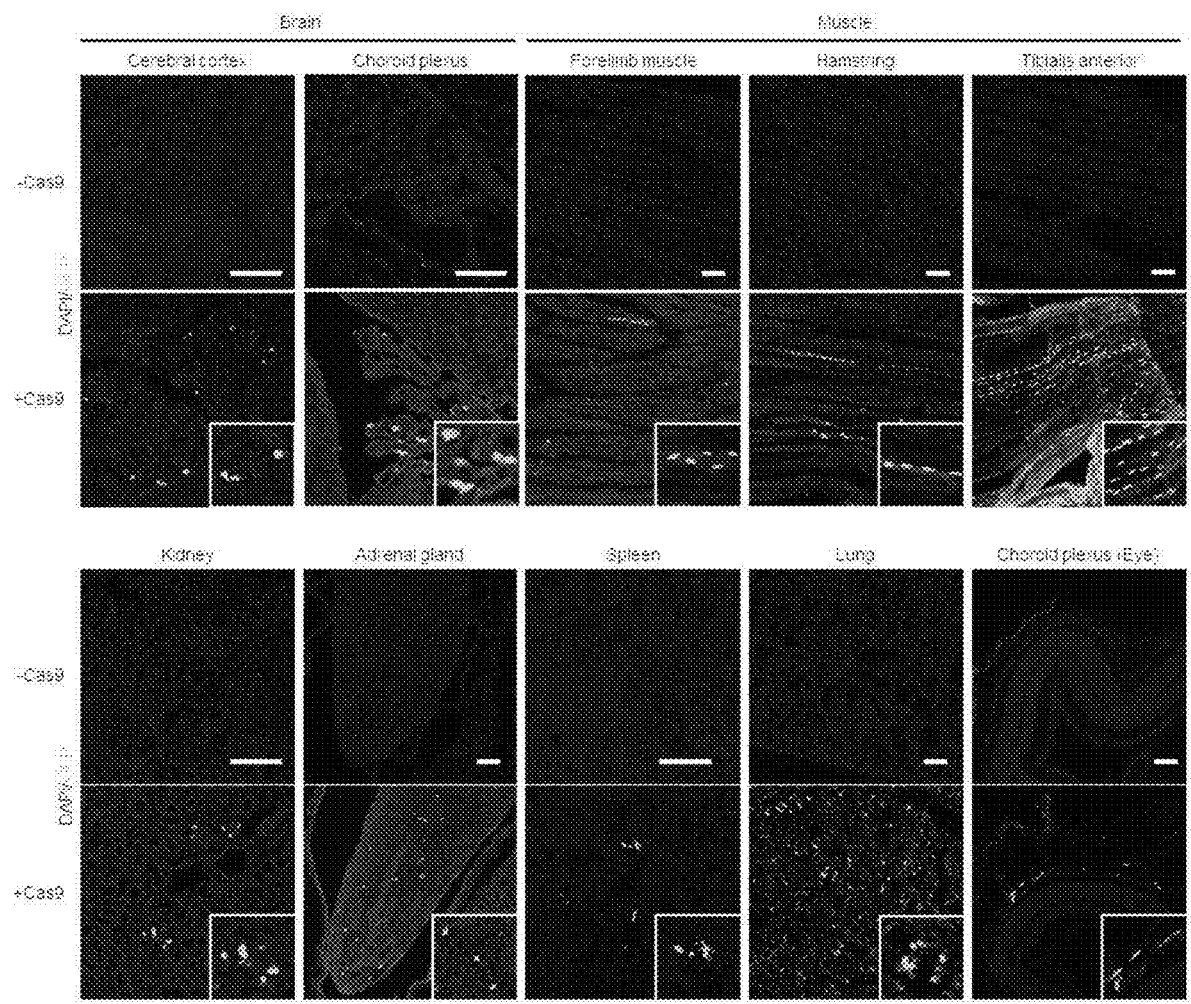
FIGS. 12A-12B show GFP-NLS gene knock-in via IV injection in neonatal mice.
Figure 12B:
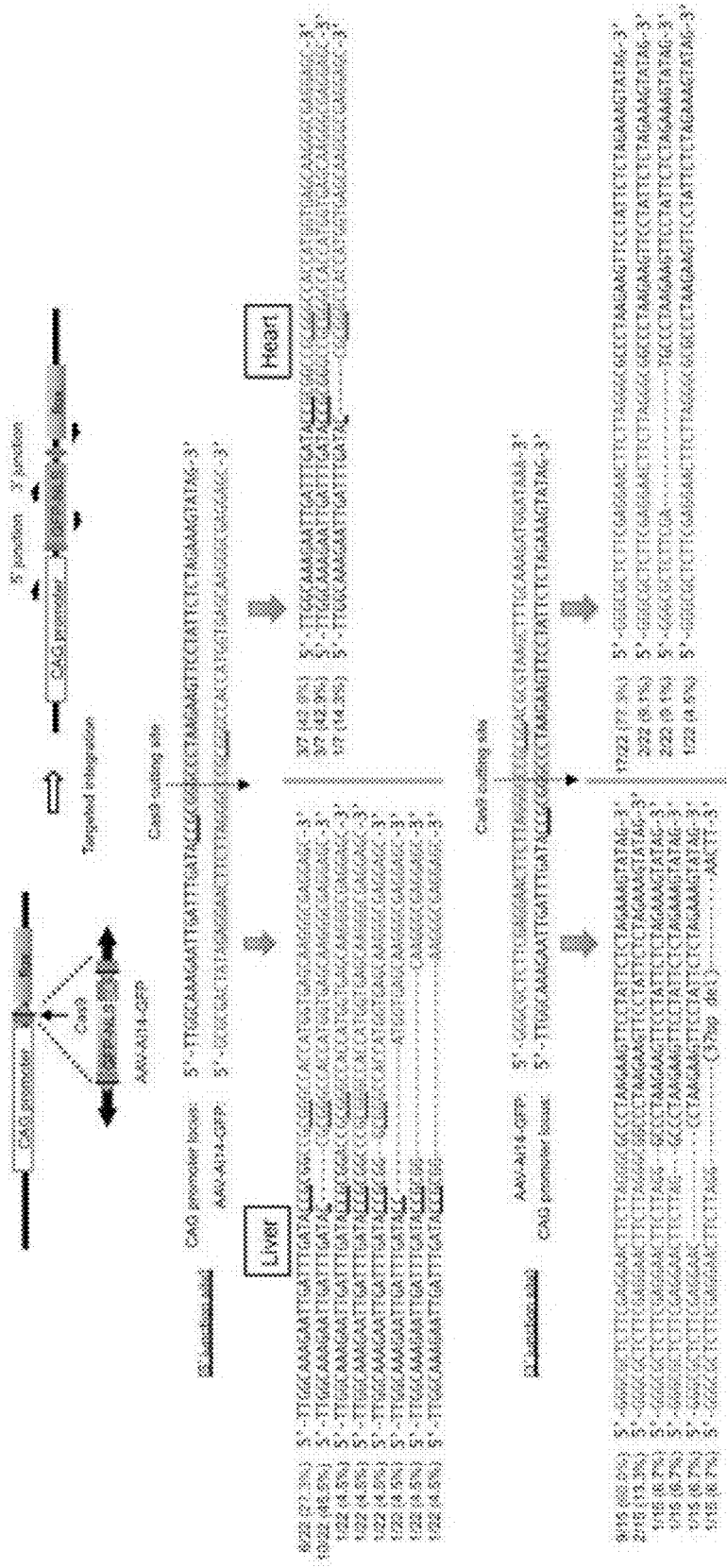

Next, AAVs were delivered to the visual cortex of the adult mouse brain via local injections. Two weeks later brain sections were prepared and stained with anti-GFP antibody (FIG. 3E). mCherry+ cells were observed both in the control (AAV-mTubb3 alone) and experimental groups (AAV-mTubb3+AAV-Cas9), indicating successful AAV infection (FIG. 3F). In contrast to control sections, where minimal GFP signal was detected, many cytoplasmic localized GFP+ neurons were found in the experimental group, supporting the notion that targeted gene insertion can be achieved with HITI in post-mitotic neurons (FIG. 3F). GFP and luciferase knock-in AAV were generated for the Ai14 mouse (FIG. 3G and FIG. 11A). Similar to the brain, local delivery through intramuscular (IM) injection in adult mice also showed correct GFP knock-in at the Rosa26 locus (FIGS. 3H-J). In addition to in situ injections, systemic delivery was also tested. To this end, the AAV-Cas9 and AAV-Ai14-GFP were co-delivered into neonatal Ai14 mice via intravenous (IV) injection. Two weeks post-infection, many GFP+ cells were observed throughout both the heart and liver of infected animals as well as in a broad range of other organ and tissue types including brain, muscle, kidney, adrenal gland, spleen, lung and choroid plexus of the eye (FIG. 3K, FIG. 3L and FIG. 12A). Genomic PCR and DNA sequencing analyses confirmed the correct knock-ins (FIG. 3M and FIG. 12B). Interestingly, it was observed that a preferential knock-in in adult liver after tail vein injection of AAVs (FIG. 11A, FIG. 11B, FIG. 11C, and FIG. 11D). To study the off-target effects of HITI in vivo, the mutation rates were examined of on-target and 12 predicted highest-ranking genomic off-target sites using AAV-infected liver tissue. Next-generation sequencing analysis suggested minimal insertion and deletion (indel) frequency at the examined off-target sites (FIG. 13).

Example 6: In Vivo Gene Therapy

Figure 4A:
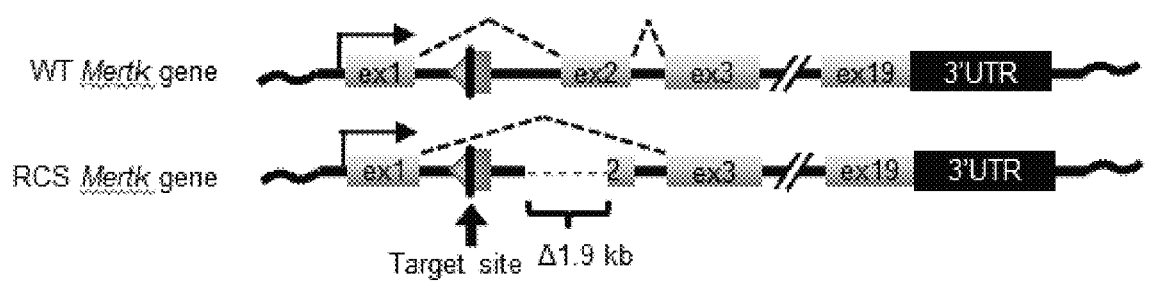
Figure 4B:
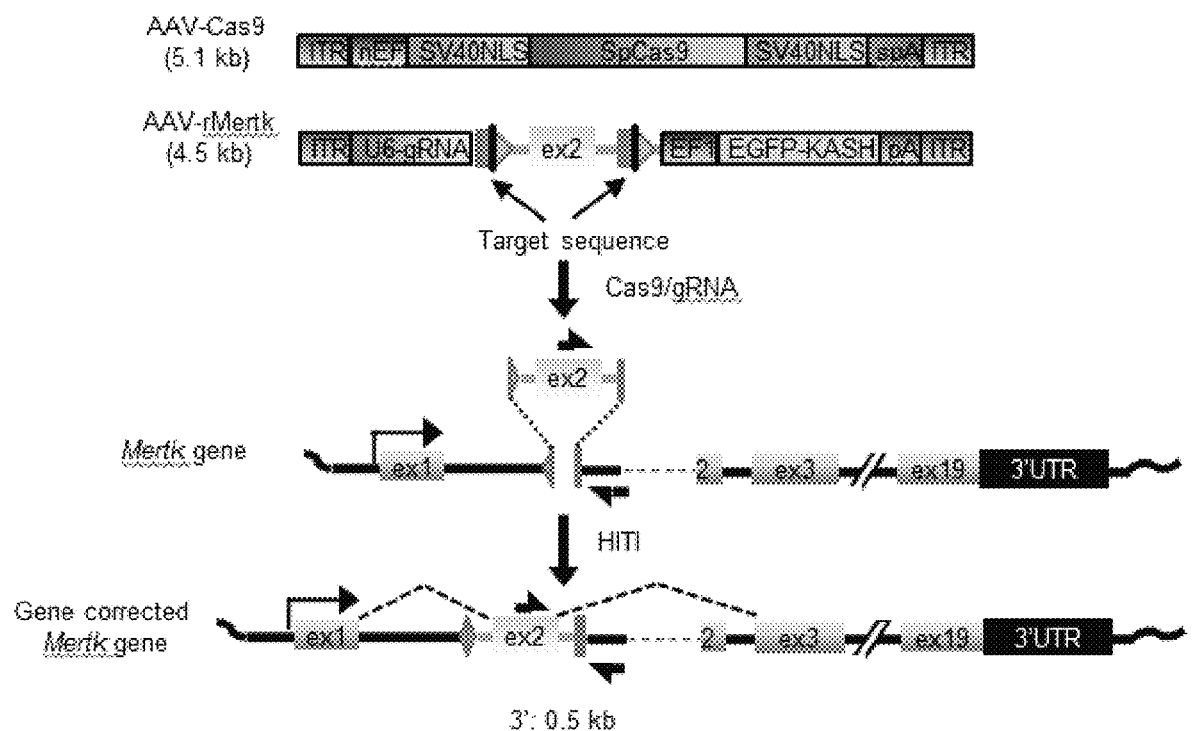
Figure 4C:
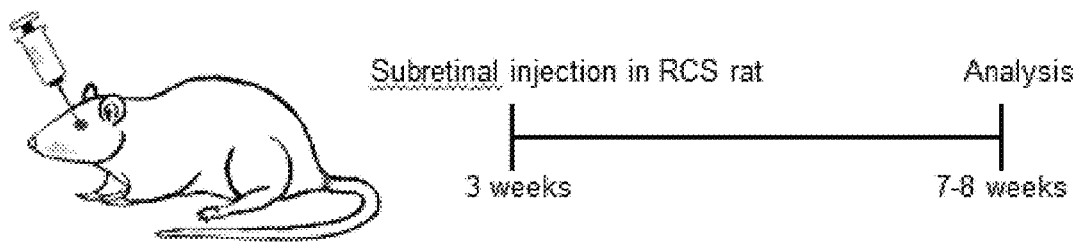
Figure 4D:
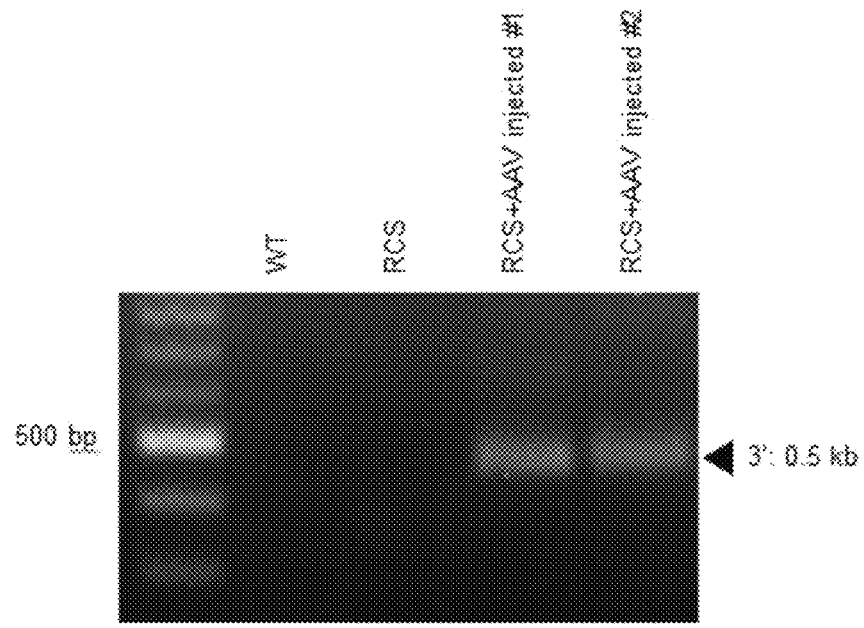
Figure 4E:
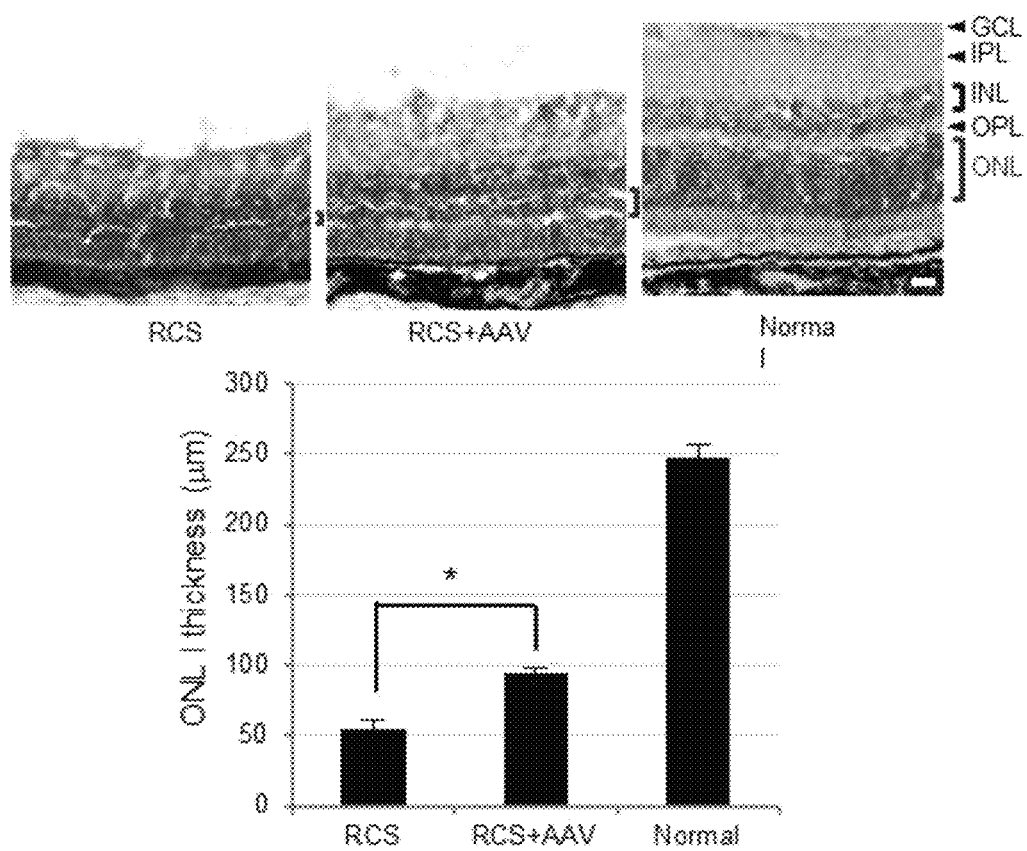
Figure 4F:
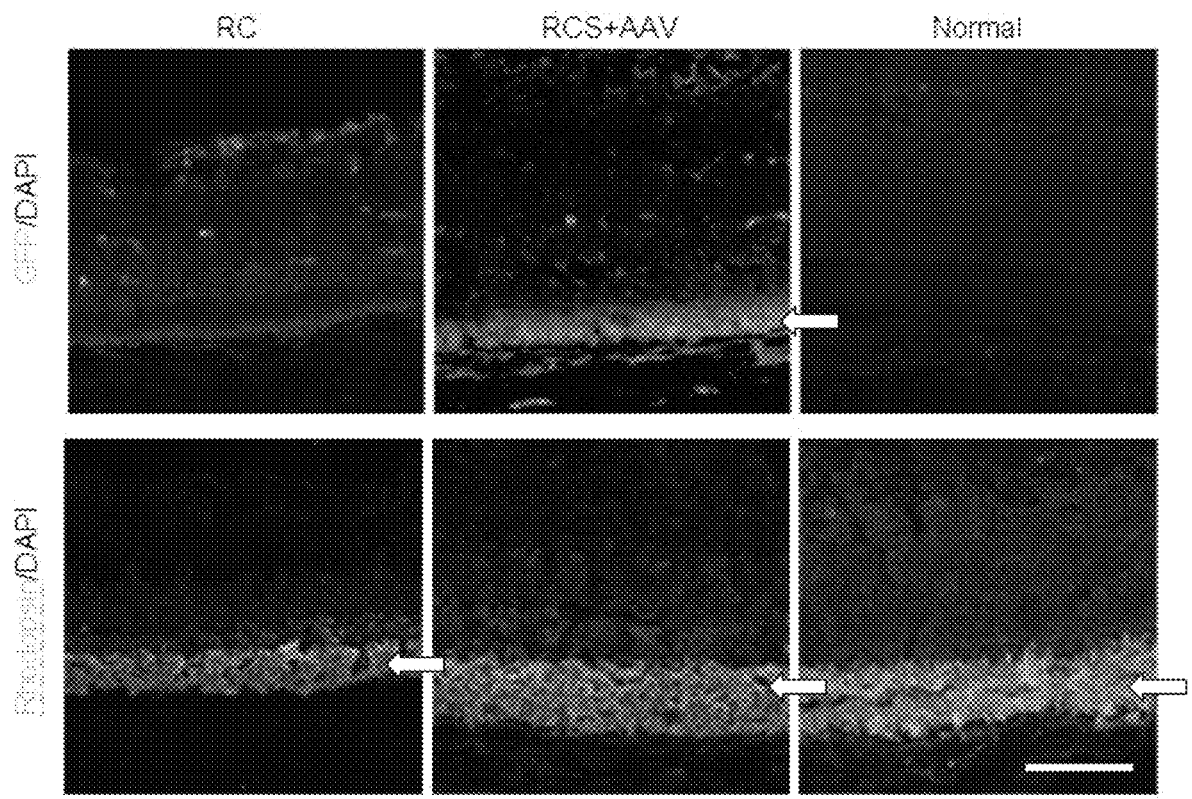
Figure 14A:
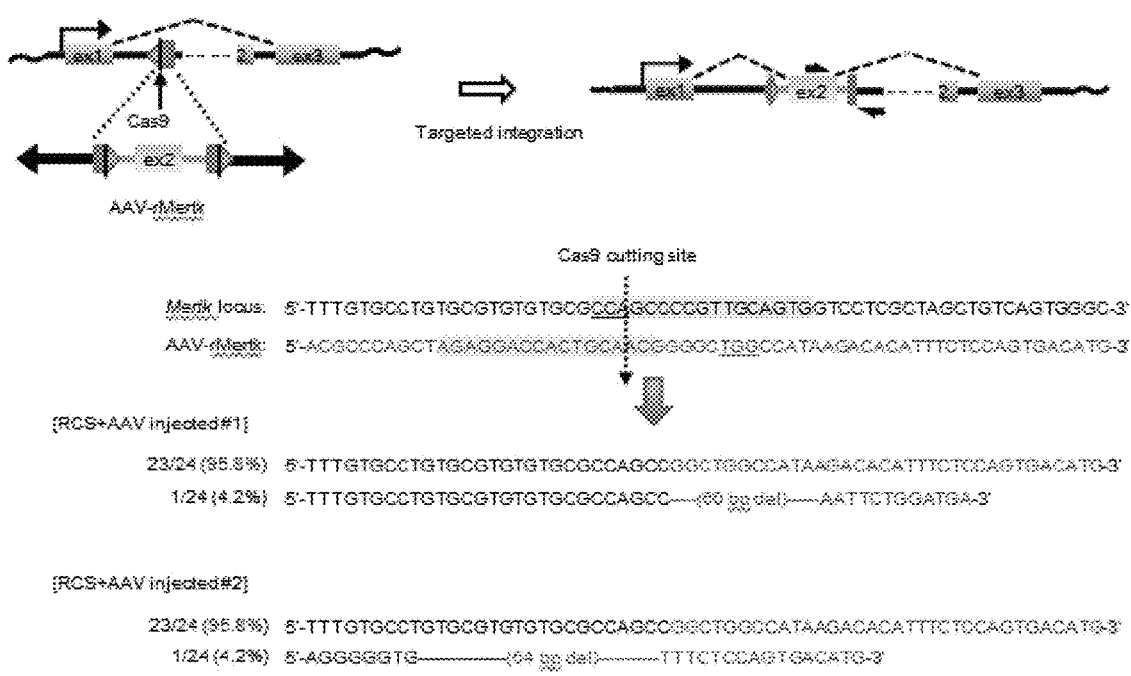
FIGS. 14A-14B show analyses of the gene corrected RCS rats via HITI.
Figure 14B:
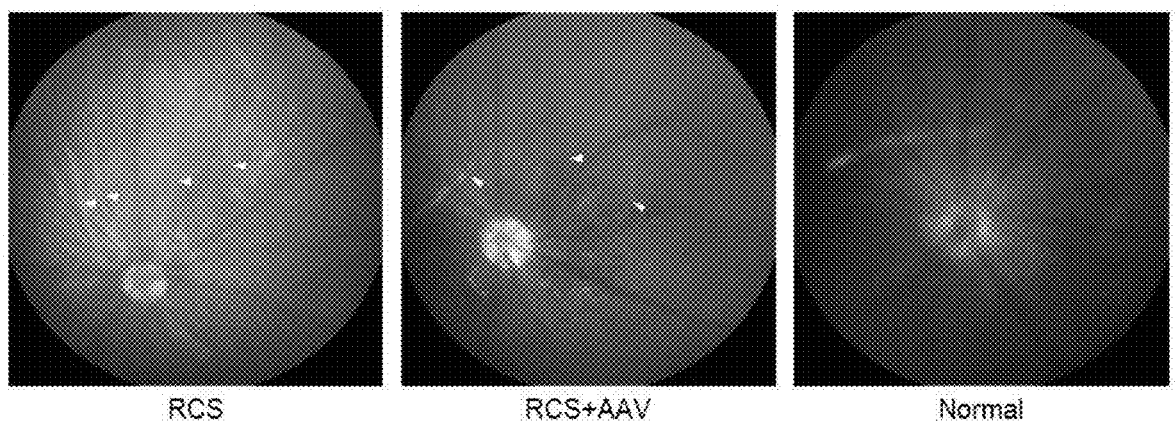

In addition to live tracking of specific post-mitotic cell types via reporter genes, and due to its high targeted knock-in efficiency, HITI might be harnessed towards targeted transgene integration for gene therapy. For a first proof-of-concept study, the Royal College of Surgeons (RCS) rat model was chosen. The RCS rat is a widely used animal model of inherited retinal degeneration called retinitis pigmentosa, a common cause of blindness in humans. A homozygous mutation in the Mertk gene, which harbors a 1.9 kb deletion from intron1 to exon2, results in defective phagocytic function of the retinal pigment epithelium. (RPE), with consequent. RPE and overlaying photoreceptor degeneration and blindness (FIG. 4A). Retinal degeneration in RCS rats can be evaluated by morphology and visual function testing via electroretinography (ERG). Morphological changes in the photoreceptor outer nuclear layer (ONL) degeneration appear as early as postnatal day 16 (P16) in RCS rats. To restore the retinal function of the Mertk gene in the eye, an AAV vector was generated that can integrate a functional copy of exon 2 of the Mertk gene at intron 1 (FIG. 4B). The AAV vectors were injected in rat eyes at postnatal 3 weeks, and analyzed at 7-8 weeks (FIG. 4C). From DNA analysis, correct DNA knock-in in the AAV injected eye was detected (FIG. 4D and FIG. 14A). AAV-Cas9 and AAV-rMertk injection had significant preservation of the ONL compared with untreated RCS rat controls (FIG. 4E). ME staining confirmed an increased photoreceptor ONL in the injected eye. In contrast, untreated eyes had only one-two or sparsely distributed photoreceptor cell bodies in the ONL. The average ONL thickness was 94±4.4 µm in treated eyes, compared with an ONL thickness of 54.6±6.8 µm in untreated eyes (P40.05). Expression of GFP transgene was increased in the RPE of treated RCS eyes (FIG. 4F). Similarly, expression of rhodopsin was increased in ONL of treated RCS eyes. To determine the effect of the treatment on retinal physiological function, ERG responses were tested at 4 weeks after injection (P50) to measure the electrical activity of rods and cones function (10 Hz flicker). All eyes treated with AAV-Cas9 and AAV-rMertk exhibited significantly improved ERG b-wave responses. The average b-wave value was 86.4±33.9 µV treated eyes, which is twice of that in untreated eyes (44.1±12.8 µV, P<0.05) (FIG. 4G), Similarly, 10 Hz flicker value, which measures cone response, was significantly improved and was more than 4-fold higher than that of the untreated eyes (21.9±1.0 µV vs 4.6±2.1 µV, P<0.05) (FIG. 414). Fundus photographs showed the visible large choroidal vessels, which is due to RPE atrophy, was improved in the AAV injected eyes (FIG. 14B). These results demonstrate that HITI-based AAV-Cas9 and AAV-rMertk treatment is able to rescue and preserve significant retinal visual function.

Example 7: In Vivo Gene Disruption

HITI, in some embodiments, is an efficient method for introducing mutations that introduce a gene disruption. A gene disruption comprises a mutation in the coding sequence or the promoter/enhancer elements of a gene, resulting in a mutated or deleted gene or reduced expression of a gene. In some embodiments, overexpression of a gene, for example an oncogene, causes disease in a human patient.

A knockout is created in a mouse model of cancer, KRAS, where KRAS is overexpressed causing cancer in the mouse. A targeting construct is designed having a sequence corresponding to a promoter/enhancer element of the KRAS gene, including a deletion in the promoter/enhancer element, which results in decreased expression of the KRAS gene. The targeting construct is packaged into an AAV-delKRAS construct and co-administered with an AAV-Cas9 construct. The delKRAS fragment from the promoter/enhancer of KRAS is integrated into the mouse. Treated mice express less than mice that have been treated with a control virus. Also, treated mice have fewer tumors than mice treated with the control virus.

This example shows that HITI technology can be used to disrupt or knock-out or disrupt a gene, such as a disease causing gene.

Example 8: Measurement of Knock-In Efficiency

Figure 15A:
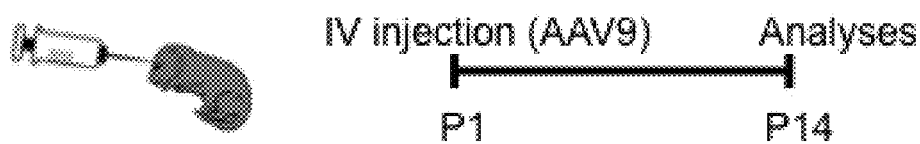
FIGS. 15A-15C show efficacy of knockin using a GFP HITI AAV9 construct.
Figure 15B:
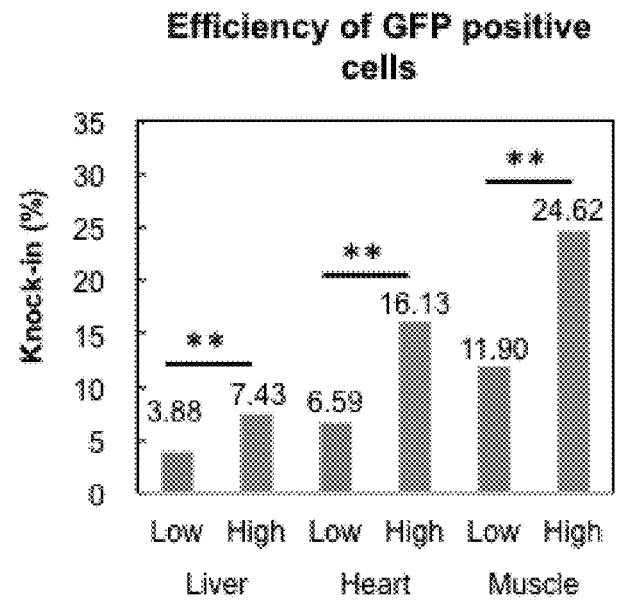
Figure 15C:
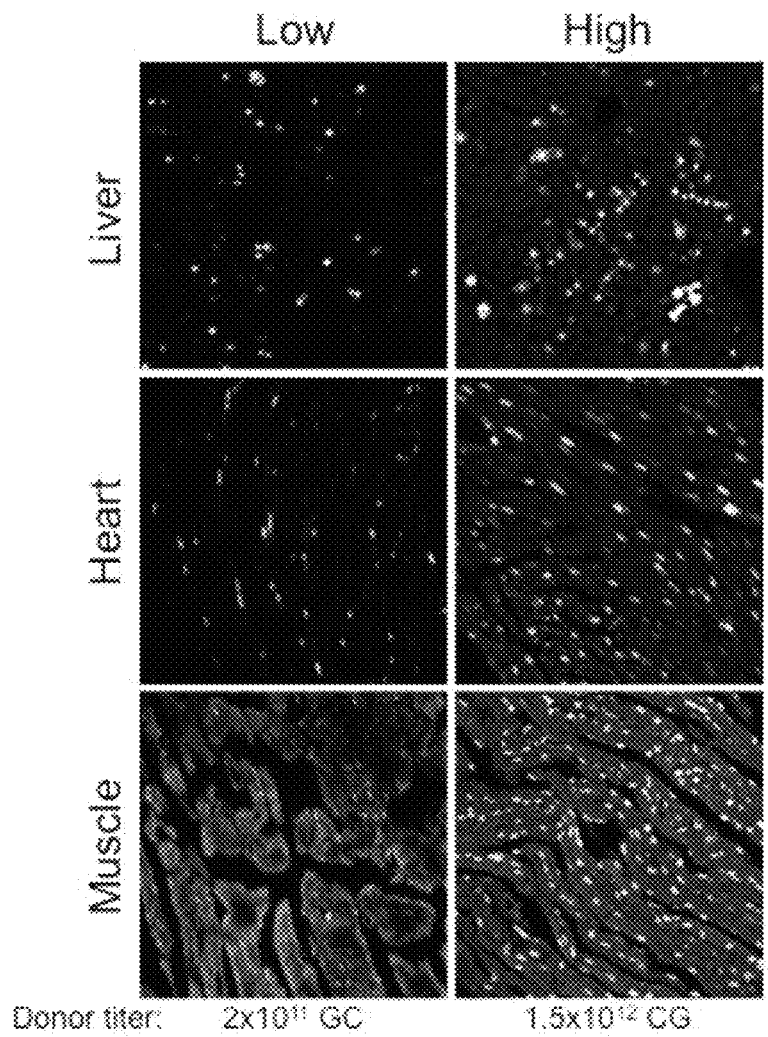

Efficiency of knock in was measured in mice treated with IV injection of AAV9 expressing the HITI constructs. FIG. 15A shows a schematic for treatment. FIG. 15B shows percent of GFP positive cells that show knock-in at high and low viral titer. FIG. 15C shows a photomicrograph of GFP positive cells in liver, heart, and muscle. This data shows gene knock-in efficiency is dependent on the titer of infected AAVs. With the high AAV titer used ($1.5 \times 10^{12}$), it was possible to knock-in GFP up to 25% (muscle).

Example 9: Treatment of Progeria

Figure 16A:
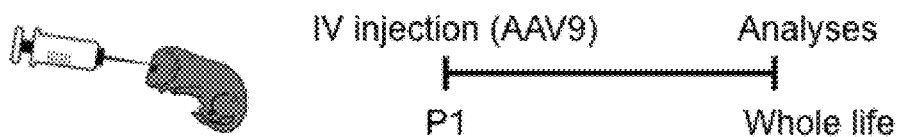

HITI was used to allow targeted gene correction of diseases with a point mutation in addition to large deletion as shown in the previous data of Retinitis Pigmentosa (RP) rat model. For proof-of-concept, a Hutchinson-Gilford progeria syndrome (HGPS) or progeria (LAKI) mouse model was used, which harbors an autosomal dominant point mutation in the LMNA gene (LmNA$^{G609G/G609G}$) and shows a premature aging phenotype in multiple tissues, abnormal protein (Progerin) accumulation in multiple organs, and shortened life span. To correct the mutation in whole body, AAV-HITI was systemically injected through intravenous (IV) injection at day 1. (See schematic in FIG. 16A)

Figure 16B:
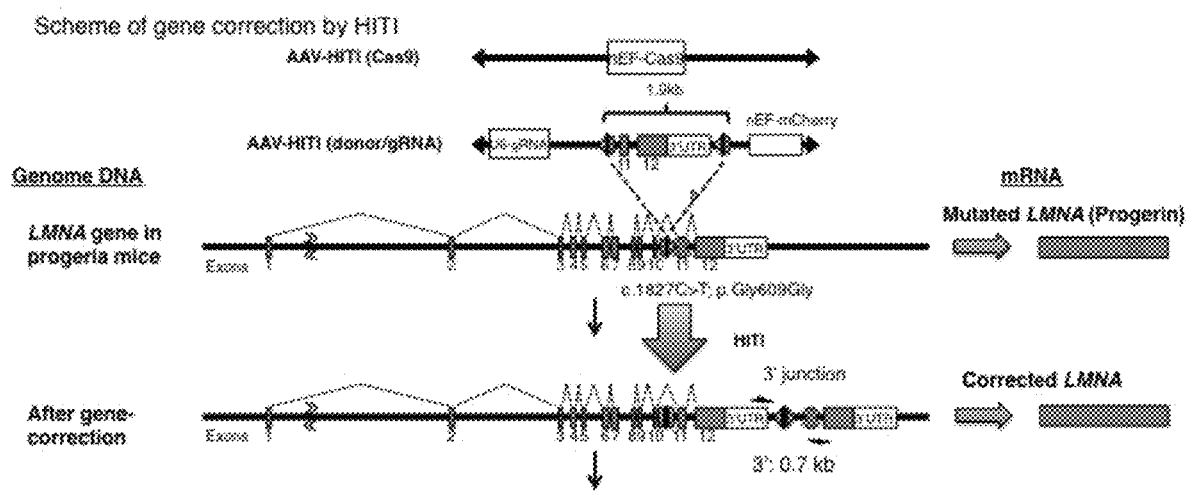

It was shown in an above example that HITI system can insert DNA to correct large DNA deletion. This example shows a new HITI strategy that introduce functional exons and 3'UTR in front of the mutated exon, thereby broadening the capability of HITI, e.g. point mutation, multiple mutations in the same gene. This mouse model has C-to-T dominant point mutation in exon 11, so a functional exon 11, 12 and 3'UTR was inserted into intron 10 by HITI. FIG. 16B shows a scheme of LMNA gene correction AAV vectors with serotype 9.

Figure 16C:
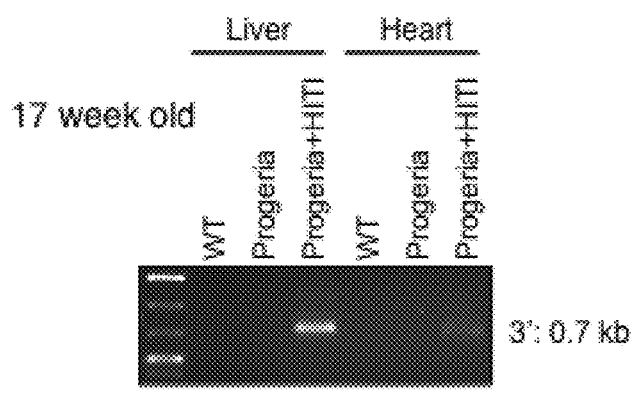
Figure 16D:
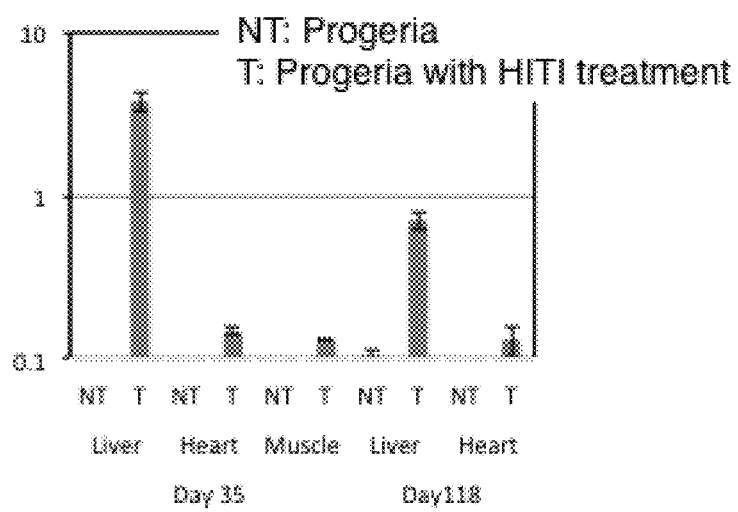

It was hypothesized that the inserted cassette is then transcribed, rather than the dysfunctional endogenous exons, thereby restoring non-mutated, wild type transcripts. Although the mutation will be still present in the genome, it will not affect the expression of the corrected transcript. Seventeen weeks after injection, the knock-in correction was seen at DNA level. Validation of correct gene knock-in by PCR at day 118 (FIG. 16C). Gene knock-in efficiency by qPCR at day 35 and 118 (FIG. 16D).

Figure 16E:
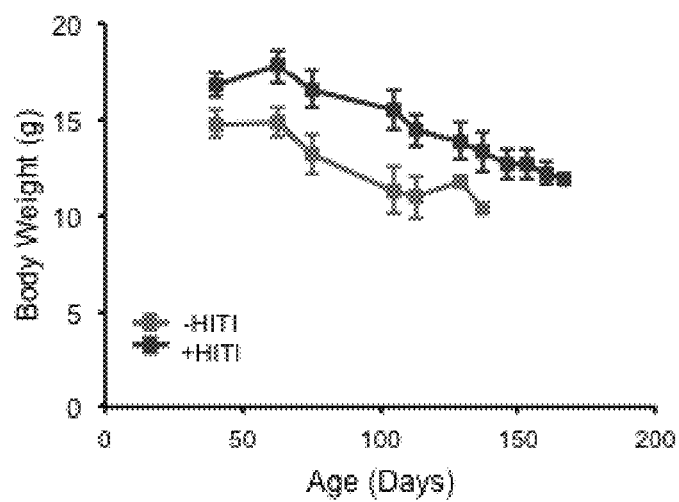
Figure 16F:
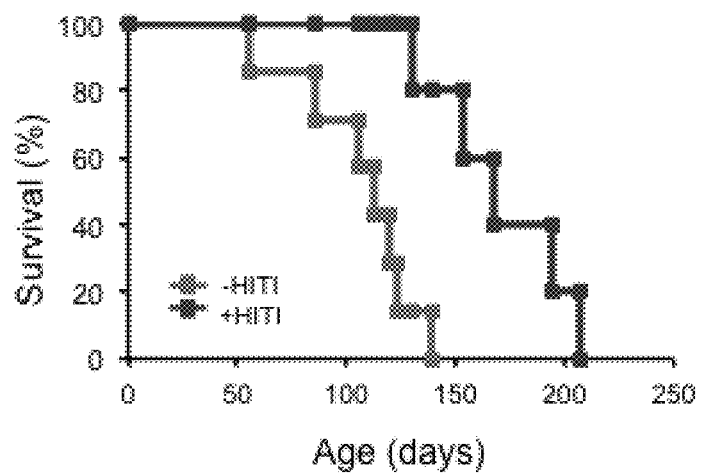

Progeria mouse model shows smaller body weights and shorter life span. Both phenotypes were significantly rescued by HITI treatment (FIG. 16E, weight; FIG. 16F, lifespan). These results suggest that HITI-mediated in vivo gene correction has achieved the therapeutic efficacy for dominant point mutation as well.

Figure 16G:
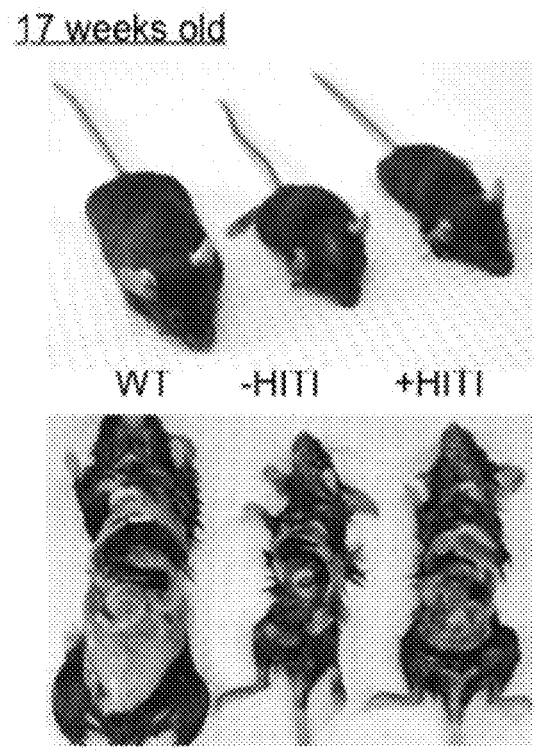
Figure 16H:
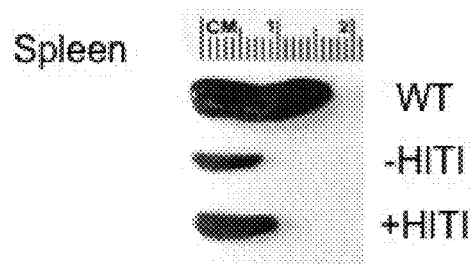

The appearance of treated mice was also affected by HITI treatment. FIG. 16G shows representative photographs of 4-month-old Lmna$^{+/+}$ (WT), Lmna$^{G609G/G609G}$ (–HITI), and HITI treated Lmna$^{G609G/G609G}$ mice (+HITI) at 17 weeks of age. The treated mice are slightly larger than the untreated mice and have improved organ appearance in dissected mice. Treated mice also show partial rescue of spleen regression, shown in FIG. 16H.

Figure 16I:
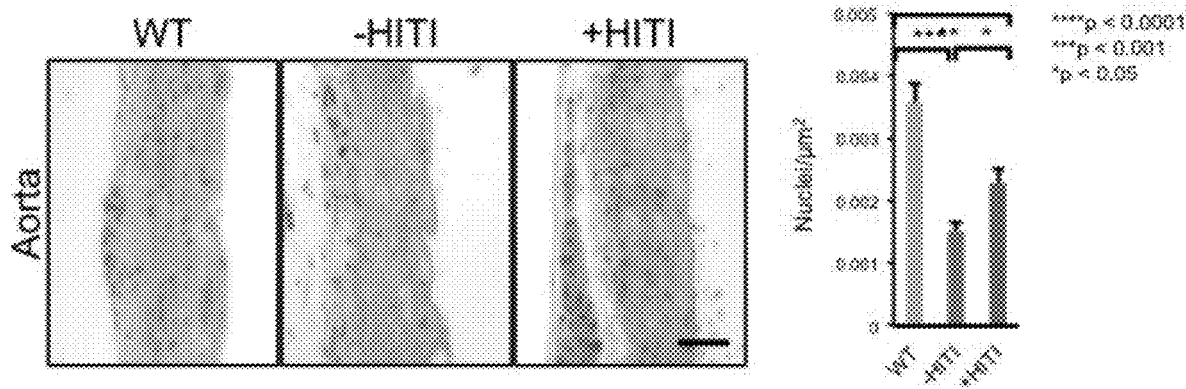

Improvement in histology (H&E) of aortic arch of LAKI HITI-treated mice was also shown. FIG. 16I shows exemplary histology photographs paired with a quantification of nuclear density which was partially rescued by HITI treatment.

Also improved was histology (PAS) of kidney of LAKI HITI-treated mice. The area of glomerulus and diameter of retinal tubules in the kidney was partially rescued by HITI treatment. A photomicrograph is shown along with quantification of area of kidney glomerulus and diameter of renal tubules in FIG. 16J.

Histology (H&E) of spleen of LAKI HITI-treated mice was also improved, including the area of white pulps in the spleen was partially rescued by HITI treatment. An exemplary photomicrograph of spleen in treated mice and a quantification of area of white pulp is shown in FIG. 16K.

This example shows that HITI-mediated in vivo gene correction has achieved the therapeutic efficacy for Progeria mouse model which have "dominant" and "point" mutation.

Example 10: Treatment of Retinitis Pigmentosa in Humans

A composition comprising AAV-Cas9 and AAV-rMertk is used to treat an individual suffering from retinitis pigmentosa. After administration of the composition to the subject by intravenous administration, the composition is able to correct the mutation in the Mertk gene and retinitis pigmentosa symptoms including decreased vision are improved. When 10 patients are given the intravenous injection of the composition, 9 experience an improvement in vision.

Example 11: Treatment of Progeria in Humans

A composition comprising AAV-HITI correcting the mutation in the LMNA gene (LMNAG609G/G609G) is used to treat an individual suffering from progeria. After administration of the composition to the subject by intravenous administration, the composition is able to correct the mutation in the LMNA gene and progeria symptoms including kidney function, spleen function, slow growth, and hair loss are improved. When 10 patients are given the intravenous injection of the composition, 9 experience an improvement in symptoms of progeria.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. Recombinant vectors configured to integrate an exogenous DNA sequence into a target nucleic acid sequence in a genome of a cell, wherein the vectors collectively encode:
 a targeting construct comprising the exogenous DNA sequence and a target sequence entirely in reverse orientation with respect to the exogenous DNA sequence;
 a complementary strand oligonucleotide homologous to the target sequence;
 a nuclease capable of producing double stranded DNA blunt end cuts;
 wherein the exogenous DNA sequence comprises at least one nucleotide difference compared to the genome, both the target sequence and the target nucleic acid sequence in the genome are recognized and cut by the nuclease, and the recombinant vectors are configured such that that the target nucleic acid sequence in the genome is no longer present once the exogenous DNA sequence has been integrated into the genome in the correct orientation.

2. The recombinant vectors of claim 1, wherein the targeting construct, the complementary strand oligonucleotide, and the nuclease are all encoded by a single vector.

3. The recombinant vectors of claim 1, wherein the nuclease is encoded by a nuclease vector; and
 the targeting construct and the complementary strand oligonucleotide are encoded by a targeting vector.

4. The recombinant vectors of claim 3, wherein the targeting construct comprises a second target sequence entirely in reverse orientation with respect to the exogenous DNA sequence, and the second target sequence is configured to be recognized and cut by the nuclease.

5. The recombinant vectors of claim 4, wherein the recombinant vectors are adeno-associated virus vectors.

6. The recombinant vectors of claim 1, wherein the recombinant vectors comprise lentiviral vectors, retroviral vectors, adenoviral vectors, or adeno-associated viral vectors.

7. The recombinant vectors of claim 1, wherein the target nucleic acid sequence in the genome is within Mertk, LMNA, rhodopsin, or alpha 1-antitrypsin.

8. A method of treating a genetic disease in a subject in need thereof, wherein the genetic disease results from a mutated gene or fragment thereof having at least one changed nucleotide compared to a wild-type gene or fragment thereof, comprising contacting at least one cell of the subject with the recombinant vectors of claim 6;
 wherein the genetic disease is retinitis pigmentosa, muscular dystrophy, Hutchinson-Gilford progeria syndrome, or an alpha 1-antitrypsin deficiency.

9. The recombinant vectors of claim 1, wherein the exogenous DNA sequence corrects a mutation in the genome of the cell.

10. The recombinant vectors of claim 1, wherein the exogenous DNA sequence causes a mutation in the genome of the cell and the mutation is selected from a mis sense mutation, a nonsense mutation, a silent mutation, an insertion, and a deletion.

11. The recombinant vectors of claim 1, wherein the nuclease is a CRISPR Cas9 nuclease.

12. The recombinant vectors of claim 1, wherein the cell is a non-dividing cell.

13. The recombinant vectors of claim 12, wherein the non-dividing cell comprises a terminally differentiated cell or a quiescent stem cell.

14. The recombinant vectors of claim 12, wherein the non-dividing cell is one or more of a lymphocyte, a monocyte, a neutrophil, an eosinophil, a basophil, an endothelial cell, an epithelial cell, a hepatocyte, an osteocyte, a platelet, an adipocyte, a cardiomyocyte, a neuron, a retinal cell, a smooth muscle cell, a skeletal muscle cell, a spermatocyte, an oocyte, and a pancreas beta cell.

15. The recombinant vectors of claim 1, wherein there are at least two copies of the targeting sequence entirely in reverse orientation with respect to the exogenous DNA sequence within the targeting construct.

16. The recombinant vectors of claim 1, further comprising a pharmaceutically acceptable buffer or excipient.

17. Viral particles comprising the recombinant vectors of claim 1.

18. The viral particles of claim 17, wherein the nuclease is packaged into a nuclease viral particle; and the targeting construct and the complementary strand oligonucleotide are packaged into a targeting viral particle.

19. The viral particles of claim 17, wherein the viral particles are lentiviral particles, retroviral particles, adenoviral particles, or adeno-associated viral particles.

20. The viral particles of claim 17, further comprising a pharmaceutically acceptable buffer or excipient.

\* \* \* \* \*